(12) United States Patent
Genova et al.

(10) Patent No.: US 11,147,434 B2
(45) Date of Patent: Oct. 19, 2021

(54) SYSTEMS, METHODS, AND APPARATUSES FOR CAPTURING IMAGES DURING A MEDICAL PROCEDURE

(71) Applicant: Titan Medical Inc., Toronto (CA)

(72) Inventors: Perry A. Genova, Chapel Hill, NC (US); Sachin A. Sankholkar, Highlands Ranch, CO (US); Hans Christian Pflaumer, Apex, NC (US); Aki Hannu Einari Laakso, Raleigh, NC (US); Allan Katz, Farmingdale, NY (US); Alejandro Espinosa, Miramar, FL (US); Eduardo A. Ampuero, Miramar, FL (US)

(73) Assignee: TITAN MEDICAL INC., Toronto (CA)

( * ) Notice: Subject to any disclaimer, the term of this patent is extended or adjusted under 35 U.S.C. 154(b) by 210 days.

(21) Appl. No.: 16/449,095

(22) Filed: Jun. 21, 2019

(65) Prior Publication Data

US 2020/0113645 A1    Apr. 16, 2020

Related U.S. Application Data

(63) Continuation-in-part of application No. 16/299,834, filed on Mar. 12, 2019, which is a
(Continued)

(51) Int. Cl.
*A61B 1/00*    (2006.01)
*A61B 1/05*    (2006.01)
(Continued)

(52) U.S. Cl.
CPC ........ *A61B 1/00135* (2013.01); *A61B 1/0005* (2013.01); *A61B 1/00006* (2013.01);
(Continued)

(58) Field of Classification Search
CPC ............ A61B 1/00009; A61B 1/00135; A61B 1/00154; A61B 1/00177
(Continued)

(56) References Cited

U.S. PATENT DOCUMENTS

| 5,235,965 A | 8/1993 | Hiroya |
| 5,299,559 A | 4/1994 | Bruce |

(Continued)

OTHER PUBLICATIONS

International Search Report dated Jan. 23, 2020 in International Application No. PCT/US2019/055255, in 5 pages.
(Continued)

*Primary Examiner* — Aaron B Fairchild

(57) ABSTRACT

An insertion device for a single port robotic surgery apparatus can include an insertion section with first and second camera channels and an instrument channel, the first camera channel configured to facilitate insertion and removal of a primary camera, the second camera channel configured to enclose a secondary camera, and the instrument channel configured to permit insertion and removal of a surgical instrument from the insertion section, The insertion device can include a housing attached to the insertion section, the housing including a passage configured to permit at least a portion of the primary camera to pass through the housing into the first camera channel and exit the first camera channel. The secondary camera can be configured to provide image data of a surgical site to facilitate insertion into the surgical site of at least one of the surgical instrument or the primary camera.

18 Claims, 40 Drawing Sheets

Related U.S. Application Data continuation-in-part of application No. 16/156,651, filed on Oct. 10, 2018, now Pat. No. 10,624,532, and a continuation of application No. 16/156,625, filed on Oct. 10, 2018, now Pat. No. 10,398,287.

(51) Int. Cl.
*A61B 1/04* (2006.01)
*H04N 5/225* (2006.01)
*A61B 34/30* (2016.01)

(52) U.S. Cl.
CPC ...... *A61B 1/00009* (2013.01); *A61B 1/00045* (2013.01); *A61B 1/00154* (2013.01); *A61B 1/04* (2013.01); *A61B 1/05* (2013.01); *A61B 34/30* (2016.02); *H04N 5/22525* (2018.08)

(58) Field of Classification Search
USPC .......................................................... 600/114
See application file for complete search history.

(56) References Cited

U.S. PATENT DOCUMENTS

| | | | |
|---|---|---|---|
| 6,352,503 B1* | 3/2002 | Matsui | A61B 17/1285 600/104 |
| 9,271,637 B2 | 3/2016 | Farr | |
| 9,492,065 B2 | 11/2016 | Tesar et al. | |
| 9,801,551 B2 | 10/2017 | Herzlinger et al. | |
| 9,877,744 B2 | 1/2018 | Cooper et al. | |
| 10,011,018 B2 | 7/2018 | McGrogan et al. | |
| 2003/0233024 A1 | 12/2003 | Ando | |
| 2006/0252993 A1 | 11/2006 | Freed | |
| 2007/0043338 A1 | 2/2007 | Moll et al. | |
| 2007/0135803 A1 | 6/2007 | Belson | |
| 2007/0238927 A1 | 10/2007 | Ueno | |
| 2008/0033450 A1 | 2/2008 | Bayer et al. | |
| 2008/0287961 A1* | 11/2008 | Miyamoto | A61B 1/0684 606/127 |
| 2009/0062615 A1* | 3/2009 | Yamaya | G02B 23/243 600/167 |
| 2011/0208000 A1 | 8/2011 | Honda | |
| 2013/0282041 A1 | 10/2013 | Gunday et al. | |
| 2014/0107417 A1 | 4/2014 | McKinley et al. | |
| 2015/0141755 A1 | 5/2015 | Tesar | |

OTHER PUBLICATIONS

International Preliminary Report dated Apr. 8, 2021 and Written Opinion completed Jan. 23, 2020 corresponding to counterpart Int'l Patent Application PCT/US2019/055255.

Advanced Sterilization Products, "Sterrad 100NX," downloaded on Oct. 8, 2018 from https://www.emea.aspjj.com/sites/aspjj.com.emea/files/pdf/STERRADFF_FamilyOfProducts_0.pdf, in 12 pages.

Intuitive Surgical, "da Vinci SP," downloaded on Oct. 9, 2018 from https://www.intuitivesurgical.com/sp/, in 5 pages.

Olympus America, "Rigid Laparoscopes," downloaded on Oct. 8, 2018 from http://medical.olympusamerica.com/products/rigid-laparoscopes, in 2 pages.

* cited by examiner

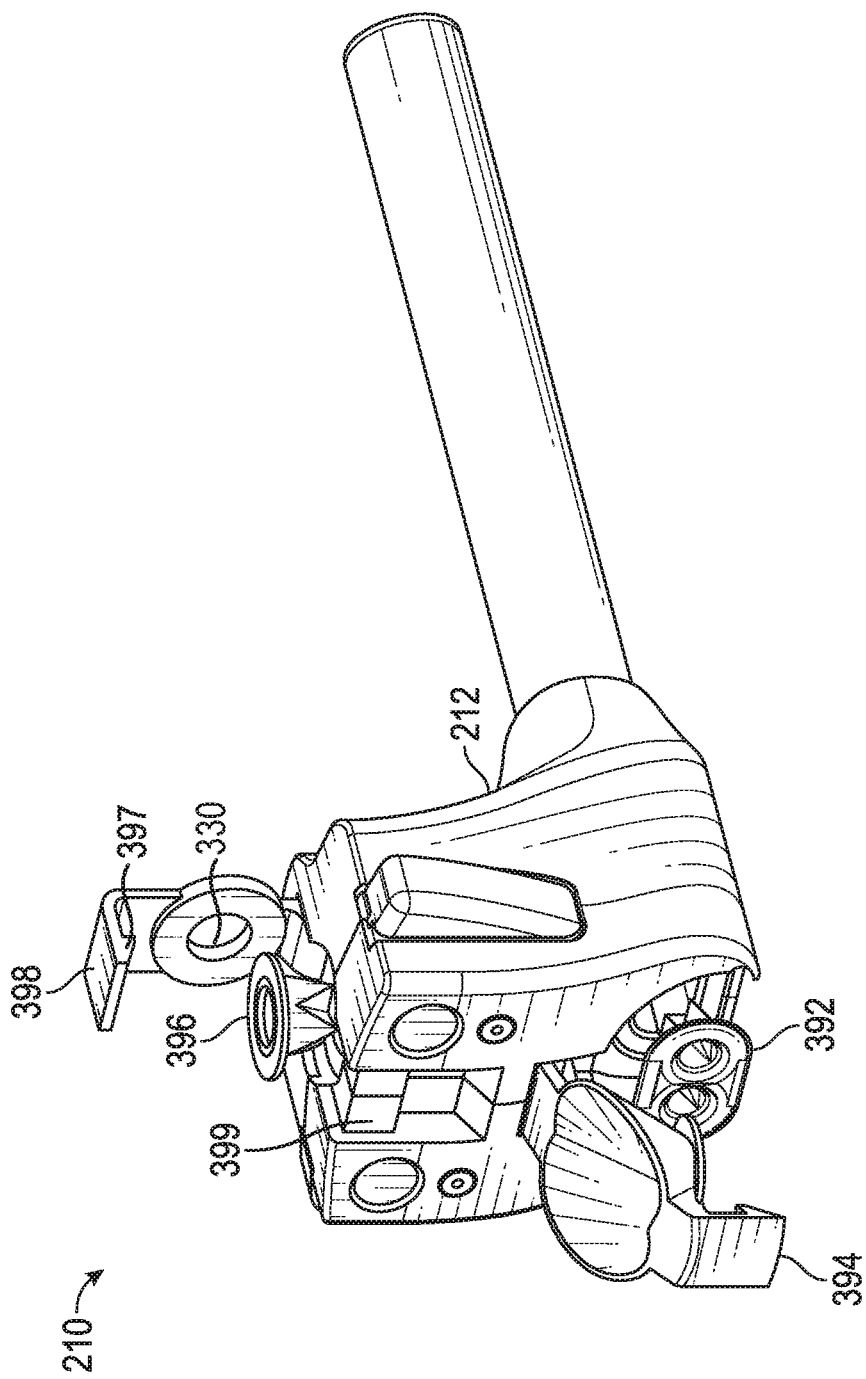

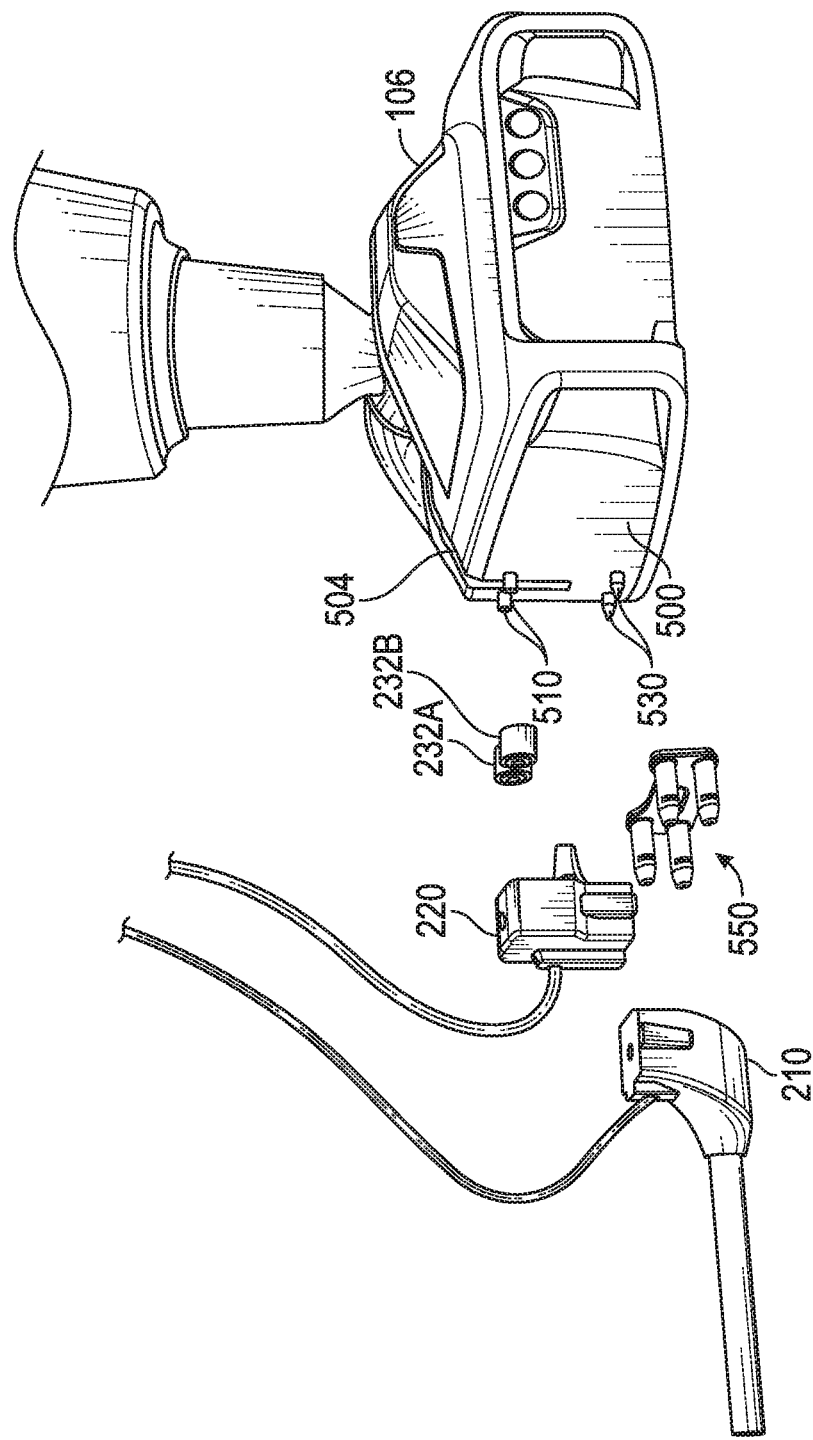

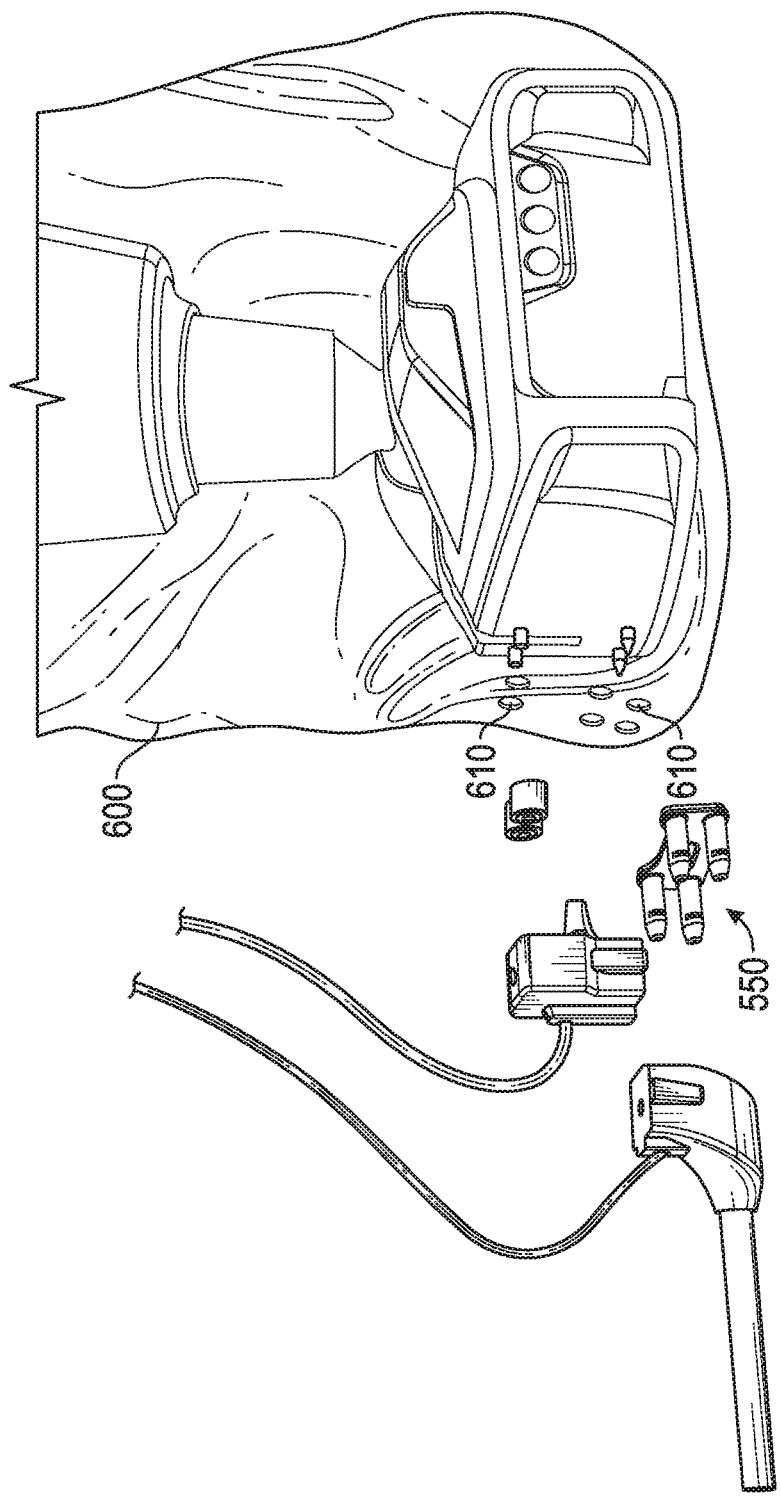

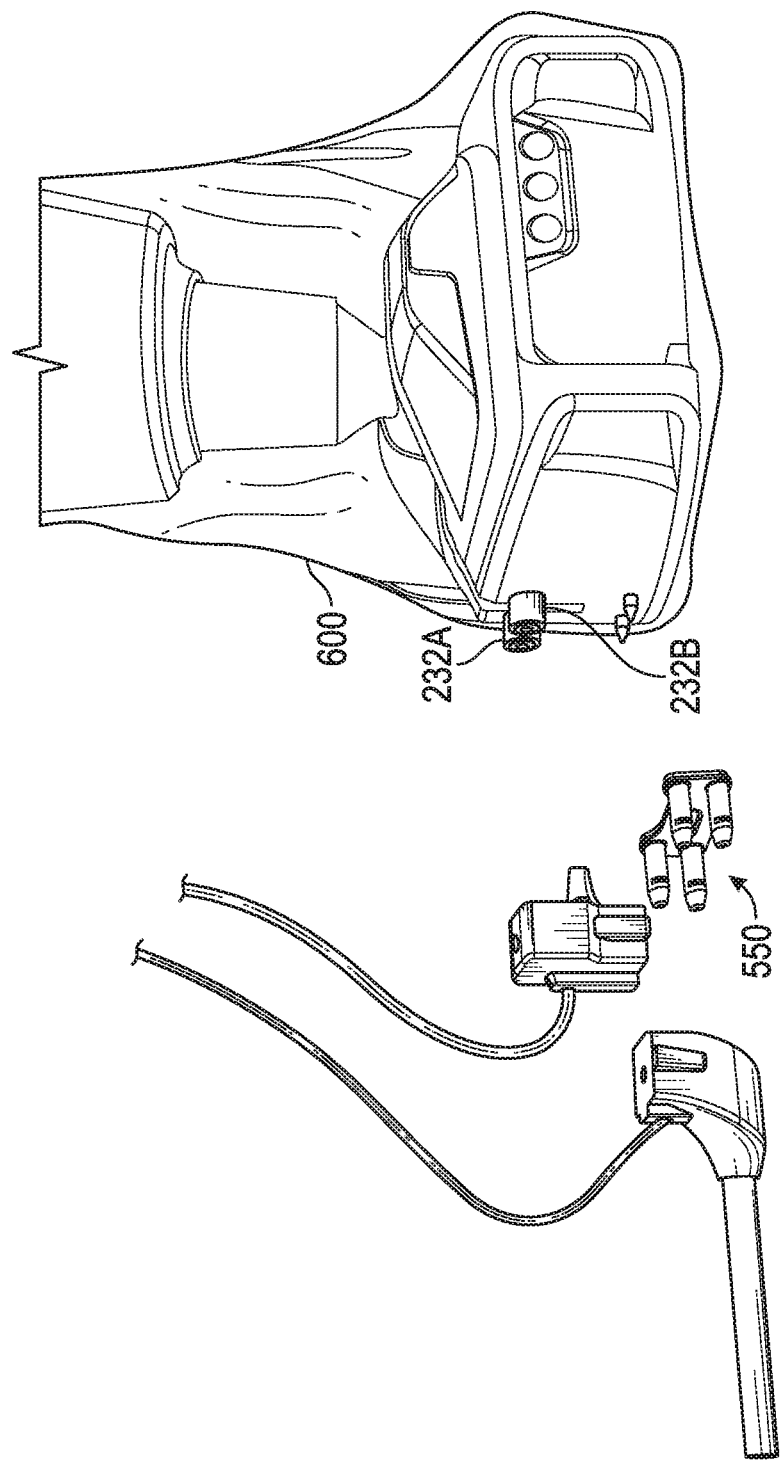

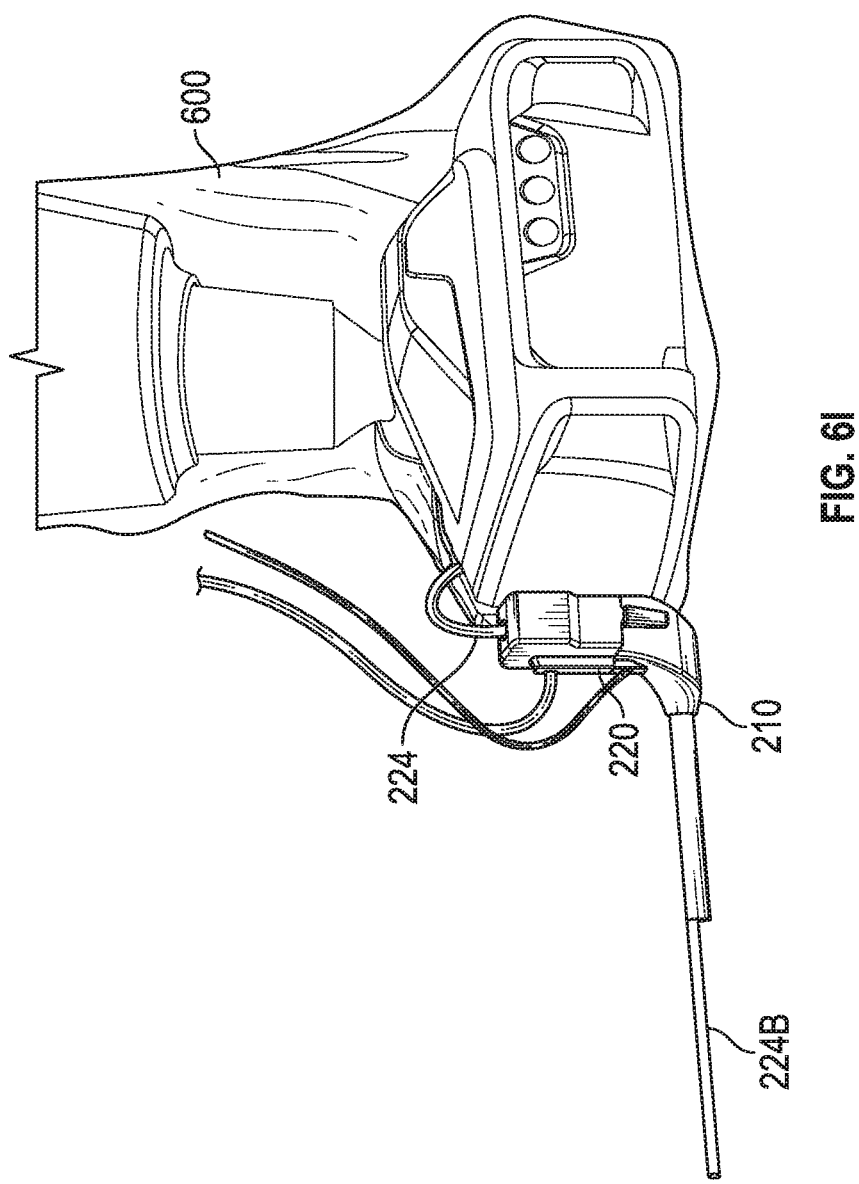

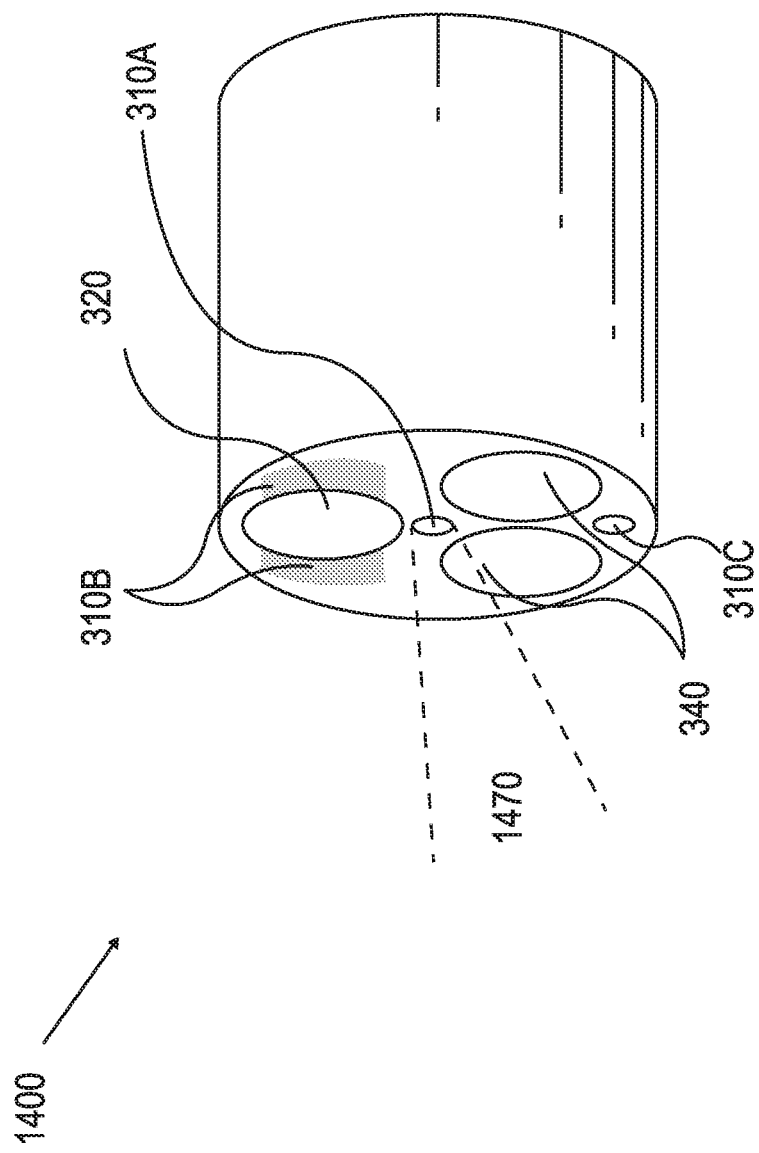

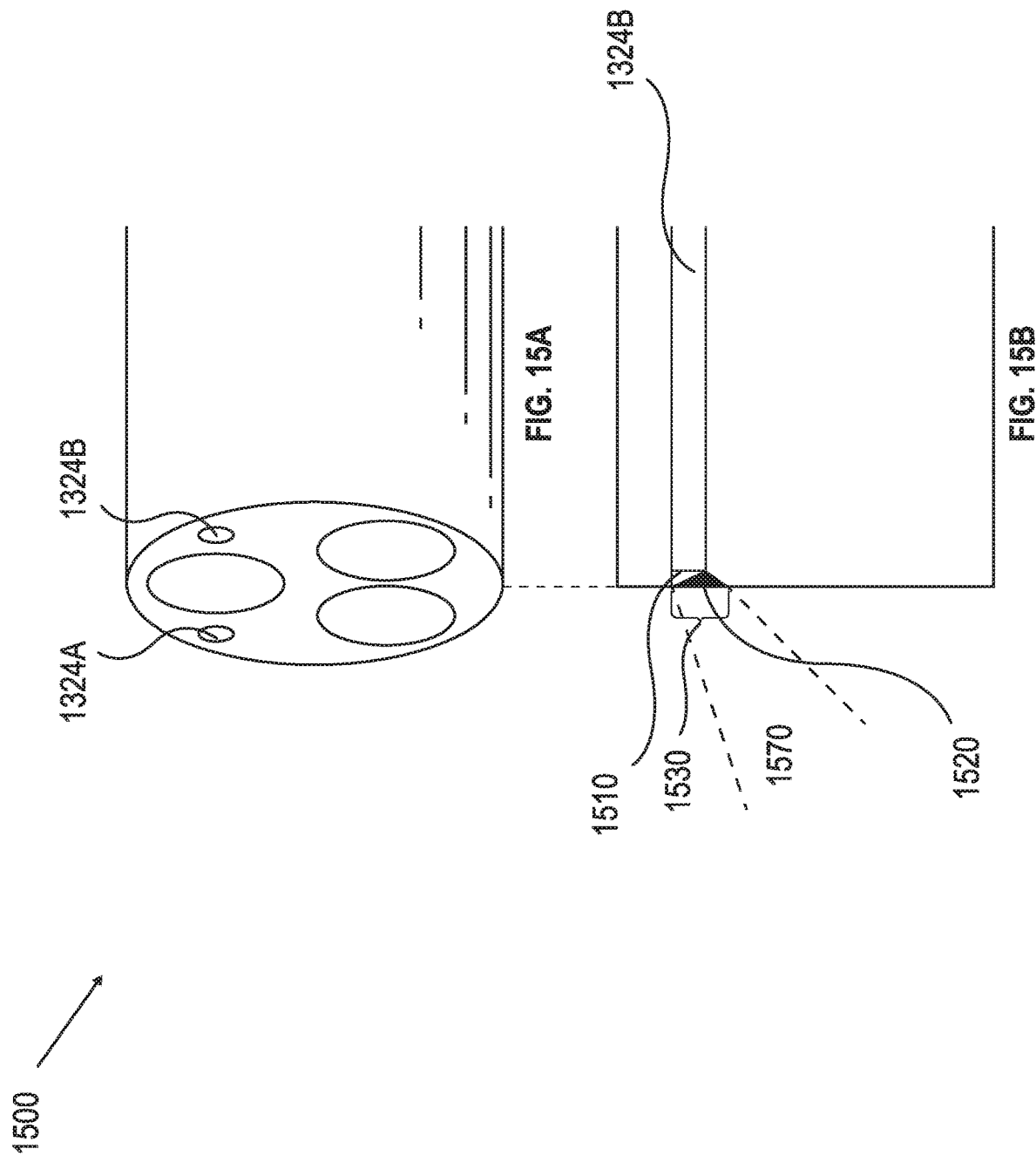

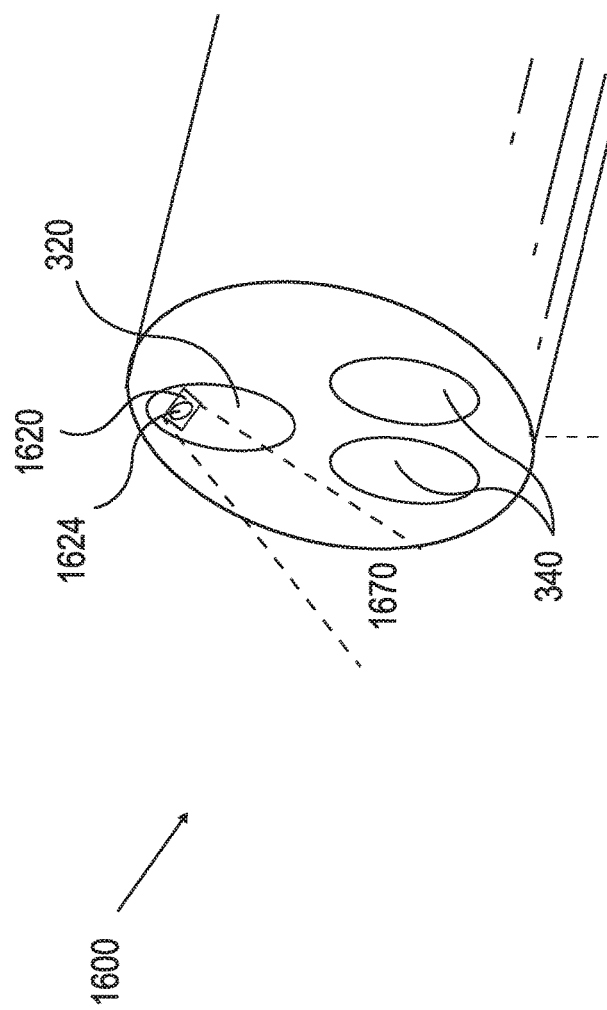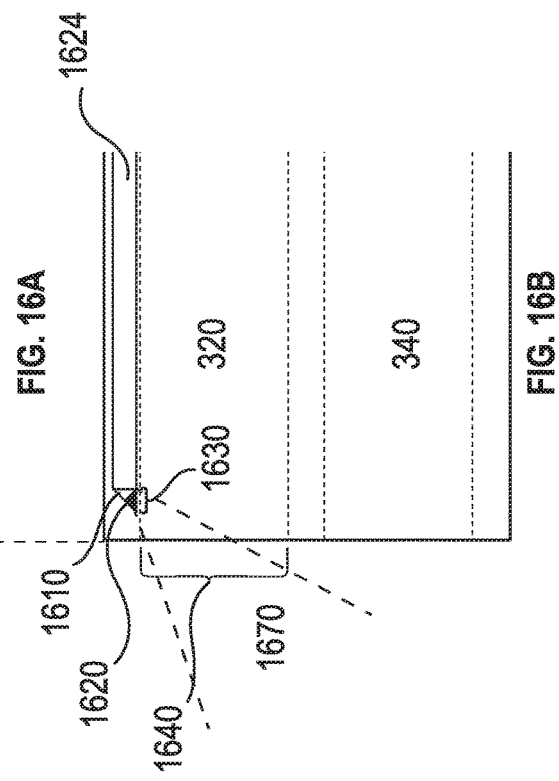

SYSTEMS, METHODS, AND APPARATUSES FOR CAPTURING IMAGES DURING A MEDICAL PROCEDURE

CROSS-REFERENCE TO RELATED APPLICATIONS

This application is a continuation-in-part of U.S. patent application Ser. No. 16/299,834, filed on Mar. 12, 2019, which is a continuation-in-part of U.S. patent application Ser. Nos. 16/156,651 and 16/156,625, filed on Oct. 10, 2018, the disclosure of each of which is incorporated by reference in its entirety.

TECHNICAL FIELD

This disclosure relates generally to positioning a camera for imaging and more particularly to positioning a camera inside a body cavity of a patient for capturing images during a medical procedure.

DESCRIPTION OF RELATED ART

Miniaturized cameras are used during investigative medical procedures and surgical procedures, such as laparoscopic surgery and computer assisted robotic surgery, to produce images of a site of the procedure within a body cavity of the patient. A camera generally includes an illumination source for illuminating the site of the procedure and a lens for capturing images of the site. Known camera systems suffer from a variety of shortcomings, including large size, poor resolution, obstacles with being sterilized, lack of reliability, difficulties with being replaced during medical procedure, and the like. The present disclosure overcomes these and other problems associated with known camera systems, methods, and apparatuses.

SUMMARY

An insertion device for a single port robotic surgery apparatus can include an insertion section with first and second camera channels and an instrument channel extending along at least a portion of the insertion section. The first camera channel can be configured to facilitate insertion and removal of a primary camera from the insertion section. The second camera channel can be configured to enclose a secondary camera. The instrument channel can be configured to permit insertion and removal of a surgical instrument from the insertion section. The insertion device can include a housing attached to the insertion section. The housing can include a passage configured to permit at least a portion of the primary camera to pass through the housing into the first camera channel and exit the first camera channel. The housing can be configured to be removably attached to a robotic surgery apparatus. The secondary camera can be configured to provide image data of a surgical site to facilitate insertion into the surgical site of at least one of the surgical instrument or the primary camera.

The insertion device of the preceding paragraph and/or any of the insertion device disclosed herein can include one or more of the following features. The secondary camera can be configured to provide the image data of the surgical site prior to attachment of the housing to the robotic surgery apparatus. Attachment of the housing to the robotic surgery apparatus can include mounting the housing with a mounting interface of the robotic surgery apparatus. The second camera channel can include a plurality of second camera channels enclosing a plurality of secondary cameras. The second camera channel can be positioned between the first camera channel and the instrument channel. The plurality of second camera channels can include two second camera channels positioned on opposite sides of the first camera channel and adjacent to the first camera channel. The secondary camera can include prism positioned at a distal end of the secondary camera, the prism configured to cause a field of view of the secondary camera to be oriented downward. The secondary camera can include a lens. The prism can be positioned closer to the distal end of the secondary camera than a lens of the secondary camera. The secondary camera can include a fisheye lens. The second camera channel can be configured to enclose a device configured to image the surgical site or perform another function when the secondary camera has been removed. The passage can be vertically aligned with the first camera channel. The secondary camera can be integral with the second camera channel. The instrument channel can include a plurality of instrument channels configured to permit insertion and removal of a plurality of surgical instruments.

A robotic surgery system can include the insertion device of any of the preceding paragraphs or described herein. The system can include a robotic surgery workstation that includes a first display configured to display image data received from at least one of the primary or secondary camera, and electronic circuitry configured to receive the image data and to control the first display to display the image data.

The robotic surgery system of the preceding paragraph and/or any of the robotic surgery systems disclosed herein can include one or more of the following features. The image data can include first image data captured by the secondary camera and second image data captured by the primary camera. The electronic circuitry can be configured to display to display the first image data, and control the first display to display the second image data in response to a determination that the primary camera is connected. Determination that the primary camera is connected can include at least one of a determination that the primary camera is mounted to a mounting interface of the system, a determination that primary camera is electrically connected to the electronic circuitry, or a determination that a distal portion of the primary camera has exited out the first camera channel. The electronic circuitry can be configured to control the first display to display the first image data overlaid on the second image data in response to the determination that the primary camera is connected. The system can include a second display. The electronic circuitry can be configured to control the second display to display the first image data when the first display displays the second image data and not the first image data. The electronic circuitry can be configured to control the first display to display the first image in response to a determination that the primary camera is disconnected. Determination that the primary camera is disconnected can include at least one of: a determination that the primary camera is not mounted to a mounting interface of the system, a determination that the primary camera is not electrically connected to the electronic circuitry, a determination that a distal portion of the primary camera has not exited the first camera channel, a determination that the primary camera has failed, or a determination that the primary camera is not communicating with the electronic circuitry.

A robotic surgery system can include an insertion device including first and second camera channels and an instrument channel. The first camera channel can be configured to facilitate insertion and removal of a primary camera from the insertion device. The second camera channel can be configured to enclose a secondary camera. The instrument channel can be configured to permit insertion and removal of a surgical instrument from the insertion device. The secondary camera can be configured to provide first image data of a surgical site to facilitate insertion into the surgical site of at least one of the surgical instrument or the primary camera. The system can include a robotic surgery workstation with a first display configured to display image data received from at least one of the primary camera or secondary camera. The workstation can include electronic circuitry configured to receive the image data and to control the first display to display the image data.

The robotic surgery system of the preceding paragraph and/or any of the robotic surgery systems disclosed herein can include one or more of the following features. The electronic circuitry can be configured to control the first display to display the first image data and control the first display to display second image data provided by the primary camera in response to a determination that the primary camera is connected. Determination that the primary camera is connected can include at least one of a determination that the primary camera is mounted to a mounting interface of the system, a determination that primary camera is electrically connected to the electronic circuitry, or a determination that a distal portion of the primary camera has exited out the first camera channel. The electronic circuitry can be configured to control the first display to display the first image data overlaid on the second image data in response to the determination that the primary camera is connected. The system can include a second display. The electronic circuitry can be configured to control the second display to display the first image data when the first display displays the second image data and not the first image data. The electronic circuitry can be configured to control the first display to display the first image in response to a determination that the primary camera is disconnected. Determination that the primary camera is disconnected can include at least one of: a determination that the primary camera is dismounted from a mounting interface of the system, a determination that the primary camera is not electrically connected to the electronic circuitry, a determination that a distal portion of the primary camera has not exited out the first camera channel, or a determination that a distal portion of the primary camera has not exited the first camera channel, a determination that the primary camera has failed, or a determination that the primary camera is not communicating with the electronic circuitry.

A method of operating a robotic surgery system can include, by electronic circuitry of the robotic surgery system, receiving image data from at least one of a primary camera or a secondary camera of the robotic surgery system. The primary camera can be enclosed in a first camera channel of an insertion device of the robotic surgery system. The secondary camera can be enclosed in a second camera channel of the insertion device. The secondary camera can facilitate insertion into a surgical site of at least one of the surgical instrument or the primary camera. The method can include controlling a first display of the robotic surgery system to display the image data.

The method the preceding paragraph and/or any of the methods disclosed herein can include one or more of the following features. The secondary camera can further facilitate insertion of a surgical instrument into the surgical site. The surgical instrument can be enclosed in an instrument channel of the insertion device. The method can include, by the electronic circuitry, controlling the first display to display first image data captured by the secondary camera. The method can include, in response to determining that the primary camera is connected, controlling the first display to display second image data captured by the primary camera. Determining that the primary camera is connected can include at least one of: determining that the primary camera is mounted to a mounting interface of the robotic surgery system, determining that primary camera is electrically connected to the electronic circuitry, or determining that a distal portion of the primary camera has exited the first camera channel. The method can include, by the electronic circuitry, controlling the first display to display the first image data overlaid on the second image data in response to determining that the primary camera is connected. The method can include, by the electronic circuitry, controlling a second display of the robotic surgery system to display the first image data when the first display displays the second image data and not the first image data. The method can include, by the electronic circuitry, controlling the first display to display the first image in response to a determination that the primary camera is disconnected. Determining that the primary camera is disconnected can include at least one of: determining that the primary camera is dismounted from a mounting interface of the system, determining that the primary camera is not electrically connected to the electronic circuitry, determining that a distal portion of the primary camera has not exited the first camera channel, determining that a distal portion of the primary camera has not exited the first camera channel, determining that the primary camera has failed, or determining that the primary camera is not communicating with the electronic circuitry.

Any of the insertion devices of any of preceding paragraphs and/or described below can be used with any of visualization devices and/or robotic surgery systems described herein.

In some cases, a robotic surgery apparatus as described and/or illustrated is provided. In some cases, a visualization device as described and/or illustrated is provided. In some cases, an insertion device as described and/or illustrated is provided.

In some cases, a method of using and/or operating a robotic surgery apparatus or any of its components as described and/or illustrated is provided. In some cases, a method of using and/or operating a visualization device as described and/or illustrated is provided. In some cases, a method of using and/or operating an insertion device as described and/or illustrated is provided.

Any of the methods of any of preceding paragraphs and/or described below can be used with any of insertion devices, visualization devices, and/or robotic surgery systems and/or any of the methods of operating and/or using such devices and/or systems described herein.

BRIEF DESCRIPTION OF THE DRAWINGS

Embodiments of the present disclosure will now be described hereinafter, by way of example only, with reference to the accompanying drawings in which:

FIGS. 3A-3E illustrate an insertion device according to some embodiments;

FIGS. 6A-6I illustrate attachment of insertion and visualization devices to a mounting interface of a drive unit of a robotic surgery system according to some embodiments;

FIGS. 13, 14, 15A, 15B, 16A, and 16B illustrate insertion devices according to some embodiments.

DETAILED DESCRIPTION

Overview

When performing medical procedures (for example, with assistance of surgery using a robotic surgical system) one or more instruments can be inserted into a body cavity of a patient. The insertion process has some risk since instruments may inadvertently damage organs or tissue while being inserted. Incorrect positioning of the one or more instruments in the body cavity may also result in a limited range of motion within the body cavity.

As an example, when performing abdominal surgery, at least one incision would be made in a body wall of the patient's abdomen. A trocar or other access port, may then be inserted through the incision. A camera can be first inserted through the access port and used by a surgeon to capture and relay stereoscopic images of a surgical site. One or more instruments can be inserted following the camera insertion. Views provided by the camera facilitate insertion of the one or more instruments and their manipulation of the surgical site.

Figure 1A:
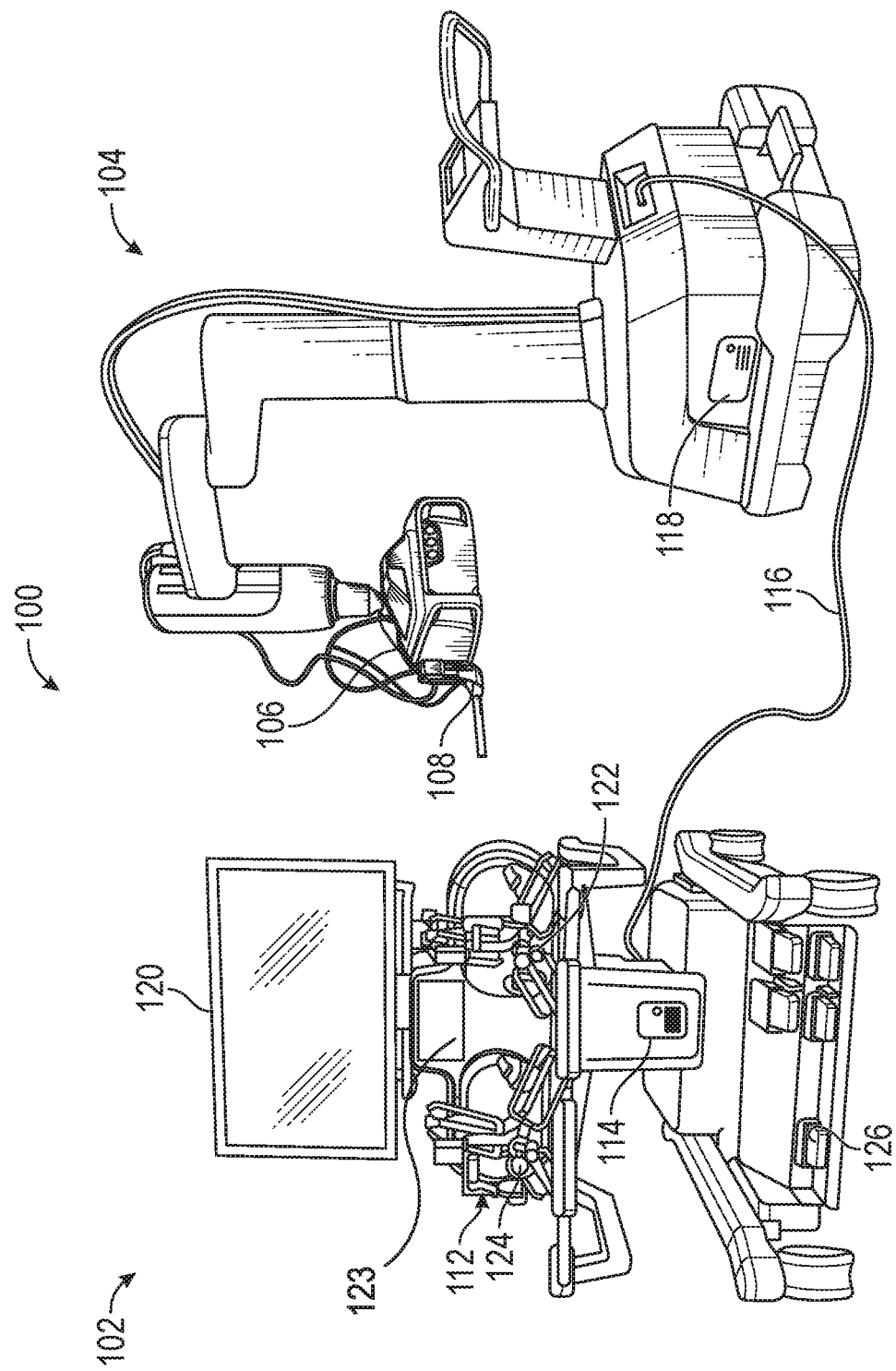
FIG. 1A illustrates a robotic surgery system in accordance with some embodiments.

Referring to FIG. 1A, a robotic surgery system in accordance with some embodiments is shown generally at 100. In some implementations, the robotic surgery system 100 can be configured to facilitate a medical procedure performed via a single incision. A single access port can be inserted into the incision to provide access for one or more instruments and cameras.

Figure 1B:
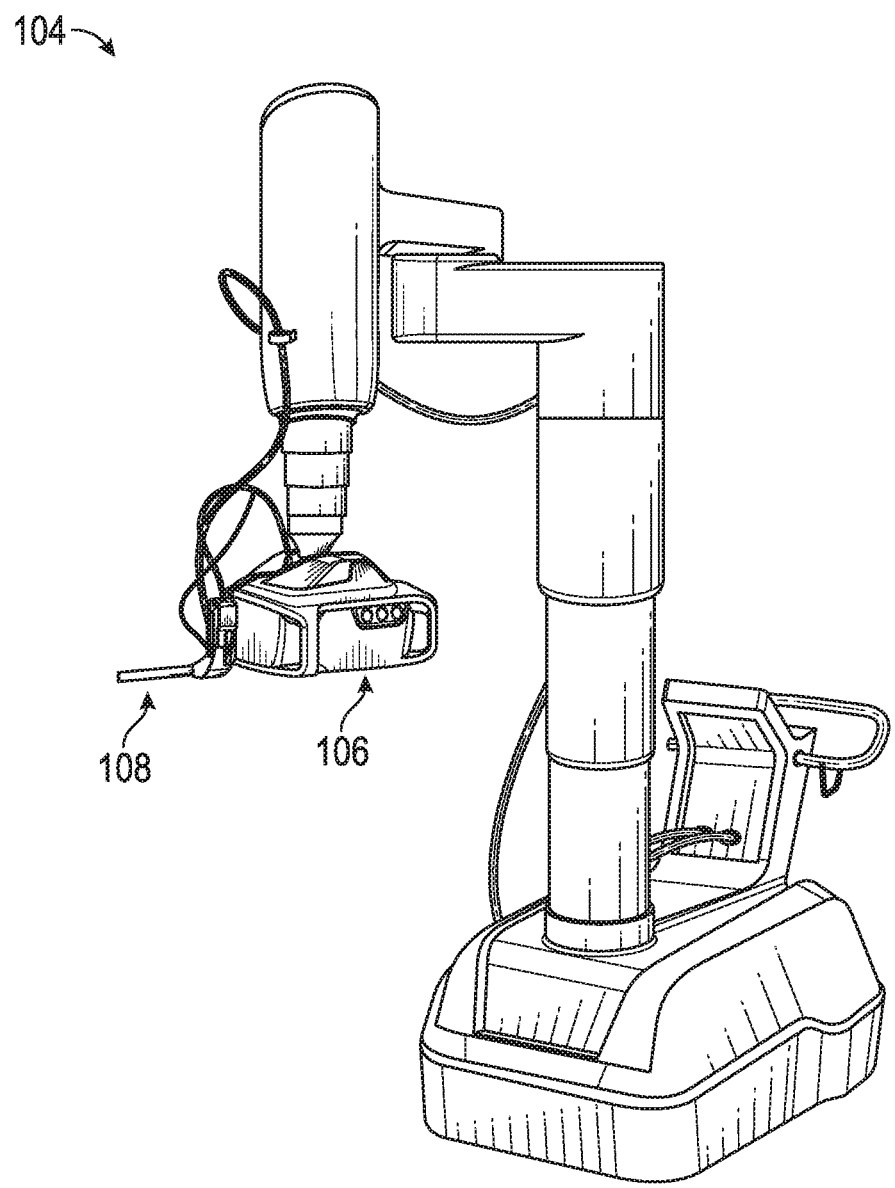
FIG. 1B illustrates a patient cart of a robotic surgery system according to some embodiments.

The system 100 can include a workstation 102 and a patient cart 104, which is illustrated in more detail in FIG. 1B. The patient cart 104 can include a central unit or drive unit 106 to which instrument insertion and visualization devices 108 can be attached or mounted. The workstation 102 can include an input device 112 that receives operator input and produces input signals and may also be configured to generate feedback to the operator. The feedback can be visual, auditory, haptic, or the like. The input device 112 can be implemented using a haptic interface available from Force Dimension, of Switzerland, for example.

The workstation 102 can further include a master processor circuit 114 in communication with the input device 112 for receiving the input signals and generating control signals for controlling the robotic surgery system, which can be transmitted to the patient cart 104 via an interface cable 116.

In some cases, transmission can be wireless and interface cable 116 may not be present. The input device 112 can include right and left hand controllers 122 and 124, which are configured to be grasped by the operator's hands and moved to produce input signals at the input device 112. The patient cart 104 can include a slave processor circuit 118 that receives and the control signals from the master processor circuit 114 and produces slave control signals operable to control the instrument insertion and visualization devices 108 and one or more instruments (and their respective end effectors) during a surgical procedure. The one or more instruments can include dexterous tools, such as grippers, needle drivers, staplers, dissectors, cutters, hooks, graspers, scissors, coagulators, irrigators, suction devices, which are used for performing a surgical procedure. While both master and slave processor circuits are illustrated, in other embodiments a single processor circuit may be used to perform both master and slave functions. The workstation 102 can also include a user interface, such as a display 120 (which can be referred to as a primary display) in communication with the master processor circuit 114 for displaying information (such as, body cavity images) for a region or site of interest (for example, a surgical site, a body cavity, or the like) and other information to an operator. The workstation 102 can include an auxiliary display 123 (which can be referred to as a secondary display) for displaying auxiliary surgical information, for example, patient medical charts, pre-operation images, images acquired during operation, or the like. In some cases, the secondary display 123 may be a touch display and may also be configured to display graphics representing additional inputs for controlling the workstation 102 or the patient cart 104. The workstation 102 can also include one or more controllers, such as one or more pedals 126, for controlling the robotic surgery system. For example, one or more pedals 126 can include a clutch pedal that allows repositioning one or more controllers 122 or 124 without corresponding movement of the associated instrument.

The workstation 102 can include electronic circuitry (of which the master processor circuit 114 can be part of), configured to, among other things, control one or more of the display 120 or the secondary display 123. The electronic circuitry can receive image data from one or more cameras described herein and operate one or more of the display 120 or the secondary display 123 to display the image data. The electronic circuitry can process the image data, such as filter, decode, encode, recode, compress, decompress, combine, or the like.

Figure 2A:
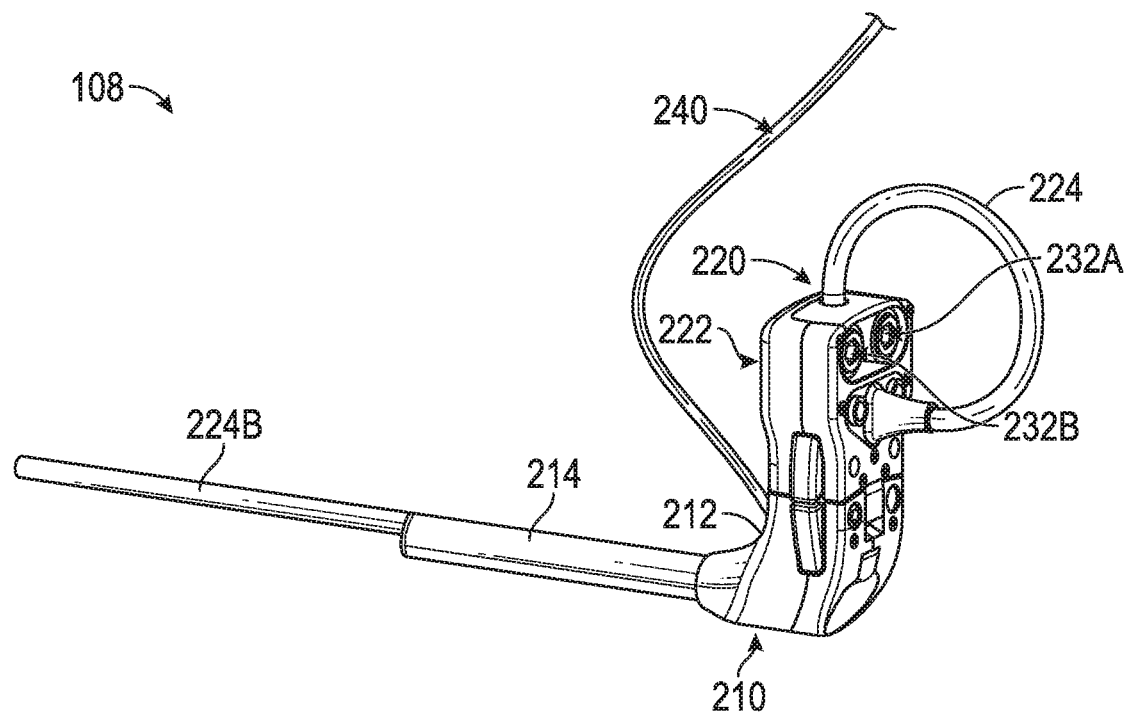
FIGS. 2A-2B illustrate insertion and visualization devices according to some embodiments.

Referring to FIG. 2A, in some embodiments, insertion and visualization devices 108 can include an insertion device 210 and a visualization device 220. The insertion device 210 can include a housing 212 and a plurality of passages, lumens, or channels 214 for inserting and guiding one or more instruments. The plurality of channels 214 can be enclosed in another housing. The two housings can be connected. As is illustrated, the plurality of channels, such as radial channels, can be formed within a housing, which can be radially shaped. The plurality of channels 214 can also permit insertion of a camera lumen, cable, elongate shaft, or tube 224. As is illustrated, a distal end 224B of the camera tube can extend beyond the housing including the plurality of channels 214. At least a portion of the distal end 224B can be positioned near or in the site of interest. One or more cameras can be positioned at the distal end 224B. The camera tube 224 can also include a proximal end 224A as described herein. In some embodiments, a channel of the plurality of channels 214 can house or support a camera in addition to or instead of the one or more cameras of the camera tube 224.

Figure 2B:
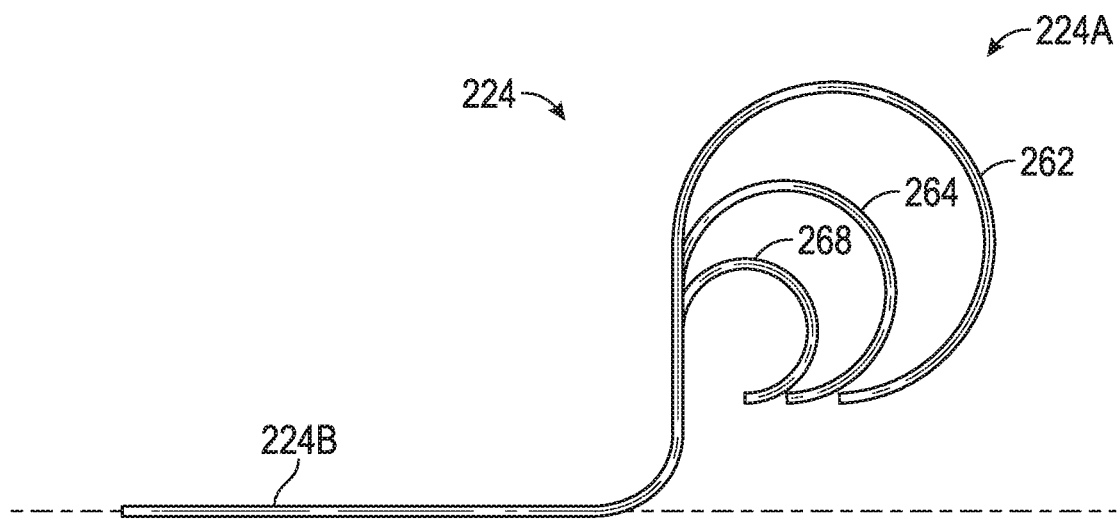

The visualization device can include a housing 222 to which the proximal end 224A of the camera tube can be removably (or non-removably) attached. The housing 222 can include an opening in which a one or more drivers, such as at least one of 232A or 232B, can be positioned. As described herein, the one or more drivers can move the camera tube 224 through the opening in the housing 222 and a channel of the plurality of channels 214 so that the distal end 224B extends away from one or more of the housings 212 or 222 or retracts back toward or into one or more of the housings 212 or 222. The camera tube 224 can form a loop around at least a portion of the housing 222 as illustrated in FIGS. 2A-2B. The diameter of the loop can be increased when the distal end 224B is retracted toward or into one or more of the housings 212 or 222 and be decreased when the distal end 224B is extended away from one or more of the housings 212 or 222. With reference to FIG. 2B, for example, when the distal end 224B is substantially fully retracted, the loop can have a diameter 262 as shown. When the distal end 224B is being extended away from the one or more of the housings 212 or 222, the diameter 264 of the loop decreases as compared to the diameter 264 of the loop. When the distal end 224B if fully extended away from the one or more of the housings 212 or 222, the diameter 268 of the loop can be smaller than the diameters 262 and 264. In some cases, extending the distal end 224B away from the one or more of the housings 212 or 222 causes the length of the proximal end 224A to decrease, which leads to a decrease in the diameter of the loop.

One or more cables 240 can be used to transmit control signals and data, such as analog or digital image data provided by the one or more cameras positioned at the distal end 224B or in the insertion device 210, to the patient cart 104. Control signals and data can be communicated to and from the electronic circuitry (for example, via the slave processor circuit 118 as described herein). One or more cables 240 can transmit power to the one or more cameras. One or more cables 240 can be plugged into a port positioned on the patient cart 104. In some cases, transmission can be wireless and one or more cables 240 may not be present.

At least a portion of the camera tube 224 can be flexible or substantially flexible in order to form a loop and/or be guided through the one or more openings and/or channels are described herein. In some cases, looping the camera tube 224 upward around at least the portion of the housing 222 as described can permit the camera tube to have sufficient length for reaching near and/or into the site of interest, while eliminating or reducing the risk of the camera tube 224 coming into contact with non-sterile object, such as the floor.

Insertion Device

Figure 3A:
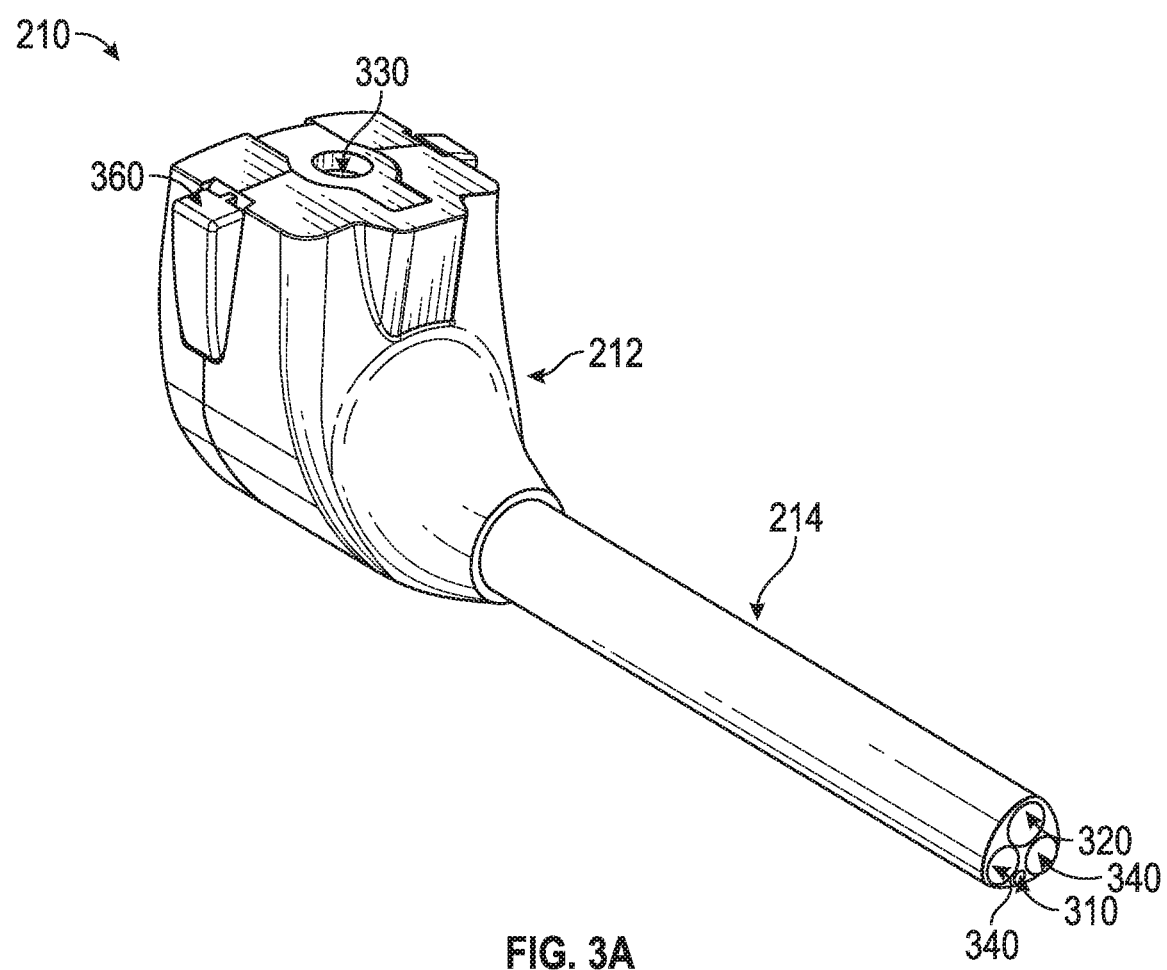
Figure 3B:
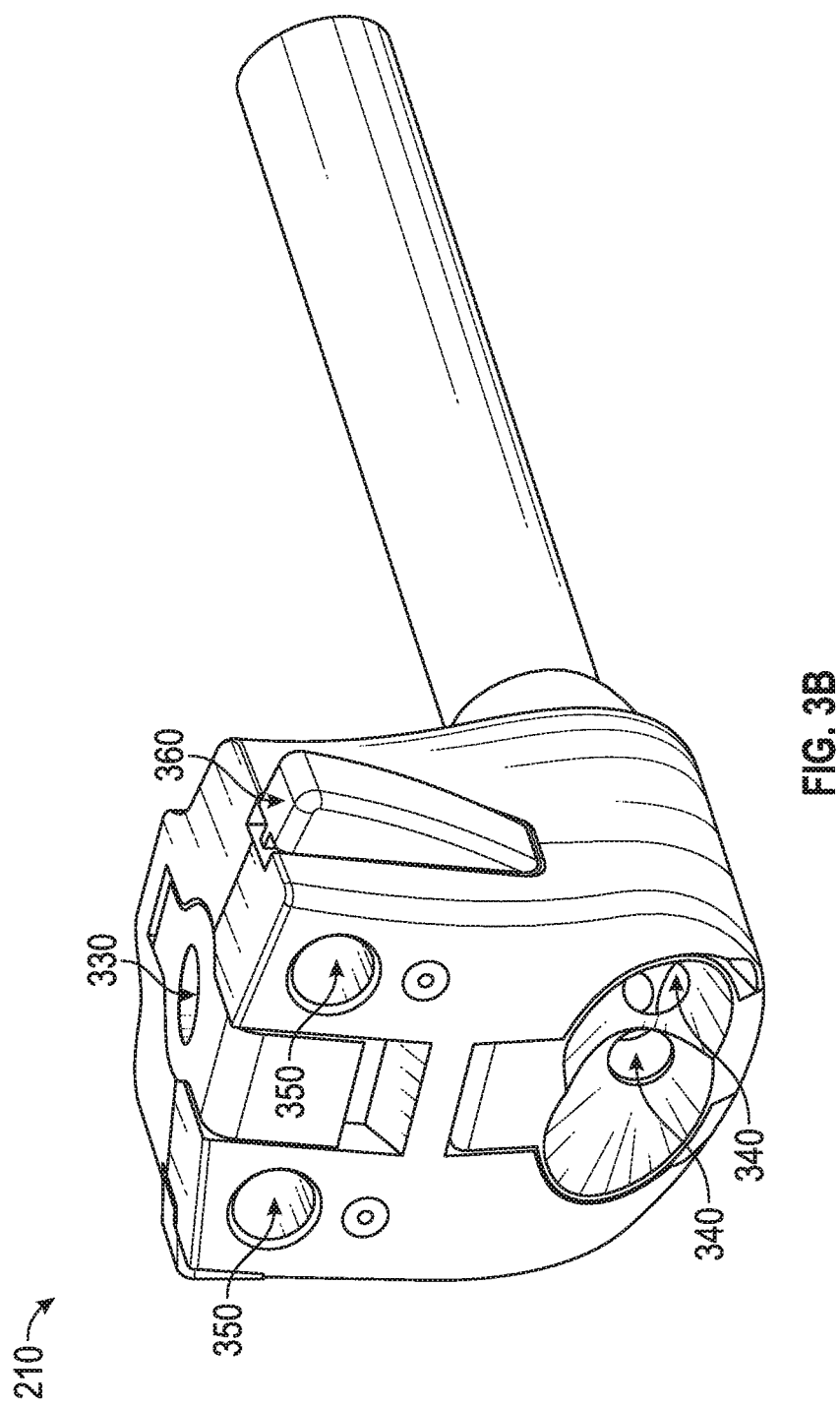

FIG. 3A illustrates a front perspective view of the insertion device 210 according to some embodiments. The housing 212 of the insertion device can include an opening 330 configured (for example, sized and/or shaped) to permit the camera tube 224 to pass through the housing 212. The opening 330 can include a seal, which may be covered by a closure (such as a latch), to prevent ingress of fluid, gas, or solids into the insertion device 210 and/or prevent backflow of fluid, gas, or solids from the insertion device. Any of the seals described herein can include one or more valves, such as a duckbill valve. As illustrated in FIG. 3E showing a cross-section view of the insertion device 210, the housing 212 can include an interior passage 322 connecting the opening 330 to a channel 320 configured (for example, sized and/or shaped) to permit the camera tube 224 to pass through the channel. The interior passage 322 can be a channel positioned in an interior of the housing. The interior passage 322 can be bent or curved to facilitate various positional configurations of the visualization device 220 with respect to the insertion device 210 and in particular the housing 222 with respect to housing 212. The interior passage 322 can include an opening that aligns with or includes the opening 300 and another opening that aligns with or includes opening of the channel 320. In some cases, sealing material can be used on or around the interior passage 322 in addition to or instead of the seal in the opening 330. As illustrated in FIG. 2A, the distal end 224B of the camera tube 224 can exit the channel 320 and extend away from the insertion device 210 toward a site of interest, such as a surgical site, body cavity, wound, or the like. Also, the distal end 224B of the camera tube 224 can retract toward or into the channel 320 toward the insertion device 210 and away from the site of interest.

The plurality of channels 214 can include one or more instrument channels 340 configured (for example, sized and/or shaped) to permit one or more instruments to pass through and extend away from the insertion device 210 toward the site of interest. As is illustrated, there can be two channels for left and right instruments.

In some cases, the interior passage 322 includes at least a portion with a central axis parallel to a central axis of the one or more instrument channels 340. The interior passage 322 can include at least a portion (for example, the curved portion illustrated in FIG. 3E) with a central axis not parallel to a central axis of the one or more instrument channels 340.

The plurality of channels 214 can include a channel 310 for one or more cameras of the insertion device 210. In some implementations, a camera can be positioned at a distal end of the plurality of channels (or at or near position of the arrow 310). Such one or more cameras (which can be referred to as a secondary camera) can facilitate positioning adjacent to or insertion into the site of interest of at least one of one or more instruments or at least one of the one or more cameras of the visualization device 220 (such cameras can be referred to as a primary camera, which can be endoscope or endoscopic cameras). The secondary camera can include a substantially flexible or substantially rigid lumen, cable, or elongate shaft that is inserted into the channel 310. The secondary camera can be integrated with the insertion device 210 or be removable. An opening of the channel 310 can include one or more seals, which may be covered by a closure (such as a latch), to prevent ingress of fluid, gas, or solids. In some cases, sealing material can be used on or around the opening of the channel 310 in addition to or instead of the seal(s) in the opening.

Figure 3D:
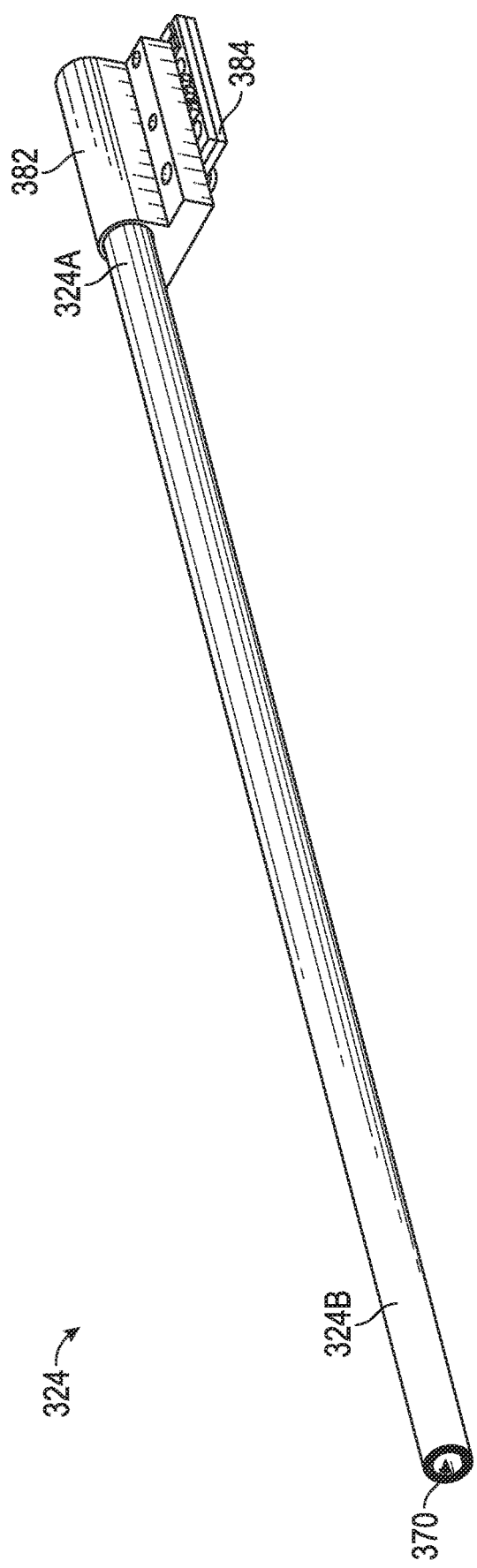
Figure 3E:
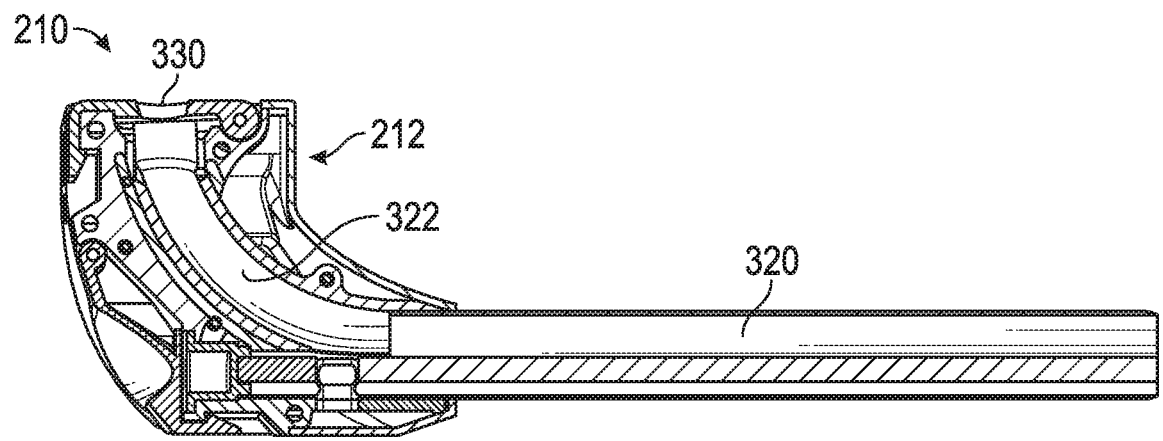

With reference to FIG. 3D, a secondary camera 324 can include a substantially flexible or rigid cable with a proximal end 324A and a distal end 324B. The distal end 324B can include a protector 370 (such as glass or plastic). The protector 370 can protect an imager and/or other components of the secondary camera breaking or malfunctions due to, for example, coming into contact with fluid in the site of interest. In other embodiments, a protector may be included as part of the insertion device 210 at a distal end of the channel 310, and accordingly the protector 370 may be optional. The secondary camera can include one or more lenses that focus light from and/or reflected by at least the portion of the site of interest on an image sensor 384. The image sensor can be positioned at the proximal end 324A and/or distal end 324B. The one or more lenses can include concave and/or convex lenses. In some cases, one or more lenses can be moved to adjust the zoom (such as, an optical zoom). The image sensor 384 can detect the light and convert it to image information or data. For instance, the image sensor 384 can measure brightness at a plurality of points. The image sensor 384 can include at least one of charge-coupled devices (CCDs), complementary metal-oxide-semiconductor (CMOS) image sensors, or the like. The image sensor 384 can be a digital and/or analog image sensor. In some implementations, the secondary camera can include two or more cameras (for example, to produce a stereoscopic image).

In some cases, the secondary camera 324 can include an optical system 382 that redirects the detected light. For example, the optical system 382 can be a prism that redirects the detected light down onto the image sensor 384. The image sensor 384 can be positioned in a different plane than a portion of the surgical site being imaged. The optical system 382 may be omitted in some implementations. For example, the optical system 382 may be omitted when the image sensor is positioned in the same plane as the surgical site being imaged.

The secondary camera 324 can be removable. For example, the secondary camera cable can be inserted into and/or removed from the channel 310. When the secondary camera cable is removed, the channel 310 can be used for one or more of suction or irrigation of the site of interest. The channel 310 can alternatively or additionally be used to permit an instrument (such as, third instrument) to be inserted. The instrument can be controlled by the robotic surgery system or manually by a user. A protector would not be included at a distal end of the channel 310 or would otherwise be removable when the channel 310 is used for one or more of aspiration, irrigation, instrument manipulation, or the like.

In some cases, the primary camera can be a stereo or stereoscopic camera, which can produce three-dimensional representation of at least a portion of the site of interest, and the secondary camera can be a two-dimensional camera. The secondary camera can have lower resolution than the primary camera. For example, the secondary camera can have 1920×1080 pixels (or 1080p) resolution. The primary camera can have resolution of 1080p, 4K, 8K, or the like. The channel 310 for the secondary camera can be smaller in size (such as, narrower or having smaller diameter) than the channel 320 for the primary camera. The secondary camera may also include an illumination source or device for illuminating the site of interest. The illumination device can be incorporated as part of the secondary camera such that the illumination device and a lens system of the secondary camera all fit within the diameter of the channel 310. In some cases, the illumination device can include optical fiber(s). For example, the illumination device can be an annular system with strands of fiber wrapping around a lens system so that illumination is provided to the site of interest, for instance, using known means of fiber illumination.

In some cases, close proximity of the instrument channels 340 to one or more camera channels 310 or 320 can facilitate single port surgery.

The housing 212 can include one or more attachment mechanisms 360. For example, the one or more attachment mechanisms 360 can be buttons positioned on opposite sides of the housing 212. The buttons can be configured to removably attach the insertion device 210 to a mounting interface of the drive unit 106 (or, in some cases, additionally or alternatively to the housing 222 of the visualization device 220). Pushing the buttons can release the insertion device 210 from the mounting interface (and/or the housing 222 of the visualization device 220). The one or more attachment mechanisms 360 can permit attachment to and release of the insertion device 210 from supporting pins of the mounting interface (and/or the housing 222).

FIG. 3B illustrates a rear perspective view of the insertion device 210 according to some embodiments. Openings of the one or more instrument channels 340 can include one or more seals, which may be covered by a closure (such as a latch), to prevent ingress of fluid, gas, or solids. In some cases, sealing material can be used on or around at least one of the one or more openings of the one or more instrument channels 340 in addition to or instead of the seal(s) in the one or more openings. The housing 212 can include one or more openings 350 for receiving one or more supporting rods of pins, which can be positioned on the mounting interface. The one or more attachment mechanisms 360 can permit attachment to and release of the insertion device 210 from the supporting pins (and/or from the visualization device 220). For example, the one or more attachment mechanisms 360 can activate or release a latch or lock, such as a cam lock, cam lock with a spring, or the like.

FIG. 3C illustrates a rear perspective view of the insertion device 210 showing seals 392 and 396 according to some embodiments. As described herein, the opening 330 (through which the camera tube 224 is inserted as described herein) can be covered by a seal 396 held in place by a closure 398, which can be a latch, clip, or the like. The seal 396 can prevent ingress of fluid, gas, or solids into the interior portion of the insertion device 210 and/or prevent backflow of fluid, gas, or solids from the insertion device 210. The seal 396 can include a valve, such as a duckbill valve. The closure 398 can be removably fastened to the housing 212 of the insertion device 210 in order to provide access to the seal 396, allowing the seal 396 to be cleaned and/or replaced during the same surgical procedure of between surgical procedures (such as, when the insertion device 210 is being cleaned and/or sterilized). The closure 398 can be removably fastened to the housing 212 by a protrusion or latch 397 of the closure 398 releasably engaging the bottom of a protrusion or projection 399 of the housing 212. In FIG. 3C, the closure 398 is illustrated in an open configuration or mode in order to show the seal 396. In operation, the seal 396 is inserted into the opening 330 and the closure 398 is fastened to the housing 212 in order to hold the seal 396 in place. FIG. 3B illustrates the closure 398 in a closed configuration.

One or more openings in the one or more instrument channels 340 through which the instruments are inserted can be covered by a seal 392 held in place by a closure 394, which can be a latch, clip, or the like. The seal 392 can prevent ingress of fluid, gas, or solids into the interior portion of the insertion device 210 and/or prevent backflow of fluid, gas, or solids from the insertion device 210. The closure 394 can be removably fastened to the housing 212 of the insertion device 210 similarly to the closure 398. The closure 394 can provide access to the seal 392, which can be removed and/or replaced during the same surgical procedure of between surgical procedures (such as, when the insertion device 210 is being cleaned and/or sterilized). In FIG. 3C, the closure 394 is illustrated in an open configuration or mode in order to show the seal 392. In operation, the seal 392 is inserted into the one or more openings of the one or more instrument channels 340 (see FIG. 3K) and the closure 394 is fastened to the housing 212 in order to hold the seal 392 in place. FIG. 3B illustrates the closures 394 in a closed configuration. One or more of the seals 392, 396 or the closures 394, 398 can be disposable and/or replaceable.

As illustrated in FIGS. 3B and 3C, the closure 398 includes an opening that coincides with the opening 330, and the closure 394 includes one or more openings that coincide with the one or more openings in the one or more instrument channels 340.

Figure 3F:
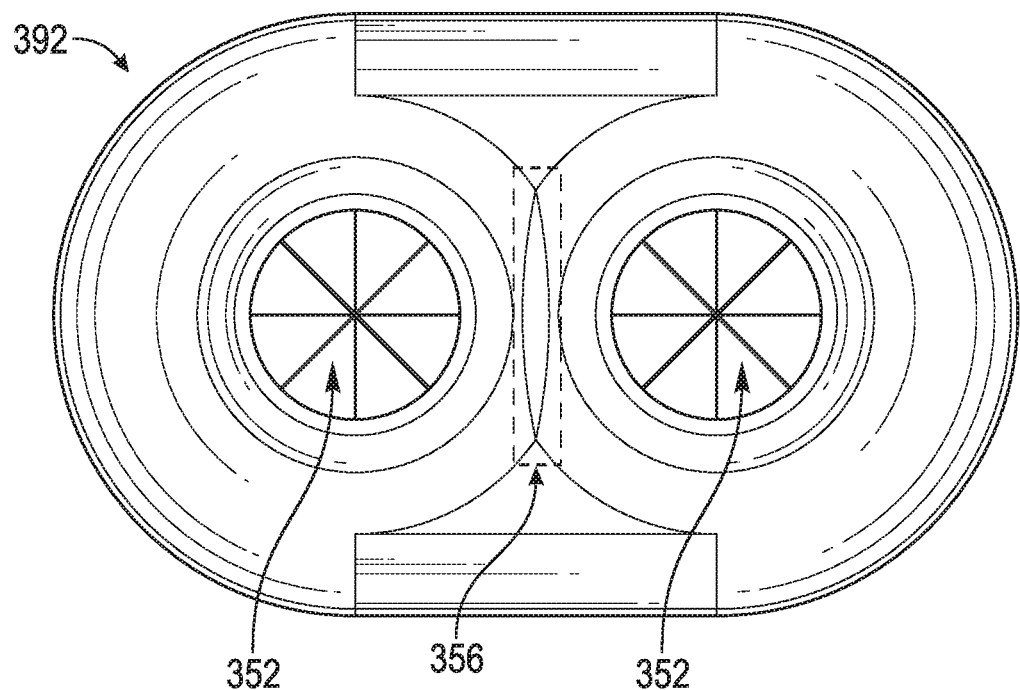
FIGS. 3F-3H illustrate a seal of an insertion device according to some embodiments.
Figure 3G:
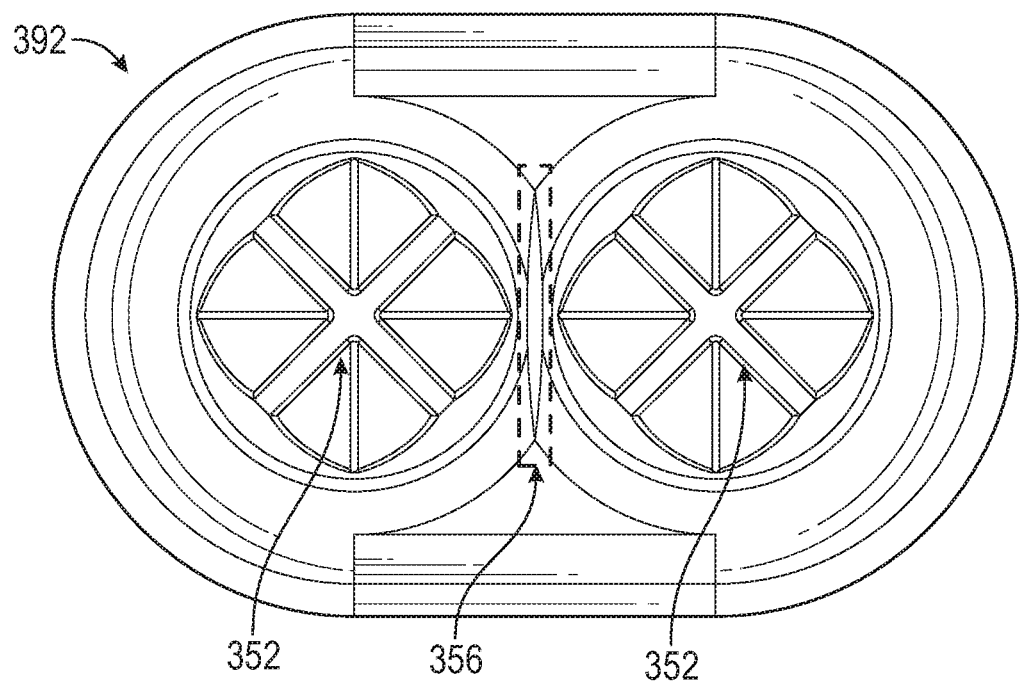
Figure 3H:
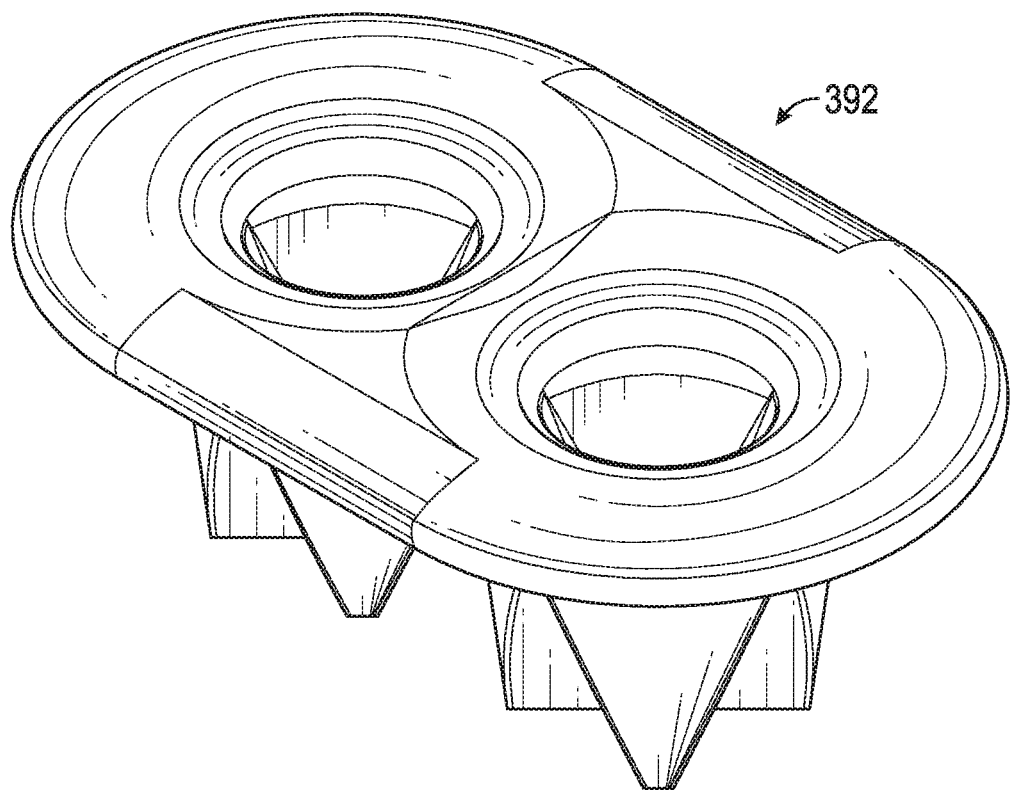

In some cases, as illustrated in FIG. 3C, a single seal 392 can cover both openings of the one or more instrument channels 340. Although it this can be preferable to using separate seals because of the close positioning of the one or more openings of the one or more instrument channels 340 relative to one another, in some instances, the seal 392 can include a plurality of separate seals. As illustrated in FIGS. 3F (top view), 3G (bottom view view), and 3H (perspective view), the single seal 392 can include two ports which are sized and shaped to cover the one or more openings in the one or more instrument channels 340. The ports 352 can include openings in the body of the seal 392 and protruding portions. For example, the ports 352 can be valves, such as duckbill valves, as shown in FIGS. 3F-3H. Each of the ports 352 can be shaped as a funnel (as described herein), which can facilitate insertion of the instruments.

Figure 3I:
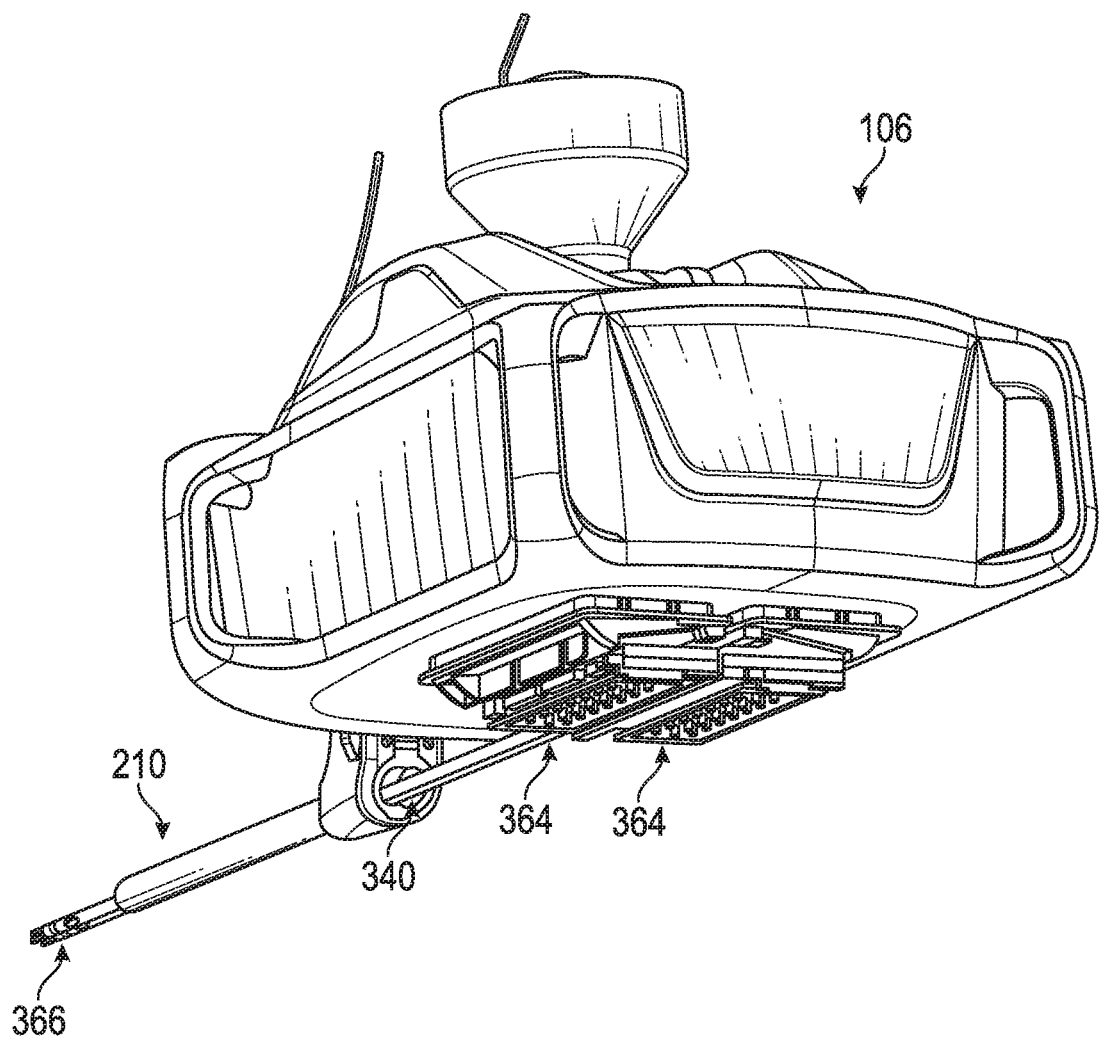
FIG. 3I illustrates a rear view of a drive unit of a robotic surgery system according to some embodiments.

In some cases, due to the proximity of the one or more openings of the one or more instrument channels 340 to each other, the ports 352 of the single seal 392 can also positioned close to each other. Such close proximity can cause the ports 352 to at least partially overlap as illustrated by a region 356 in FIGS. 3F (top/rear view) and 3G (bottom/front view). The ports 352 can at least partially overlap on one or more of top surface of the single seal 392 (FIG. 3F) or bottom surface of the single seal 392 (FIG. 3G), which faces the one or more openings of the one or more instrument channels 340. For example, as illustrated in FIGS. 3F-3H, a port 352 can have a concave shape (or funnel shape) that tapers from a distal end toward a distal end that is positioned distal to and/or is inserted into an opening of the one or more instrument channels 340. As shown in FIGS. 3F-3H, the proximal ends of the ports 352 can overlap (on one or more of top or bottom surfaces of the single seal 392) in the region 356. For instance, the proximal ends of the ports can be circular or round, and the circles can overlap in the region 356, as illustrated in FIGS. 3F-3H. In some cases, the overlap can be smaller or larger than that illustrated in the region 356. In some instances, the ports 352 do not overlap. FIG. 3I illustrates a rear view of the drive unit 106 showing loading of one or more instruments 364 into the insertion device 210. Loading of an instrument 364 can involve inserting a tip 366 of the instrument into an opening of a corresponding instrument channel 340. As is illustrated, a user may experience difficulties with the insertion of an instrument due to, among others, close proximity of the openings of the one or more instrument channels 340 to each other, having to facilitate the insertion through the rear of the drive unit 106 where light may be lacking, or the like.

Figure 3J:
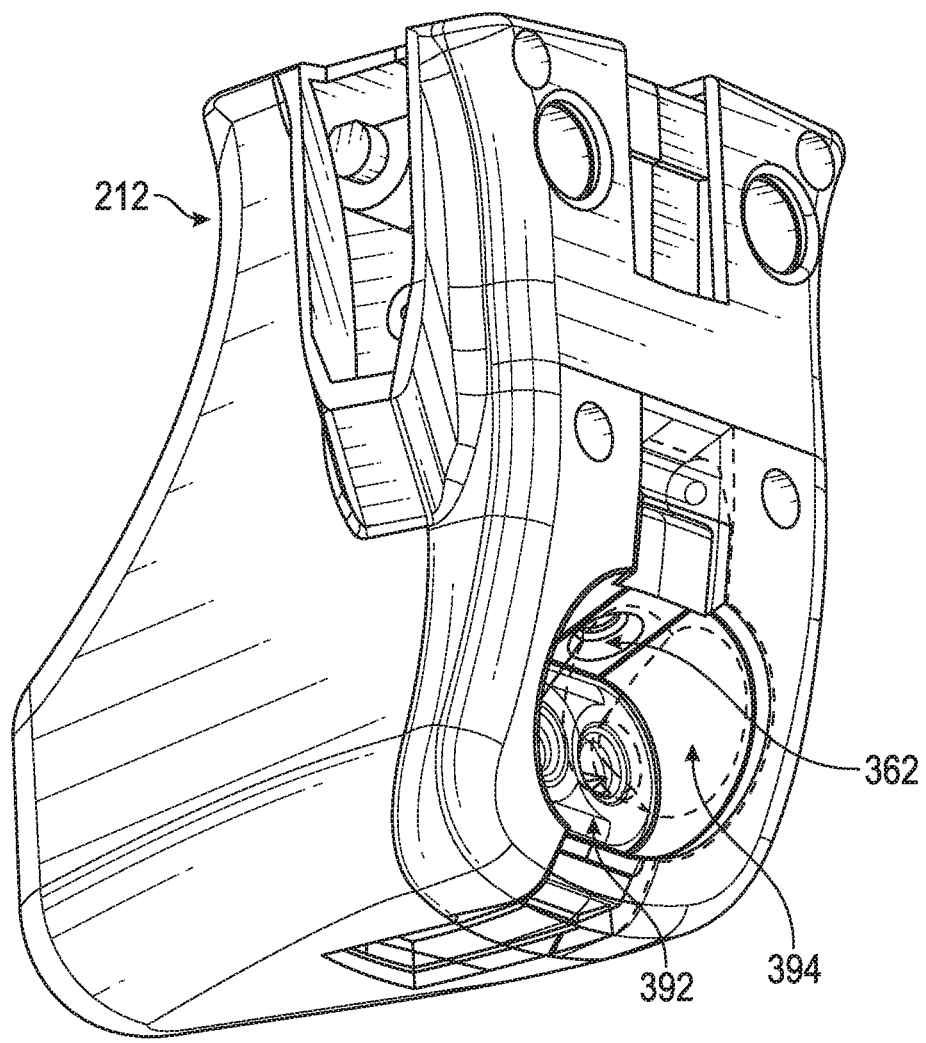
FIGS. 3J-3K illustrate rear views of an insertion device according to some embodiments.

To facilitate insertion of the one or more instruments, one or more openings in the one or more instrument channels 340 can be illuminated. Referring to FIG. 3J, which illustrates a rear view of the insertion device 210, in some cases, an illumination device 362 can be supported by the housing 212. The illumination device 362 can be positioned in a recess in the housing 212. For example, the illumination device 362 can be positioned in a recess 365 shown in the cross-sectional view of the housing 212 illustrated in FIG. 3K. The illumination device can 362 can include one or more light sources, such as one or more light emitting diodes (LEDs) or optical fibers (combined with a remotely located light source), that emit light. In some cases, the illumination device 362 can illuminate one or more of opening(s) in the closure 394, one or more ports 352 in the seal 392, or one or more of the openings in the one or more instrument channels 340. Such illumination can facilitate insertion of one or more instruments into the insertion device 210. The one or more light sources can be covered by one or more of a protective cover, lens (which can also serve as a protective cover), or the like.

FIG. 3J illustrates the illumination device 362 positioned above one or more openings of the one or more instrument channels 340. In some instances, the illumination device 362 can be positioned on the bottom, on a side, or the like on the rear of the housing 212. In some cases, multiple illumination devices can be supported by the housing 212. Such multiple illumination devices can be positioned on same or different sides of the rear of the housing 212. For example, two illumination devices can each be positioned above a respective instrument channel opening. In some cases, an illumination device can be positioned at the opening of an instrument channel 340 or inside the instrument channel 340.

Figure 3K:
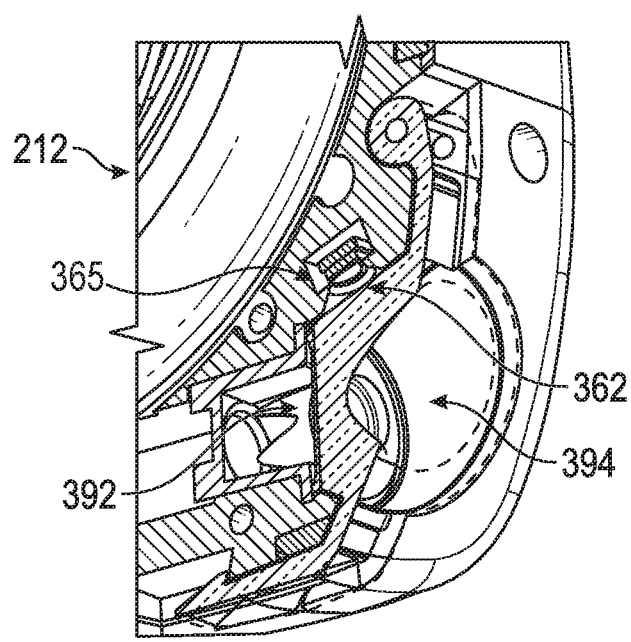

In some cases, the closure 394 can be made at least partially from transparent or substantially transparent material so that light emitted by the illumination device 362 passes through the closure 394 and illuminates the one or more openings of the one or more instrument channels 340. In some cases, the closure 394 can at least partially cover the illumination device 362 (as shown in FIGS. 3J-3K). Alternatively or additionally, the closure 394 can include an opening or recess so that the illumination device 362 is at least partially not covered by the closure 394 so that at least some of the emitted light does not pass through the closure 394. FIG. 3J illustrates a transparent or substantially transparent closure 394 as the seal 392 is visible through the closure. In some cases, the illumination device 362 may include a plurality of illumination devices or be shaped to contact a larger area of the closure 394.

As described herein, the illumination device 362 can include one or more light sources, such as LEDs. In some cases, the illumination device 362 can alternatively or additionally utilize one or more light sources already present in or incorporated into the insertion device 210, such as the illumination source of the secondary camera (as described herein), and/or the visualization device 220, such as the illumination source of the primary camera (as described herein), The insertion device 210 and/or the visualization device 220 can receive light from one or more external light source(s), such as from the patient cart 104 via one or more cables illustrated in FIGS. 1A-1B, or light source(s) internal to the insertion device 210 and/or the visualization device 220.

In some cases, an illumination device (not shown) can be used to similarly illuminate any of the openings disclosed herein, such as 330, 410, 412, or the like.

With reference to FIGS. 3B-3C, the closure 394 can be shaped as a funnel to facilitate insertion of the one or more instruments. The closure 394 can have a larger opening that is proximal from the one or more openings of the one or more instrument channels 340 than the one or more distal openings. The closure 394 can be shaped to taper from the proximal to the one or more distal openings, facilitating directing or guiding one or more instruments into the one or more openings of the one or more instrument channels 340.

Visualization Device

Figure 4A:
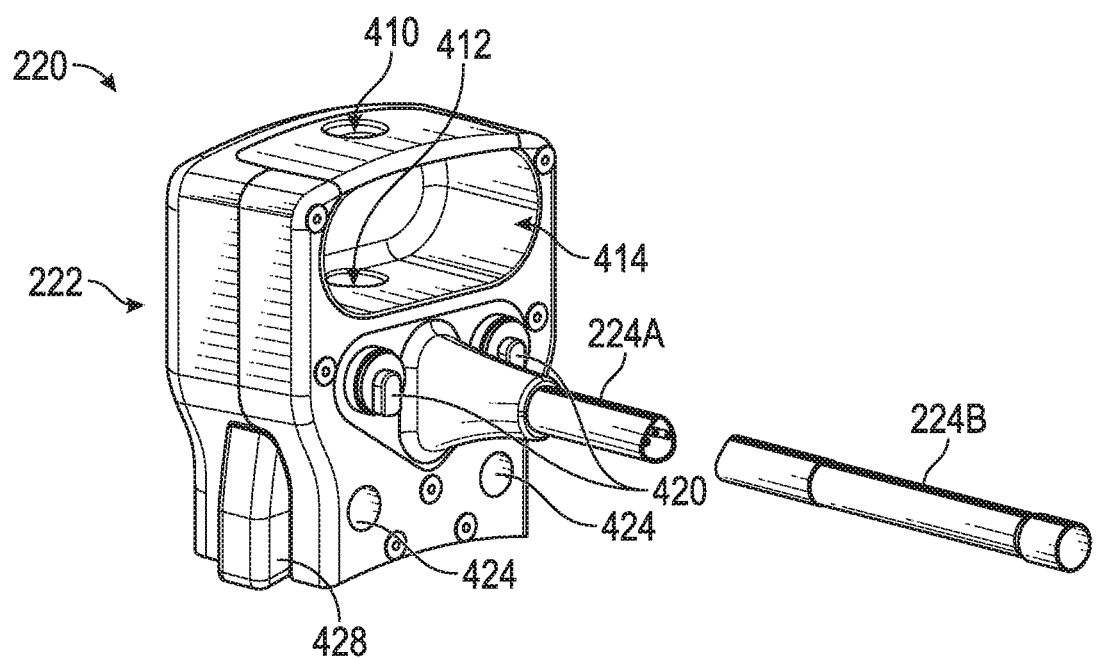
FIGS. 4A-4C illustrate a visualization device according to some embodiments.

FIG. 4A illustrates a front perspective view of the visualization device 220 according to some embodiments. The housing 222 of the visualization device can include openings 410 and 412 configured (for example, sized and/or shaped) to permit the camera tube 224 to pass through. As illustrated, the proximal end 224A of the camera tube 224 (illustrated for convenience without a middle portion) can be attached to the housing. The camera tube 224 can loop around at least the portion of the housing 222 when the distal end 224B is inserted through one or more of the openings 410 and 412 (see FIG. 2A). The openings 410 and 412 can be aligned to permit the camera tube 224 to pass through. A bottom opening (not illustrated) aligned with the opening 412 can be positioned on the bottom of the housing 222 to permit the camera tube 224 to exit the housing 222 after passing through an interior portion of the housing (such as, the interior portion illustrated in FIG. 4C). This bottom opening can be positioned adjacent to (such as over or on top of) the opening 330 in the housing of the insertion device 210 when the visualization device 220 is positioned adjacent to and/or attached to the insertion device. One or more of the openings 410, 412, or the bottom opening can include a seal, which may be covered by a closure (such as a latch) as described herein.

The housing 222 can include a drive opening 414. The drive opening can be positioned on a side of the housing 222 (for example, the back of the housing) that attaches to the mounting interface of the drive unit 106 as described herein. The drive opening 414 can be configured (for example, sized and/or shaped) to receive one or more drivers (at least one of 232A or 232B), such as a plurality of drive rollers as described herein (see, for example, FIG. 2A). With reference to FIG. 2A, the plurality of drive rollers can include right drive roller 232A and left drive roller 232B (collectively, referred to as 232). When inserted through the opening 410, the camera tube 224 is positioned between the right and left drive rollers 232A and 232B and contacts the drive rollers. The drive rollers 232 can contact, grip, or abut the camera tube 224. The drive rollers can advance the camera tube 224 down or retract it up through the drive opening 414. Movement of the drive rollers 232 in a first direction can advance the camera tube 224 forward or down through the drive opening 414 in order to advance the distal end 224B toward the site of interest. For example, the right driver roller 232A can spin counterclockwise and the left drive roller 232B can spin clockwise in order to advance the camera tube 224 forward. Such combination of the counterclockwise and clockwise movement of the drive rollers can constitute the first direction. Movement of the drive rollers 232 in a second direction can retract the camera tube 224 backward or up through the drive opening 414 in order to retract the distal end 224B away from the site of interest. For example, the right drive roller 232A can spin clockwise and the left drive roller 232B can spin counterclockwise in order to retract the camera tube 224 backward. Such combination of the clockwise and counterclockwise movement of the drive rollers can constitute the first direction. For each of the right and left drive rollers, movement in the second direction can be opposite to movement in the first direction even in cases where drive rollers spin in opposite directions during movement in the first and/or section direction.

Drive rollers 232 can have an external surface that is made out of and/or is covered by soft material, such as rubber, foam, or the like, that grips an external surface of the camera tube 224 in order to one or more of advance or retract the camera tube. In some embodiments, a portion of the camera tube 224 positioned between the drive rollers 232 can slip along the drive rollers, and as a result the camera tube would not be advanced or retracted. For example, slipping can be advantageous when a user's limb becomes caught in the loop formed by the camera tube 224 or in case of malfunction to prevent or lessen the risk of injury to the user or damage to one or more of the camera tube 224, the visualization device 220, the insertion device 210, or any other part of the system 100. At least one of one or more of the material on the external surface of the drive rollers 232 or on an external surface of the camera tube 224 or a surface pattern on the surface of one or more of the external surface of the drive rollers 232 or the external surface of the camera tube 224 can be selected to have a friction coefficient that results in slippage in case force on the camera tube exceeds a maximum force, such as, a maximum frictional force. The maximum frictional force can depend on one or more of the friction coefficient between the drive rollers 232 and camera tube 224 or a clamping force between the drive rollers 232 and camera tube 224. In some cases, the maximum frictional force can be 5N or less or more, 7N or less or more, 10N or less or more, or the like. Surface pattern on the external surface of the drive rollers 232 (and/or the external surface of the camera tube 224) can affect the friction coefficient. For example, ribbed surface pattern, toothed surface pattern, or the like can increase the friction coefficient compared to a smooth or substantially smooth surface pattern.

At least a portion of the distal end 224B of the camera tube 224 can articulate to permit viewing of at least a portion of the site of interest. The housing 222 can include one or more actuators 420 configured to control movement of the distal end 224B of the camera tube 224, which can include one or more cameras. In some cases, a first actuator can control pitch or tilt (up/down movement) of the distal end 224B, and a second actuator can control yaw or pan (left/right movement) of the distal end 224B. The first and second actuators can control movement of the distal end 224B by manipulating links positioned in the interior of the camera tube 224 as described herein (for example, with reference to FIGS. 4B-4C).

The housing 222 can include one or more attachment mechanisms 428. For example, the one or more attachment mechanisms 428 can be buttons positioned on opposite sides of the housing 222. The buttons can be configured to removably attach the visualization device 220 to the mounting interface of the drive unit 106 (or, in some cases, additionally or alternatively to the housing 212 of the insertion device 210). Pushing the buttons can release the insertion device 210 from the mounting interface (and/or the housing 212). The one or more attachment mechanisms 428 can permit attachment to and release of the visualization device 220 from one or more supporting rods or pins (and/or the housing 212). As described herein, the one or more attachment mechanisms 428 can activate or release a lock, such as a cam lock, cam lock with spring, or the like. The housing 222 can include one or more openings 424 for receiving one or more the supporting pins that can be positioned on the mounting interface.

Figure 4B:
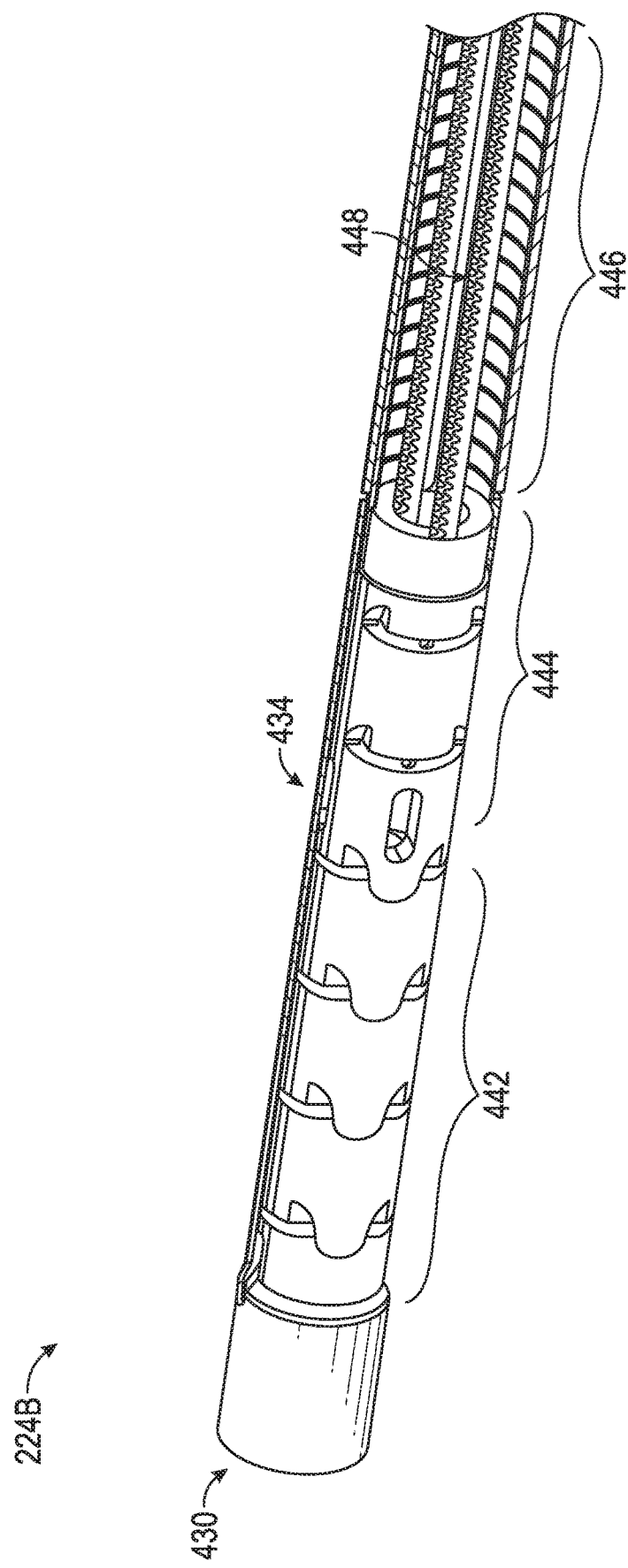

FIG. 4B illustrates a perspective view of the distal end 224B of the camera tube 224 according to some embodiments. An imager 430 (which can be the primary camera) with one or more cameras can be positioned at or near the tip of the distal end 224B. The distal end 224B can include a pitch or tilt segment or section 442 for controlling up/down movement of the distal end 224B, and a yaw or pan segment section 444 for controlling left/right movement of the distal end 224B. As illustrated, the tilt section 442 can be positioned adjacent the imager 430, and the pan section 444 can be positioned adjacent to the tilt section. Pan section 444 can be positioned farther away from the tip of the distal end 224B than the tilt section 442. In some cases, positioning of the sections 442 and 444 relative to the tip can be reversed. In some cases, the sections 442 and 444 can be intermingled with respective couplings or guides (as described below) of the sections 442 and 444 alternating.

At least one of sections 442 or 444 can include one or more couplings or guides 434. The one or more couplings 434 can be coupled to each other to allow bending of the distal end 224B. The sections 442 and 444 can bend (as described herein) as a result of at least one of pulling or pushing one or more flexible or substantially flexible links 448 positioned in the interior of the camera tube 224 that control, for example, the bend, curvature, or another aspect of spatial orientation of one or more of sections 442 or 444. One or more links 448 can include a wire, cable, or the like with elasticity that can support at least one of tension or compression without permanent deformation. One or more links 448 can be connected to the one or more guides 434 (for example, by being connected to the one or more guides in the interior of the camera tube 224). Movement, such as pulling and/or pushing, of the one or more links 448 can cause adjustment of the spatial orientation of the one or more guides 434 and, as a result, one or more sections 442 or 444.

As described herein, one or more actuators 420 can pull and/or push the one or more links 448, for example, via rotation in first and/or second directions. Pulling a link 448 can cause shortening its length, while pushing the link can cause lengthening the link (such as, returning the link substantially to its initial length).

Segment or section 446 can be positioned adjacent the pan section 444 at the distal end 224B of the camera tube 224. As described herein, section 446 can be flexible or substantially flexible. One or more of sections 442 or 444 can be rigid or substantially rigid to prevent at least the imager 430 of the distal end 224B from drooping or sagging as the distal end 224B exits the channel 320 of the insertion device. Drooping or sagging can undesirably lead to at least a temporary loss of vision of at least a part of the site of interest or inadvertent contact with tissue near or outside the site of interest. Rigidity of the one or more sections 442 or 444 can prevent movement of the distal end 224B in a downward direction (for example, in the absence of actively tilting the camera tube 224 as described herein), while permitting movement in the opposite direction as the camera tube 224 is passed through one or more openings or channels, as described herein. Rigidity can help maintain orientation of at least the imager 430 in same plane of the channel 320 or in a plane above the plane of the channel 320 as the distal end 224B of the camera tube 224 exits the channel 320. The latter plane can be parallel or substantially parallel to the plane of the channel 320.

In some cases, to increase the rigidity of the distal end 224B, a supporting material or mechanism may be added to the distal end 224B to help maintain orientation of at least the imager 430 in the same plane of the channel 320. Such design can prevent the camera from drooping and/or contacting unwanted areas of the site of interest. The supporting material or mechanism can allow the distal end 224B to flex (or curve) in one direction in a plane while preventing other flexing (or curving), thereby allowing the distal end 224B to move through a curved portion of the interior passage 322 of the housing 212. With reference to FIG. 3E, for instance, flexing in the direction of the bend or curve of the interior passage 322 can be permitted, while flexing in the other direction may not be permitted.

Figure 4C:
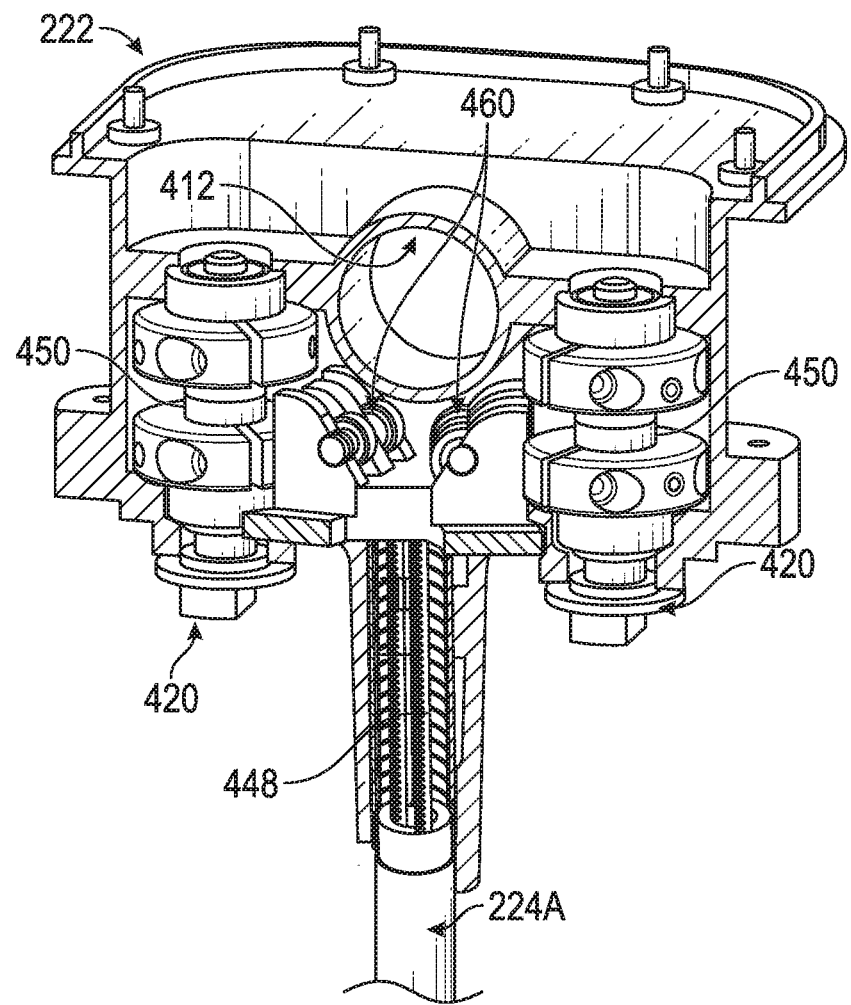

FIG. 4C illustrates a cross-sectional view of the housing 222 and camera tube 224 of the visualization device 220 according to some embodiments. The figure depicts view of an interior portion of the housing 222 looking up through the opening 412 in the housing 222. Proximal end 224A of the camera tube 224 can be attached to the housing 222 as described herein. As illustrated, interior of the proximal end 224A can include one or more links 448 that extend along the length of the camera tube 224 to the distal end 224B, as described herein. In use, the camera tube 224 passes through the interior portion illustrated in FIG. 4C.

The one or more actuators 420 can include first and second actuators that, respectively, control tilting or panning of the distal end 224B of the camera tube 224. For example, the first actuator can control pulling and/or pushing of one or more links 448 connected to a plurality of guides in the tilt section 442. The first actuator can control tilting up/down of at least the imager 430. The second actuator can control pulling and/or pushing of one or more links 448 connected to a plurality of guides in the pan section 444. The second actuator can control left/right movement of at least one of the tilt section 442 and/or the imager 430.

Pulling and/or pushing at least one link 448 can be performed via actuating the first and/or second actuator 420. With reference to the first actuator, for instance, its exterior portion that protrudes from the housing 222 can serve as a shaft connected to a drum 450 located in the interior of the housing 222. Rotation of the shaft and drum can cause a corresponding link pulley 460 to rotate, for example, in a plane perpendicular to the plan of rotation of the shaft and drum. The pulley 460 can be connected to the drum 450 such that rotation of the drum causes the pulley to rotate. The drum 450 can have threading on the surface that contact threading on the surface of the pulley 460 and transfers rotation to the pulley. The pulley 460 can be connected to at least one link 448. For instance, the at least one link can be attached to the pulley. Rotation of the actuator 420 in a first direction (for example, clockwise) can cause rotation of the corresponding shaft (for example, in the same clockwise direction). This can cause the corresponding pulley 460 to rotate and, for instance, pull (or push) the associated at least one link, which can cause tilting of at least the imager 430. In some cases, the pulley 460 can be connected to a pair of links 448 one of which is pulled while the other is pushed to control the tilting. Second actuator can operate similarly to control the panning.

Additional details of controlling one or more of the tilt or pan of the distal end 224B of the camera tube are similar to those described in U.S. Patent Publication No. 2016/0143633 and U.S. Pat. No. 9,629,688, which are assigned to the assignee of the present application and the disclosure of each of which is incorporated by reference in its entirety.

Mounting Interface and Sterile Barrier

Figure 5A:
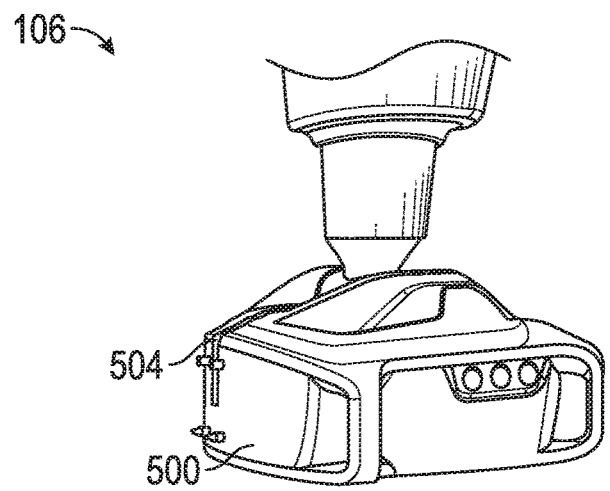
FIGS. 5A-5E illustrate a mounting interface of a drive unit of a robotic surgery system according to some embodiments.

FIG. 5A illustrates the drive unit 106 of the robotic surgery system 100 according to some embodiments. The drive unit 106 can include a mounting interface 500 configured to support one or more of the insertion device 210 or visualization device 220. The mounting interface can include an opening or slit 504 for receiving a looped portion of the camera tube 224 (see, for example, FIG. 6I).

Figure 5B:
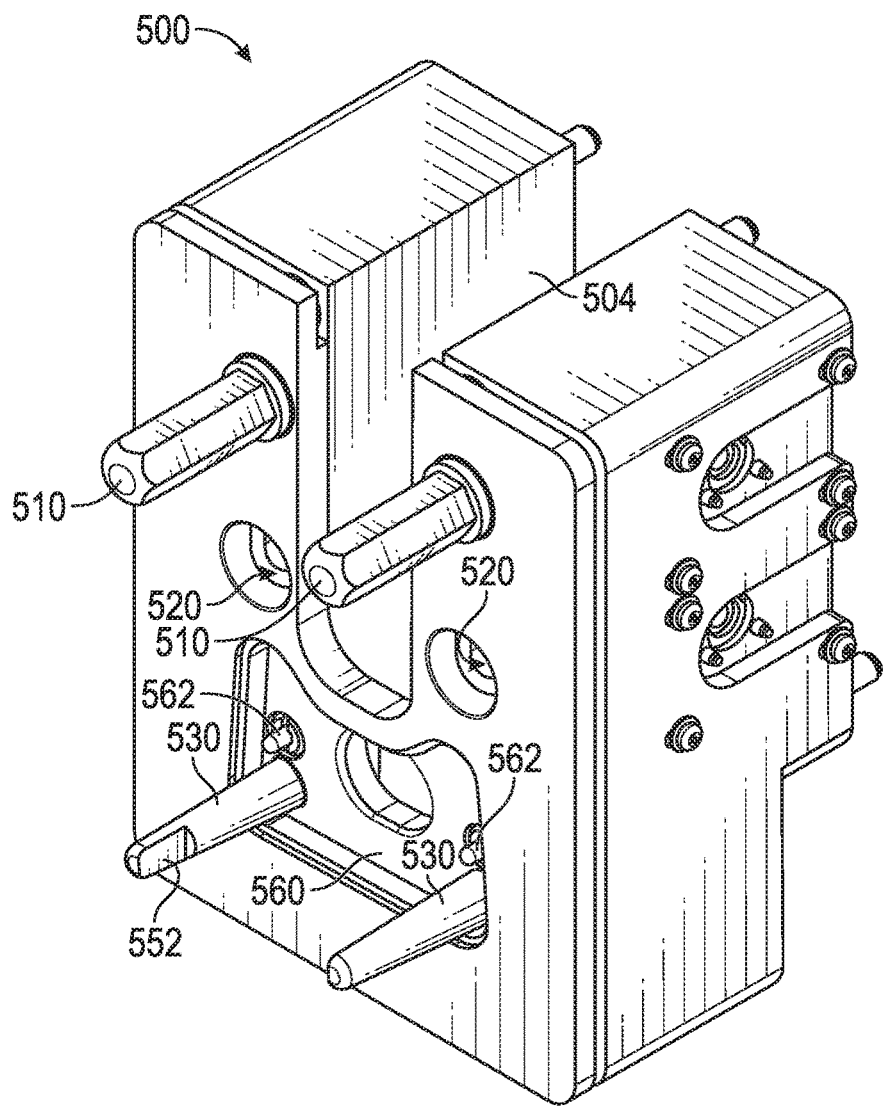

FIG. 5B illustrates a perspective view of the mounting interface 500 according to some embodiments. The mounting interface 500 can include one or more posts or pins 510 configured to actuate one or more drivers 232 for moving the camera tube 224 as described herein. As illustrated, the pins 510 can be provided to support the rollers 232A and 232B. The pins 510 can be configured (for example, sized and/or shaped) to attach to the rollers 232A and 232B. For example, the pins 510 can be hexagonal, and the rollers 232A and 232B can include hexagonal openings (see, for example, FIG. 5D) configured (for example, sized and/or shaped) to be mounted on the hexagonal surface of the pins 510. In some cases, one or more shapes such as square, round, triangular, or the like can be used in addition to or instead of hexagonal.

The mounting interface 500 can include one or more actuators 520 for causing movement of the one or more actuators 420 of the visualization device 220. As illustrated, two actuators 520 can be provided, and they can include shafts or recesses configured (for example, sized and/or shaped) to receive protruding exterior portions of the actuators 420. Within the recesses, the actuators 520 can include surfaces configured (for example, sized and/or shaped) to mate with the surfaces of the protruding exterior portions of the actuators 420. The mating can provide attachment of the actuators 420 of the visualization device 220 to the actuators 520 of the mounting interface 500.

As described herein, the mounting interface 500 can support one or more of the insertion device 210 or visualization device 220. As illustrated in FIG. 5B, the visualization device 220 can be at least partially supported by the pins 510 supporting the drivers 232 that are placed in the recess 414 of the housing 222. The mounting interface 500 can include one or more pins 530 configured to support the insertion device 210. The one or more pins 530 can be configured (for example, sized and/or shaped) to be received in the one or more openings 350 of the insertion device 210. The one or more pins can have size, shape, and/or surface pattern configured to be attached to insertion device 210. For example, as is illustrated, a left pin 530 can have a groove, pattern, or indentation 552 at or near its tip. The indentation 552 can be configured (for example, sized and/or shaped) to mate with a surface in the interior of the left opening 350 (see, for example, FIG. 3B. This can provide attachment of the insertion device 210 to the mounting interface 500. As described herein, one or more attachment mechanisms 360 can operate to disengage the visualization device 210 from the mounting interface 500. For example, one or more attachment mechanisms 360 can be pressed to disengage mating of the surface in the interior of the left opening 350 with the indentation 552. The right pin 530 can have a similar groove, pattern, or indentation 552 at its tip on the side facing the left pin.

Figure 5C:
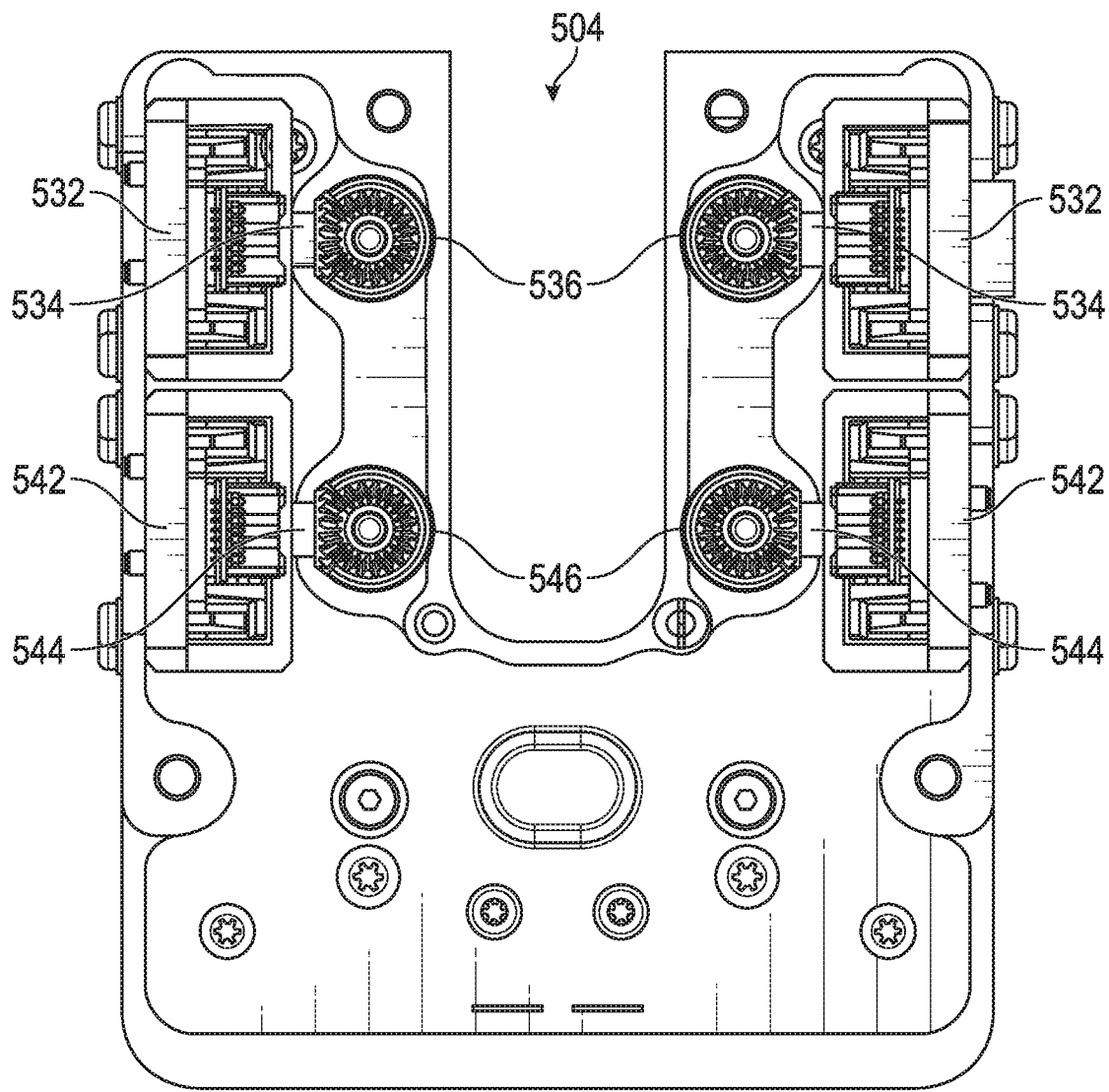

FIG. 5C illustrates a rear view of the mounting interface 500 according to some embodiments. The mounting interface can include a first set of actuators 532, a first set of gears 534 connected to or attached to the first set of actuators 532, and a second set of gears 536 cooperating with the first set of gears 534. These components can be collectively configured to actuate the one or more pins 510. As illustrated, the first set of actuators 532 can include two actuators, the first set of gears 534 can include two gears, and the second set of gears 536 can include two gears. In some cases, the first set of actuators can be motors, for example, electric motors.

The first set of gears 534 can interlock with the second set of gears 536. In some cases, the first set of actuators 532 can be configured to rotate the first set of gears 534 attached to the first set of actuators 532. Rotation of the first set of gears 534 can cause the second set of gears 536 to rotate in a plane perpendicular to the plane of rotation of the first set of gears 534. The one or more pins 510 can be connected or attached to the second set of gears 536. Rotation of the second set of gears 536 can cause rotation of the one or more pins 510. Rotation of the one or more pins 510 can cause rotation of the one or more drivers 232 and movement of the camera tube 224, as described herein. Rotation of the one or more pins 510 and one or more drivers 232 can be in the first and/or second direction to advance and/or retract the camera tube 224, as described herein. Rotation in the first and/or second direction can be caused by movement of the one or more actuators in at least two directions (for example, clockwise or counterclockwise).

The mounting interface 500 can include a second set of actuators 542, a third set of gears 544 connected to or attached to the second set of actuators 542, and a fourth set of gears 546 cooperating with the third set of gears 544. Collectively these components can be configured to actuate the one or more actuators 520. As illustrated, the second set of actuators 542 can include two actuators, the third set of gears 544 can include two gears, and the fourth set of gears 546 can include two gears. In some cases, the first set of actuators can be motors, for example, electric motors.

The second set of actuators 542, third set of gears 544, and fourth set of gears 546 can cooperate with each other and operate to actuate the one or more actuators 520 similarly to the foregoing description of actuating the one or more pins 510. As described herein, movement of the actuators 520 and corresponding movement of the actuators 420 of the visualization device 220 can cause the camera tube 224 to tilt and/or pan.

Figure 5D:
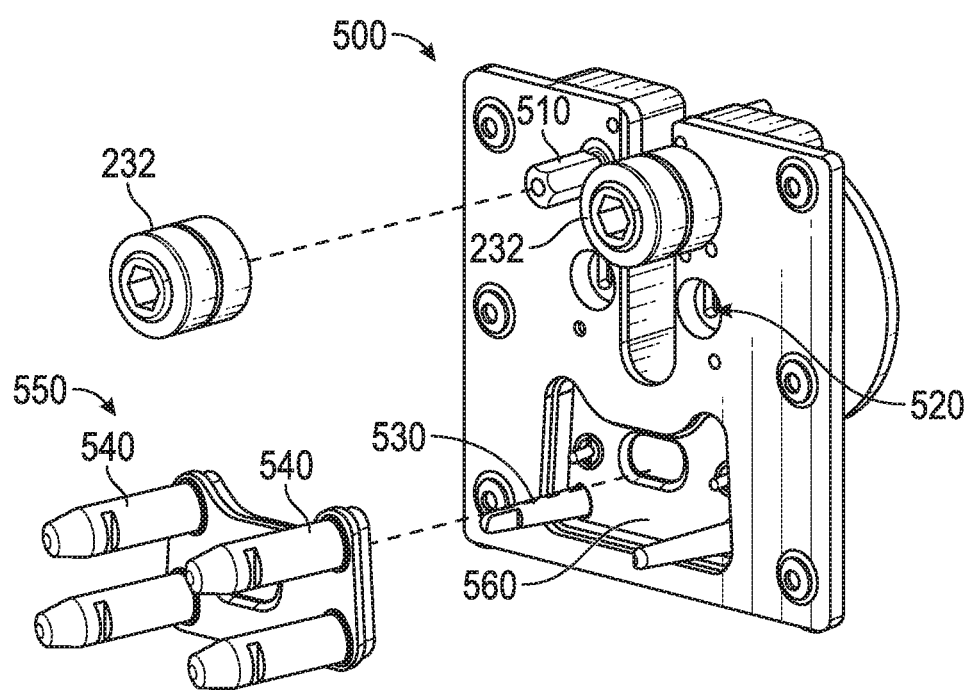

FIG. 5D illustrates the mounting interface 500 prepared for supporting one or more of the insertion device 210 or visualization device 220 according to some embodiments. In some implementations, a sterile barrier may need to be provided between the mounting interface 500 of non-sterile drive unit 106 and the insertion device 210 and/or sterile visualization device 220. The insertion and visualization devices, 210 and 220, may be required to be sterile in order to protect the site of interest from infection in case of one or more of the insertion or visualization device coming into contact with the site of interest or with another sterile component of the system 100 (such as, an instrument) that may come into contact with the site of interest, with a user performing or assisting with the surgery.

One or more drivers 232 (for example, rollers) can be sterile and can be attached to or mounted on the one or more pins 510 of non-sterile mounting interface 500. A sterile cover 550 can be attached to or mounted to cover the one or more pins 530. With reference to FIG. 5B, the cover 550 can be mounted in a region 560 on a front surface of the mounting interface 500. The cover 550 can be secured with one or more closures (not illustrated). For example, the one or more closures can be pins that are pushed in by the cover 550 when it is mounted in the region 560. Pushing of the pins can cause a closure, such as a latch, to become closed. The cover 550 can be removed from the region 560, for example, by pressing a button positioned on the bottom surface of the mounting interface 500 (not shown), which can push the pins against the cover 550 and dislodge the cover.

The cover 550 can include a bottom set of pin covers for covering the one or more pins 530. The cover 550 can include a top set of pins 540 that can be configured to support the visualization device 220 when it is attached to the mounting interface 500. The set of pins 540 can be sized and/or shaped to be received in the one or more openings 424 of the visualization device 220. The set of pins 540 can have size, shape, and/or surface shape configured to be attached to the visualization device 220, for example, as described herein in connection with the pins 530.

Figure 5E:
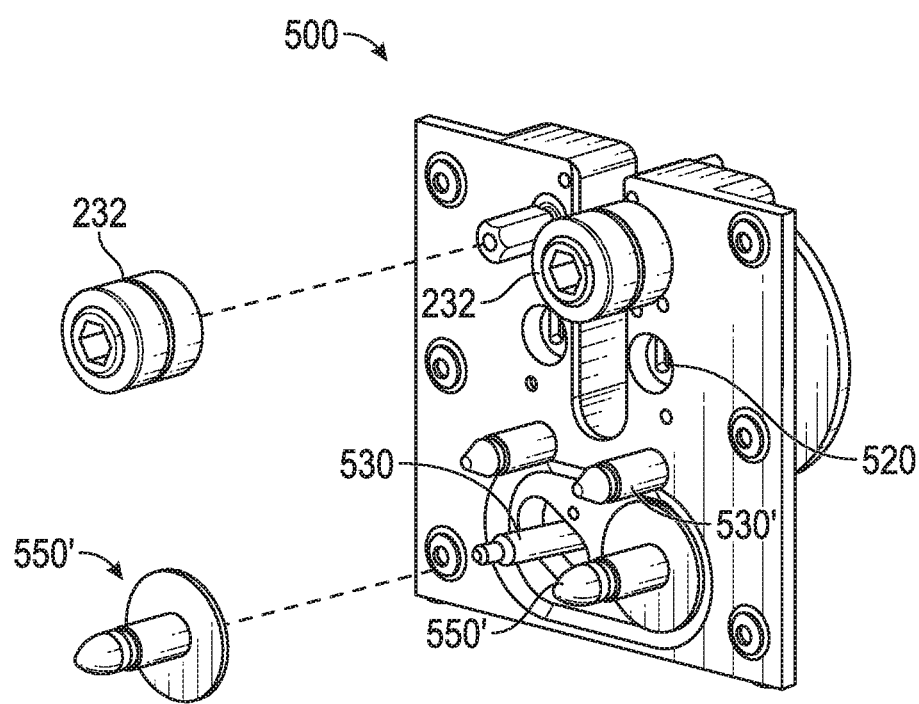

With reference to FIG. 5E, in some implementations, the mounting interface 500 can include one or more pins 530' configured (for example, sized and/or shaped) to support the visualization device 220. For example, the one or more pins 530' can function similar to the one or more pins 540. One or more pins 530' can be covered by the cover 550, such as by pin covers 540. In some cases, as illustrated in FIG. 5E, individual covers 550' can be used to cover each of the one or more pins 530 and/or 430'. In some embodiments, two separate covers can be used to cover the one or more pins 530 and 430' respectively. In some implementations, a single cover 550 (as illustrated in FIG. 5D) but with pin covers replacing the top set of pins 540 can be used to cover the one or more pins 530 and 530'.

In some cases, a sterile barrier can be formed between one or more actuators 420 of the visualization device (see, for example, FIG. 4A) and one or more actuators 520 of the mounting interface (see for example, FIG. 5B) in one or more of the following ways. One or more actuators 420 can be covered by one or more sterile covers as described herein. A sterile drape can be placed over the drive unit 106 and the mounting interface. Drape material can flex and/or slip to provide the sterile barrier. Drape material can have appropriate thickness and/or other properties to allow for the flexing and/or slippage. The drape can include one or more sterile covers (which can function as actuators) that transfer motion between the one or more actuators 420 and one or more actuators 520. The one or more sterile covers can be embedded or integrated into the drape.

The one or more drivers 232 and one or more covers 550 can serve as at least a partial sterile barrier between the mounting interface 500 and the insertion and visualization devices and the camera tube 224. Any one or more of the drivers 232, one or more of the covers 550, or any other sterile barriers disclosed herein can be disposable or can be reused after being sterilized. For example, the one or more sterile covers 550 can be made out of plastic and be disposable. As another example, rollers 232A and 232B can be disposable.

Any of the sterile components described herein can be sterilized by fluid or gas (such as ethylene oxide (EtO)), heat (such as autoclaving), irradiation (such as gamma irradiation), or the like. For example, the one or more openings in the insertion device 210 and/or visualization device 220 can facilitate fluid or gas to contact exterior and interior surfaces during sterilization.

Docking the Insertion and Visualization Devices

Figure 6C:
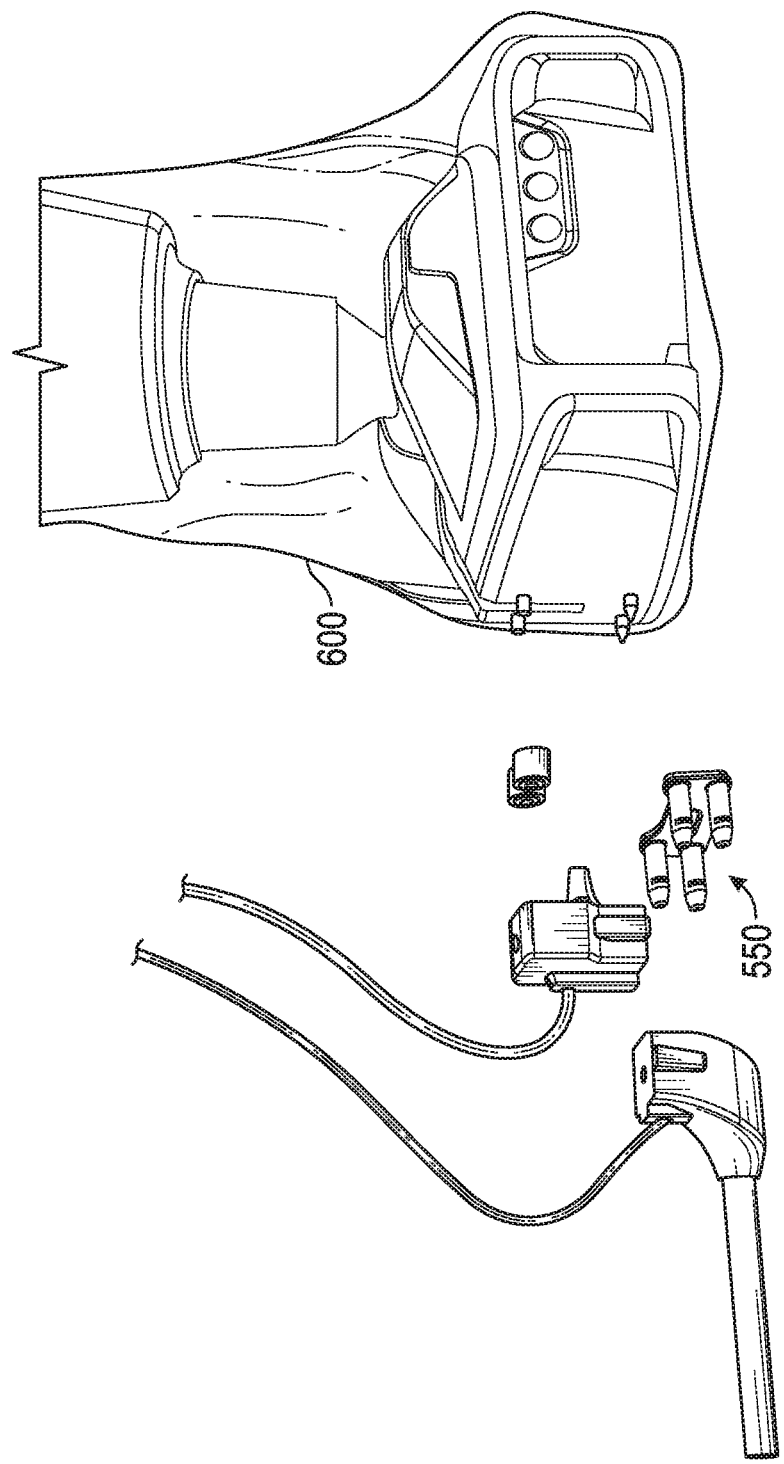

FIG. 6A illustrates the insertion device 210, visualization device 220, one or more covers 550, drivers (such as rollers) 232A and 232B, and the mounting interface 500 of the drive unit 106 according to some embodiments. As illustrated in FIG. 6B, a sterile drape 600 can be placed over drive unit 106 (and, in some cases, other parts of the robotic surgery system) to provide additional or alternative sterile barrier. For example, the drape 600 can act as a sterile barrier permitting a user performing or assisting with the surgery to touch the drive unit 106. One or more holes 610 can be made in the drape 600 to permit one or more pins 510, 530, and/or 540 or 530' to be accessed. Positions and sizes of the one or more holes 610 can correspond to positions and sizes of the one or more pins. The drape 600 can be pulled tight around the drive unit 106 and other components of the system 100 as illustrated in FIG. 6C. The drape 600 can be held in place with one or more of ties, adhesive attachments, magnetic attachments, or the like.

Figure 6E:
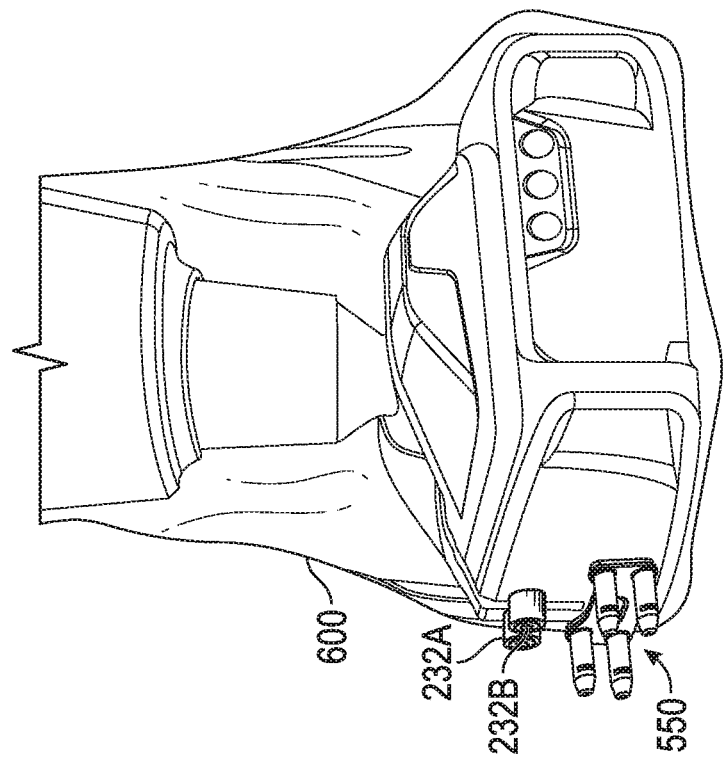
Figure 6E:
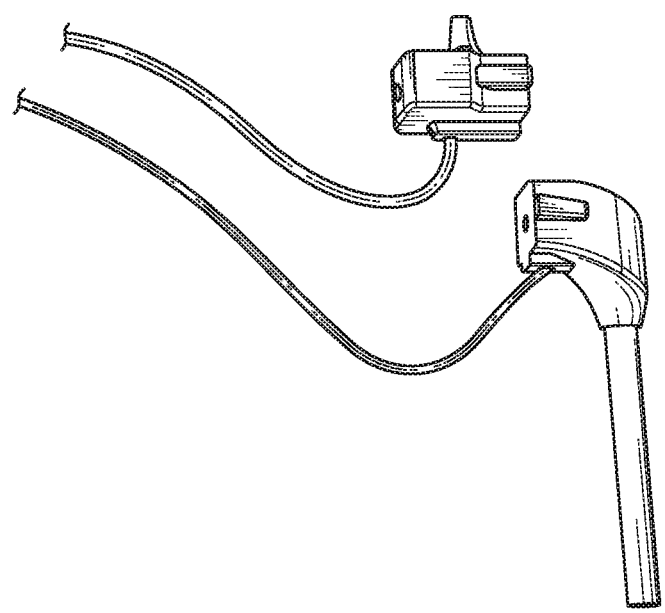

The drivers 232A and 232B can be mounted on the one or more pins 510 as illustrated in FIG. 6D and described herein. The one or more pins 510 can be exposed through corresponding one or more holes 610 in the drape 600. One or more covers 550 can be mounted on one or more pins 530 and/or 530' as illustrated in FIG. 6E and described herein. The one or more pins 530 and/or 530' can be exposed through corresponding one or more holes 610 in the drape 600.

Figure 6F:
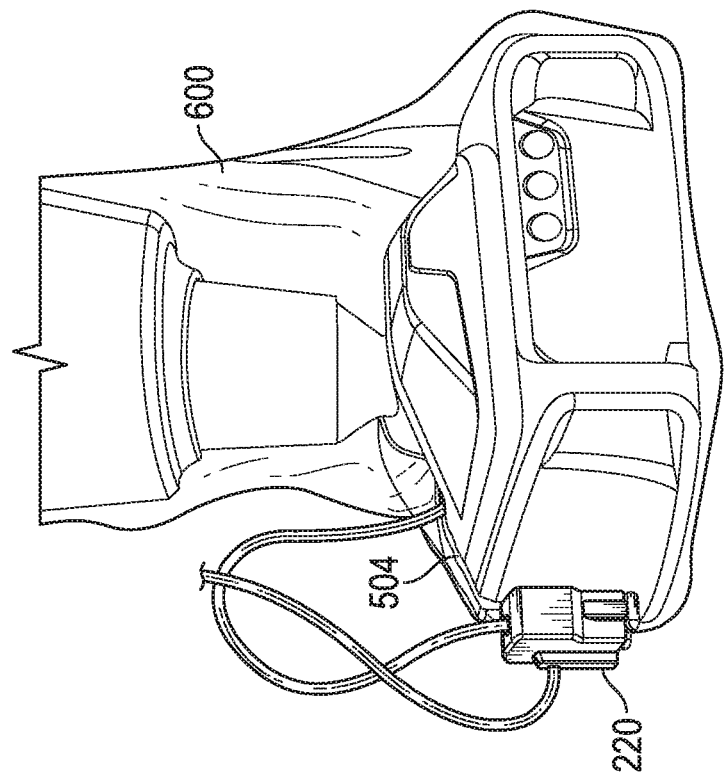
Figure 6F:
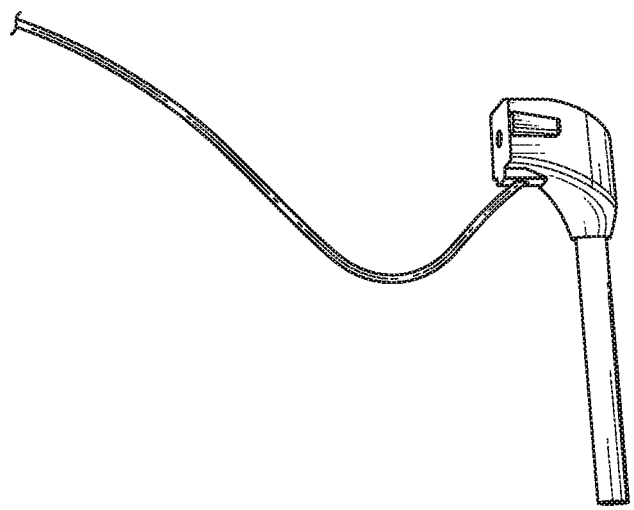

The visualization device 220 can be mounted on (or docked to) the mounting interface 500 as illustrated in FIG. 6F and described herein. The camera tube 224 (which can be sterile) can be inserted into the visualization device 220 as described herein. At least a portion of the loop of the camera tube 224 can be positioned in the slit 504 as shown. The drape 600 can include enough slack to allow the camera tube 224 and surrounding drape material to be placed in the slit 504. In some cases, the drape 600 can include a portion shaped to generally correspond with the slit 504 to facilitate positioning of the portion of the loop of the camera tube 224 in the slit 504.

Figure 6G:
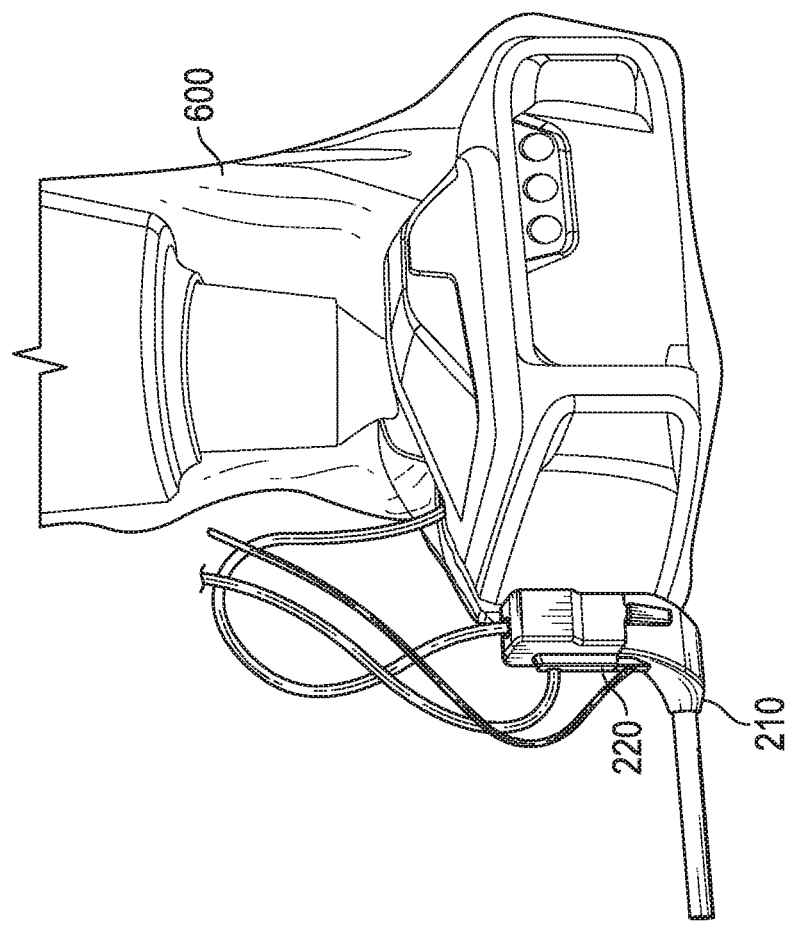

The insertion device 210 can be mounted on (or docked to) the mounting interface 500 as illustrated in FIG. 6G and described herein. In some cases, the insertion device 210 may have already been placed near or into the site of interest prior to being mounted on the mounting interface 500. In such cases, the drive unit 106 can be brought toward the insertion device 210 for docking the insertion device. The order of the mountings (or connections or dockings) can be interchanged. For example, the visualization device 220 can be mounted on the mounting interface 500 after the drive unit 106 has been docked with the insertion device 210. The visualization device 220 and insertion device 210 can be independent from each other (for example, modular) so that the visualization device 220 can be changed during surgery if it breaks down or otherwise becomes unresponsive without the need to first undock the insertion device 210 (and any instruments which may have been placed through the insertion device).

Figure 6H:
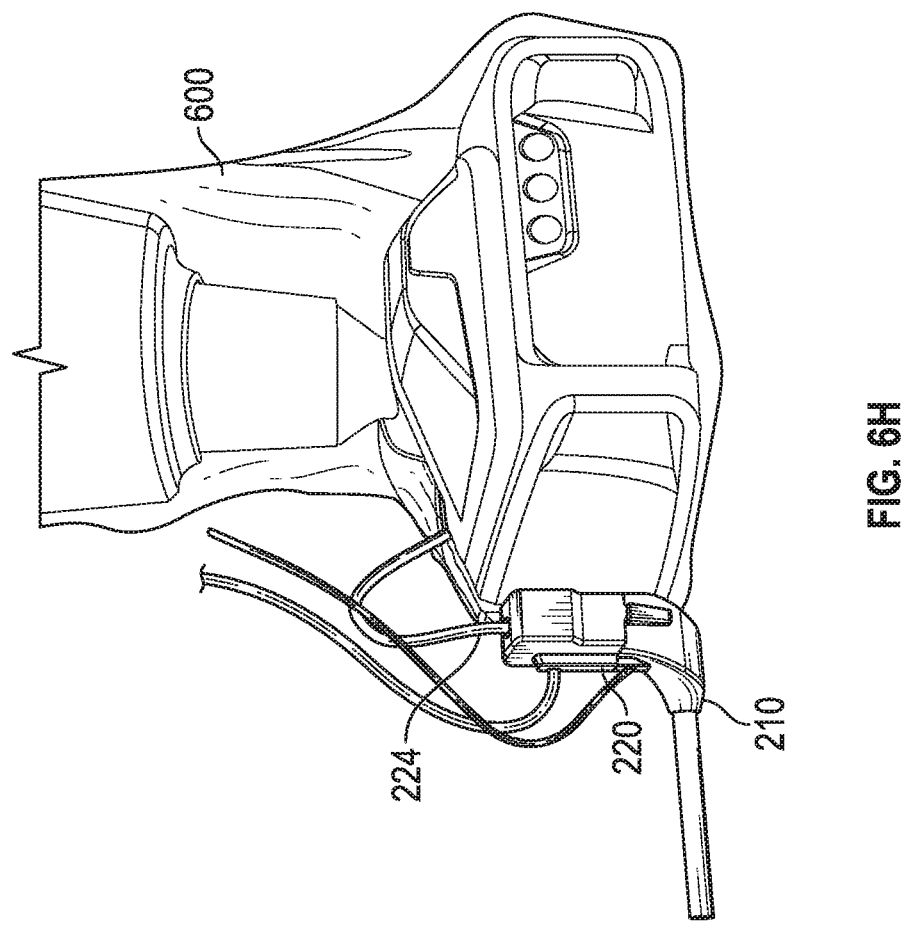

Camera tube 224 can be advanced though the visualization device 220 and inserted into the interior of the insertion device 210 as illustrated in FIG. 6H and described herein. Camera tube 224 can be further advanced through the interior of the insertion device 210 so that the distal end 224B exits the insertion device 210 as illustrated in FIG. 6I and described herein. The distal end 224B of the camera tube 224 can be advanced near or into the site of interest. Then, one or more instruments (which can be sterile) can be inserted and advanced near or into the site of interest.

In some cases, a user, such as a nurse, can insert one or more instruments, dock one or more of the visualization device or insertion device on the mounting interface 500, and advance and/or retract the camera tube 224. A surgeon operating the robotic surgical system 100 can cause the camera tube 224 to be advanced and/or retracted. For example, the surgeon can operate the camera tube 224 once the distal end 224B of the camera tube has been inserted into the opening 410 and past opening 412.

Operation of a Visualization Device

As described herein, the visualization device 220 can include an imager, such as the imager 430 illustrated in FIG. 4B. The imager can be positioned at or near the tip of the distal end 224B of the camera tube 224. As described below, the imager can be oriented in various positions in the camera tube 224.

Figure 7A:
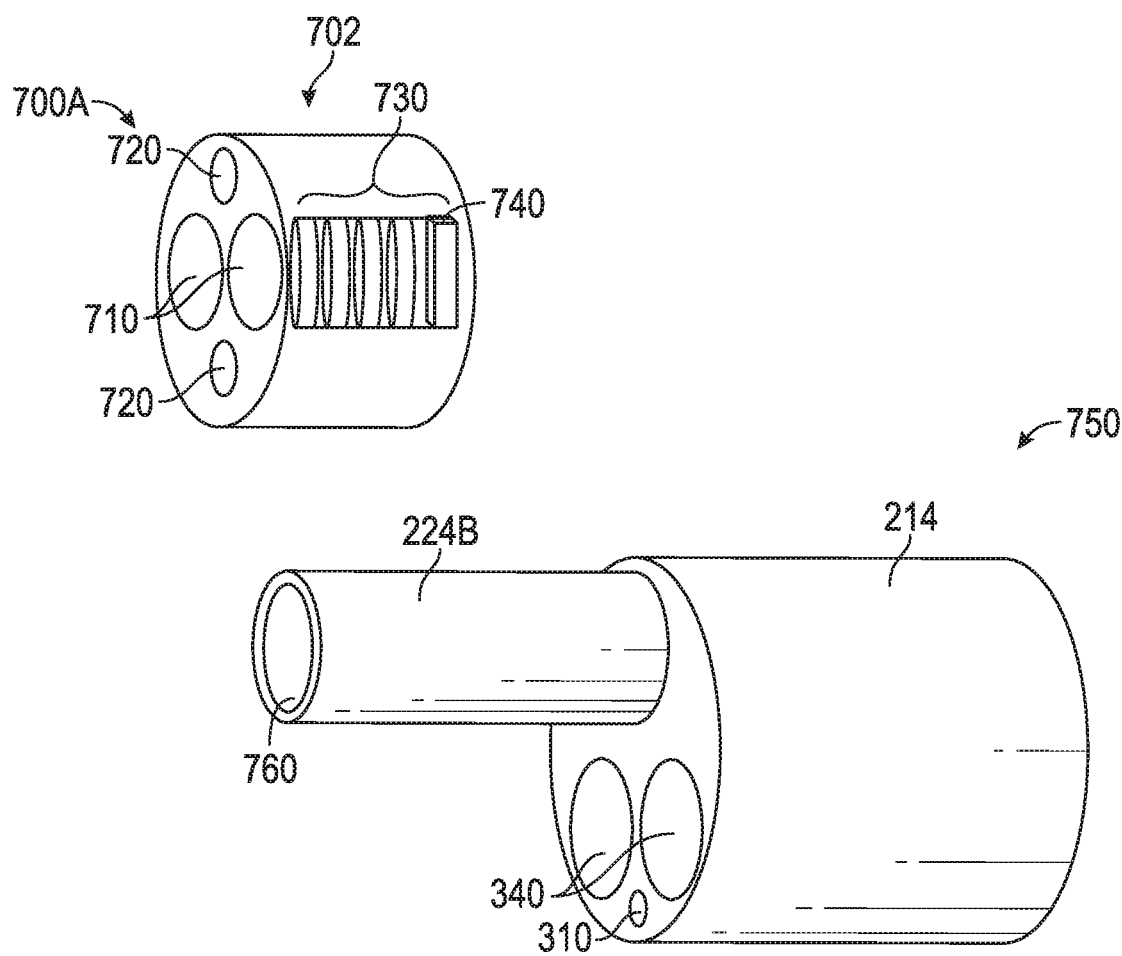
FIGS. 7A-7H and 8 illustrate visualization devices with imagers according to some embodiments.

FIG. 7A illustrates a combination 700A of an image module or imager 702, which can be similar to the imager 430, and a proximal end 750 of the insertion device 210. The imager 702 can include one or more cameras 710 and one or more illumination channels in which one or more illumination devices 720 can be positioned. The one or more illumination sources or devices 720 can illuminate at least a portion of the site of interest to permit viewing of the at least one portion. The one or more illumination devices can include one or more light sources, such as light emitting diodes (LEDs), optical fiber(s), or the like. The optical fibers can traverse along the length of the insertion device 210 (or portion of the length of the insertion device). As illustrated, in some cases, two (or more) cameras 710 can be used in order for the imager 702 to operate as a stereoscopic imager, and to produce three-dimensional representation of at least a portion of the site of interest. Each of the cameras 710 can include one or more lenses 730 that focus light from and/or reflected by at least the portion of the site of interest on an image sensor 740. The one or more lenses 730 can include concave and/or convex lenses. In some cases, one or more lenses 730 can be moved to adjust the zoom (such as, an optical zoom). The image sensor 740 can detect the light and convert it to image information or data. For instance, the image sensor 740 can measure brightness at a plurality of points. The image sensor 740 can include at least one of charge-coupled devices (CCDs), complementary metal-oxide-semiconductor (CMOS) image sensors, or the like. The image sensor 740 can be a digital and/or analog image sensor. In some implementations, one camera 710 can be used or more than two cameras can be used.

The imager 702 can be positioned in the camera tube 224, such as at or near the tip of the distal end 224B of the camera tube. For example, the imager 702 can be at least partially inserted into the camera tube 224. As illustrated in FIG. 7A and described herein, the camera tube 224 with the distal end 224B can be inserted in a channel of the plurality of channels 214 of the insertion device 210. As described herein, such channel can be the channel 320. A protector 760 (such as glass or plastic) can be positioned in the camera tube 224 closer to the tip than the imager 702. The protector 760 can protect the imager 702 from breaking or malfunctions due to, for example, coming into contact with fluid in the site of interest. The imager 702 can serve as the primary camera as described herein. A secondary camera can be positioned in the channel 310 as described herein.

In some cases, the imager 702 can be included inside an imaging module (not shown) that may be hermetically sealed and that is coupled or otherwise mounted to the distal end 224B of the camera tube. The imaging module enclosing the imager 702 could be removably mounted and allow the ability to have the imaging module and camera tube 224 manufactured and/or packaged at separate locations. A variety of imaging modules (for example, with different orientations) can be provided as described herein.

Figure 7B:
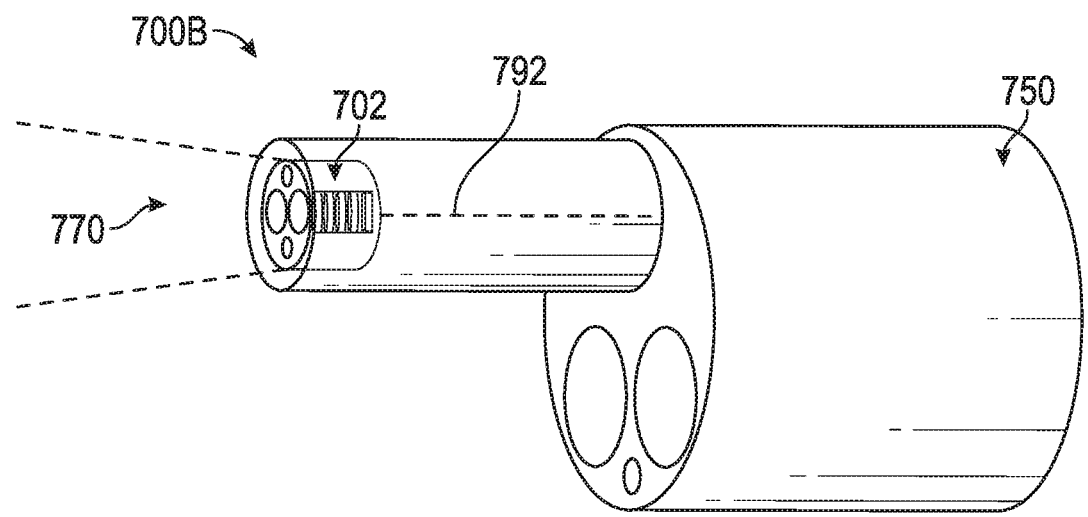

Different orientations of the imager 702 in the camera tube 224 of the visualization device 220 can provide different advantages for exploring the site of interest. In some embodiments, the imager 702 can be positioned along or substantially along a central axis 792 of the distal end 224B of the camera tube 224 as illustrated in an arrangement 700B of FIG. 7B. In such orientation, the imager is not tilted down or up with respect to the distal end 224B of the camera tube when the proximal end is extended away from the insertion device 210 toward the site of interest. A field of view 770 of the imager 702, which can represent an area or region in which the imager obtains or captures image data, can be oriented along or substantially along the central axis 792. The field of view 770 can encompass a region straight ahead of the distal end 224B of the camera tube 224.

Advantageously, in some cases, the imager 702 of the arrangement 700B can provide image data of at least a portion of the site of interest when the site is positioned in front of the insertion device 210. For example, the imager 702 can "look straight ahead" or provide image data of a region in front as the distal end 224B of the camera tube 224 exits the channel of the insertion device 210. When the insertion device 210 is positioned adjacent the site of interest, imager positioning in the arrangement 700B can permit viewing the site of interest. This can be important, for example, to facilitate safe insertion of at least a portion of the distal end 224B (along with, for example, the primary camera) into the site of interest.

Figure 7C:
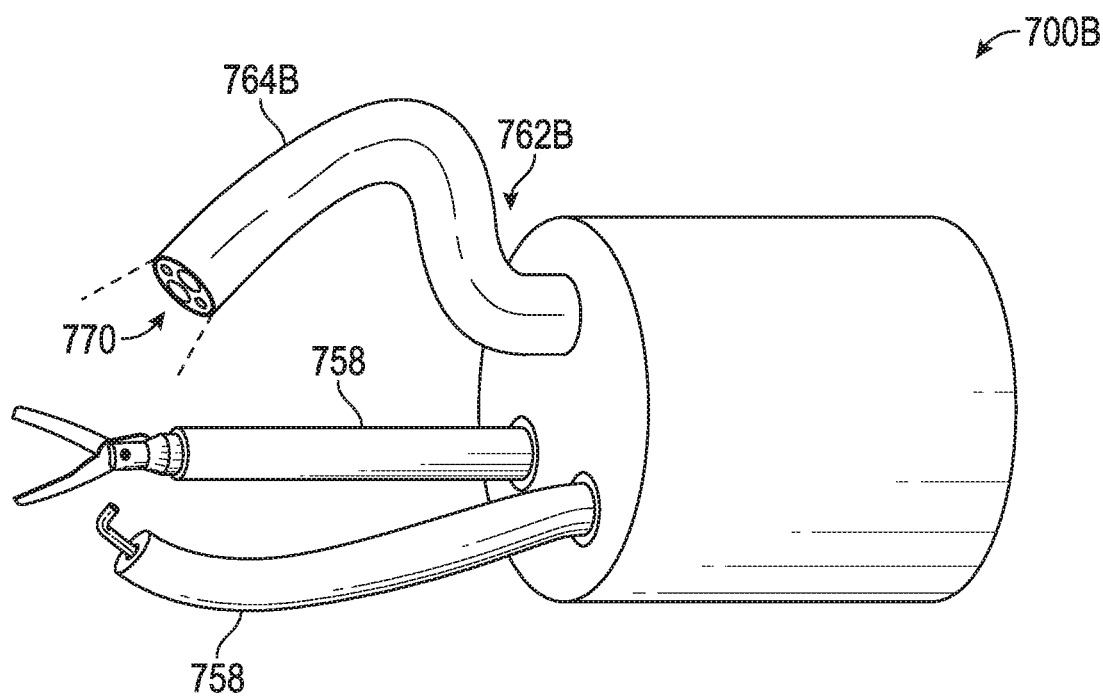

In some cases, the one or more instrument channels 340 are positioned below the channel 320 through which the distal end 224B of the camera tube 224 is passed. With reference to FIG. 7C, when one or more instruments are inserted through one or more instrument channels 340, it may be desirable to orient the imager 702 of the arrangement 700B to obtain a field of view oriented at least partially downward. For example, the imager 702 can be positioned to "look down" at the one or more instruments. Orienting the field of view 770 at least partially downward can advantageously permit viewing of the insertion of one or more instruments 758 into the site of interest. This can facilitate safe insertion of the one or more instruments into the site of interest.

As illustrated in FIG. 7C, in order to orient the field of view 770 at least partially downward, the distal end 224B of the camera tube 224 may be bent along a plurality of segments or sections 762B and 764B. As described herein, section 764B can correspond to the tilt section 442, and section 762B can correspond to the pan section 444. Both sections 762B and 764B may be bent to orient the imager 702 to provide image data relating to the position of the one or more instruments 758.

Figure 7D:
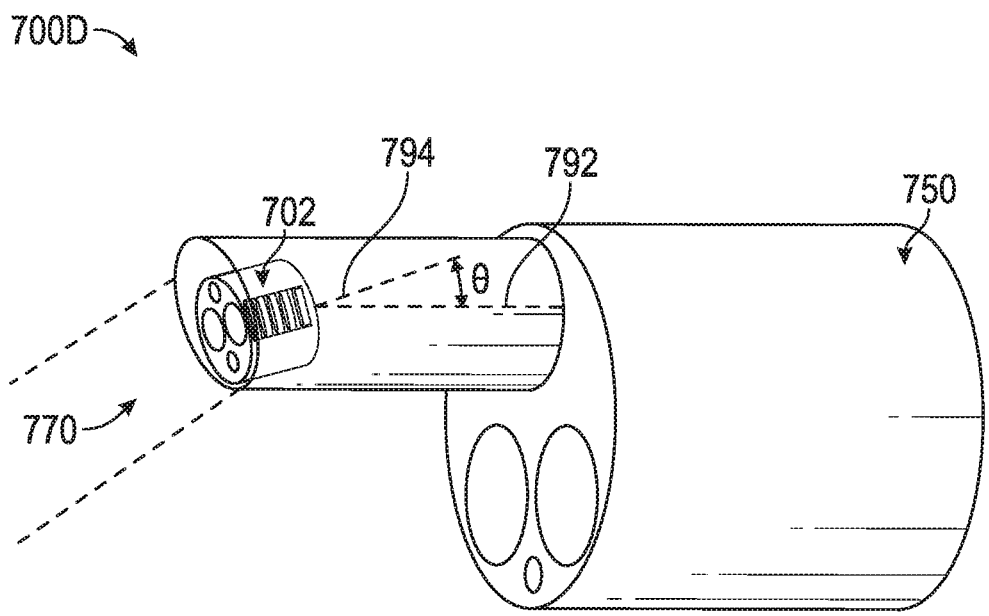

FIG. 7D illustrates an arrangement 700D in which the imager 702 is tilted downward at an angle θ relative to the central axis 792. The angle θ is formed between the central axis 792 and a central axis 794 of the imager 702. The angle θ can be 10 degrees or less or more, 15 degrees or less or more, 20 degrees or less or more, or the like. Tilting the imager 702 downward can cause the field of view 770 to be oriented at least partially downward. Advantageously, the field of view 770 can capture at least a portion of the region in front (which, for example, can be the site of interest as described herein) as well as at least a portion of the region below the imager 702. The arrangement 700D can permit viewing of the position of the one or more instruments 758 as well as viewing of at least the portion of the site of interest. This can facilitate insertion of both the primary camera and the one or more instruments 758.

Figure 7E:
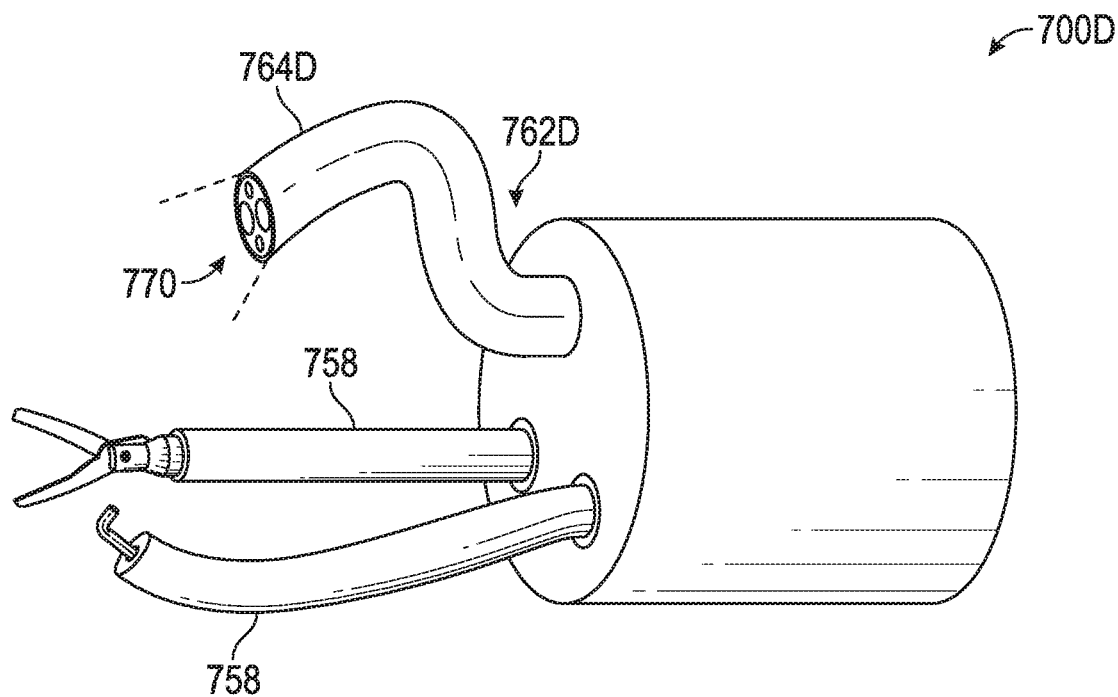

As illustrated in FIG. 7E, the field of view 770 in the arrangement 700D can be further oriented downward by bending the distal end 224B of the camera tube 224 along a plurality of segments or sections 762D and 764D. These sections can be similar to sections 762B and 764B of the arrangement 700B (shown in FIG. 7C), respectively. The angle or curvature of the bend in at least one of the sections 762D and 764D can be smaller than in at least one of the sections 762B and 764B, respectively. This reduction can be due to initially tilting the imager 702 downward at the angle θ.

Figure 7F:
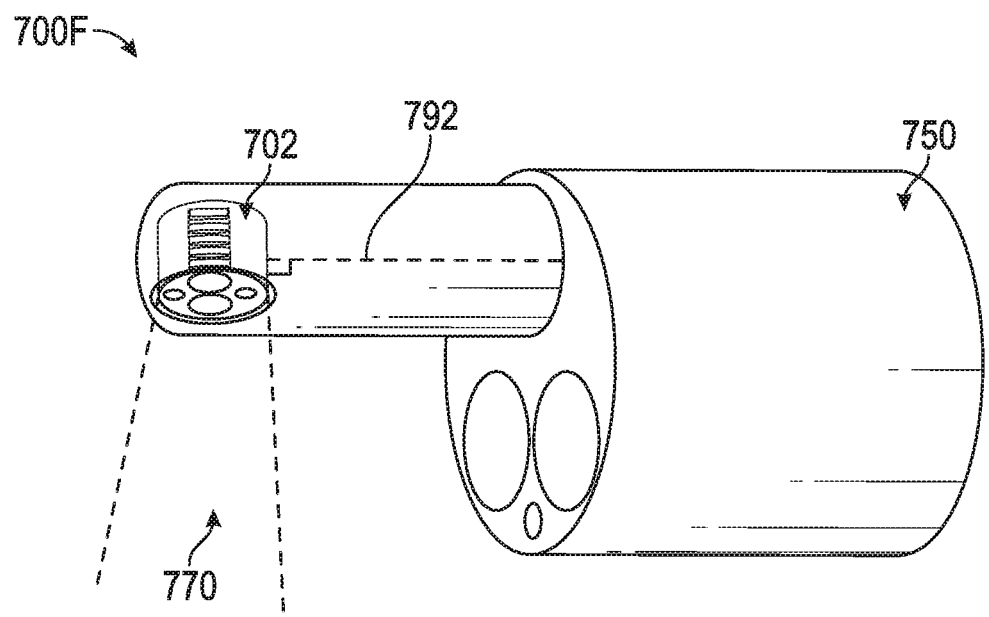
Figure 7G:
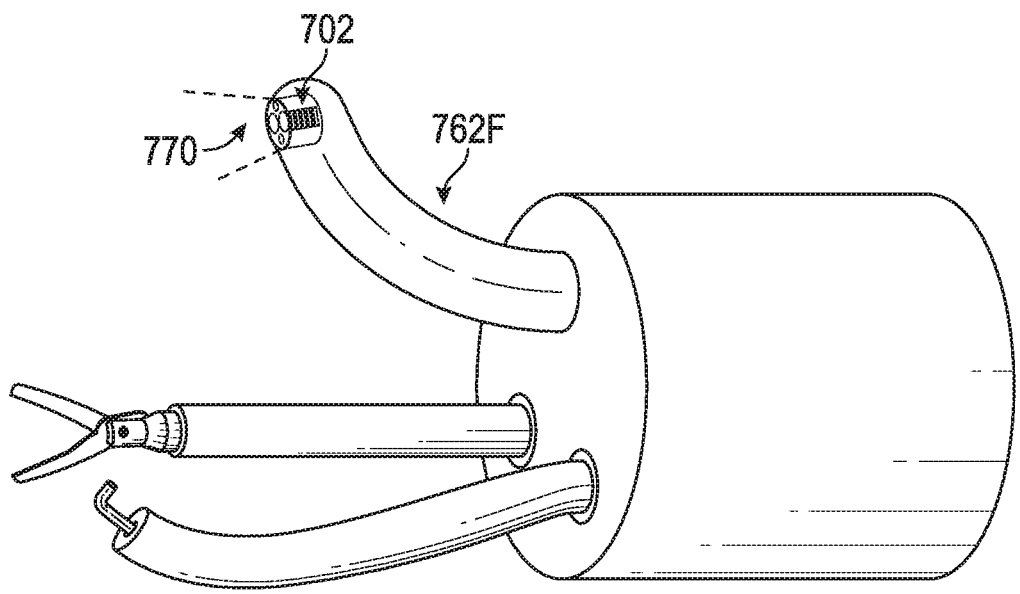

FIG. 7F illustrates an arrangement 700F in which the imager 702 is positioned downward at approximately 90 degree angle relative to the central axis 792. The field of view 770 captures a region below the imager 702. This can be advantageous to facilitate insertion of the one or more instruments 758. The field of view 770 may not capture or substantially not capture at least a portion of the region in front of the imager 702. In order to capture at least the portion of this region, the distal end 224B of the camera tube 224 can be bent along a segment or section 762F as illustrated in FIG. 7G. This orientation can facilitate insertion of the primary camera. Comparing with the arrangements 700B and 700D, adjustment of the orientation of a single segment 762F may be sufficient.

Figure 7H:
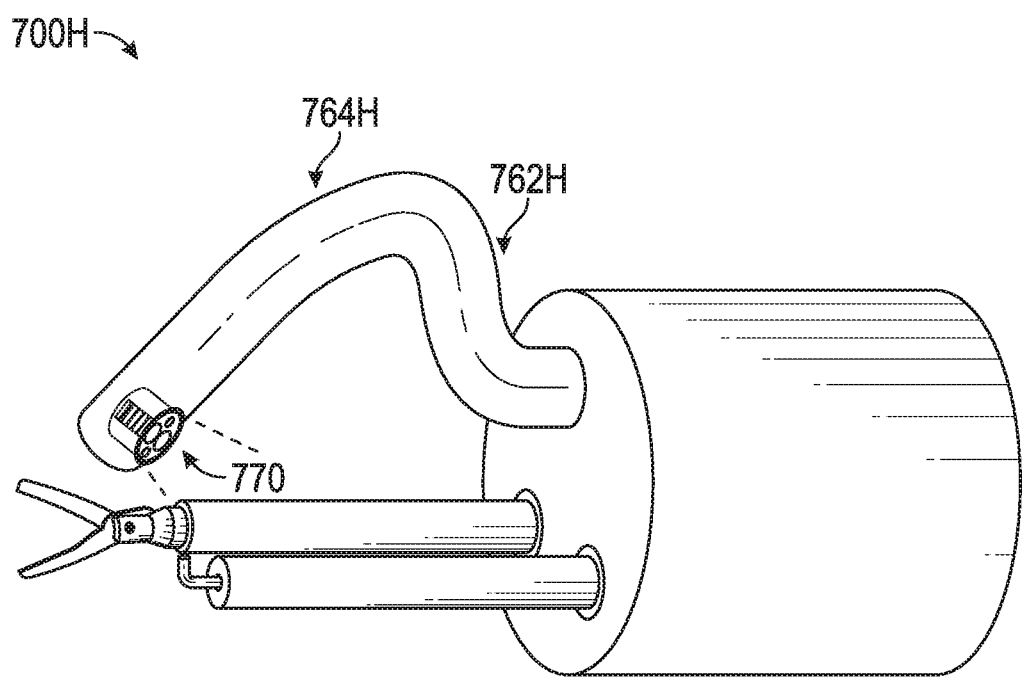

As illustrated in arrangement 700H of FIG. 7H, in order to capture at least a portion of a region behind the imager 702, the distal end 224B of the camera tube 224 may be bent along a plurality of segments or sections 762H and 764H. These sections can similar to sections 762B and 764B of the arrangement 700B, respectively. The field of view 770 of the arrangement 700H can permit viewing of the one or more instruments 758 being advanced through the one or more instrument channels in the insertion device 210.

Figure 8:
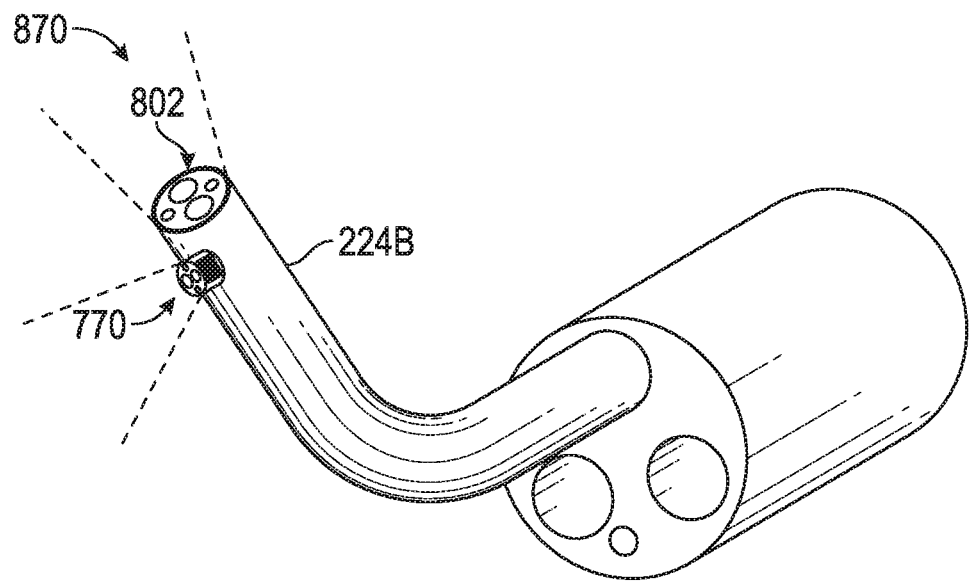

In some cases, a second or another imager can be provided in the arrangement 700F, in which the imager 702 is positioned substantially downward. For example as illustrated in FIG. 8, such second imager 802 can be positioned along or substantially along the central axis of the distal end 224B of the camera tube 224 similarly to the arrangement 700B. The second imager 802 can provide an additional field of view 870 to the field of view 770 of the imager 702. The field of view 870 can capture at least a portion of the region in front of the second imager 802. This can facilitate insertion of the primary camera, which can include both imagers 702 and 802.

In some implementations, the imager 702 can be tilted up. For example, this can be advantageous when one or more instrument channels through which one or more instruments are inserted are positioned above the channel 320 through which the distal end 224B of the camera tube 224 is passed.

As described herein, the imager 702 can be oriented differently relative to the central axis 792 of the distal end 224B of the camera tube 224. The imager 702 can be positioned substantially along the central axis 792, perpendicular to the central axis, or at any angle between 0 degrees and 90 degrees (facing up or down) relative to the central axis. Varying the orientation of the imager 702 can adjust the orientation of the field of view 770 of the imager. A suitable orientation of the imager 702 can be selected based on a desired field of view 770.

In some cases, one or more actuators configured to adjust orientation of the imager 702 can be provided. For example, the one or more actuators can include one or more motors. Advantageously, orientation of the imager 702 can be adjusted in operation.

Movement of Primary Camera

Figures 9A, 9B:
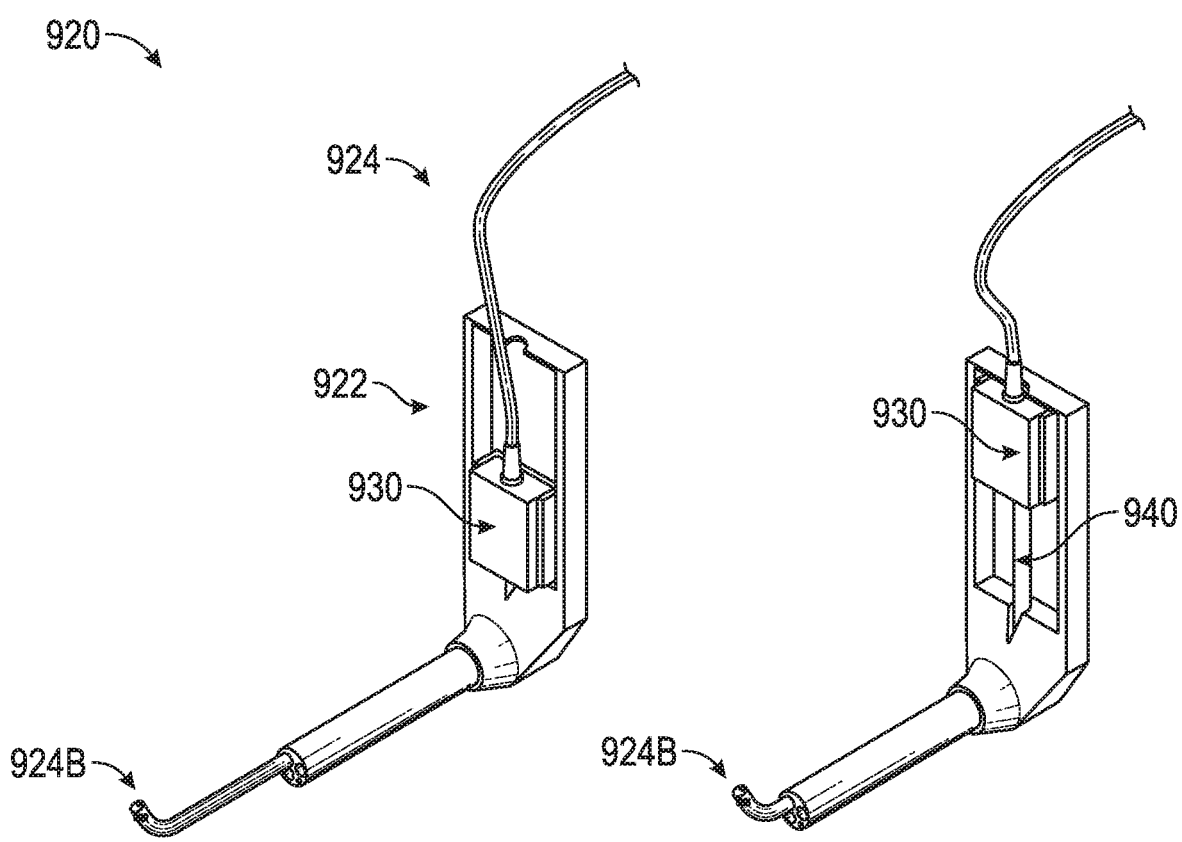
FIGS. 9A-9B and 10A-10B illustrate visualization and/or insertion devices according to some embodiments.

Other mechanisms for advancing and/or retracting a camera tube can be used. In some cases, a movement device can travel along with the camera tube. For example, FIGS. 9A-9B illustrate an insertion and/or visualization device 920 with a movement device 930 configured to travel vertically (or, in some cases, horizontally) to advance and/or retract a camera tube 924. FIG. 9A illustrates a distal end 924B of the camera tube 924 extending at a maximum distance toward the site of interest (such as, fully extended). In this position, the movement device 930 is moved downward, such as to the bottom position in a housing 922, to advance the distal end 924B. FIG. 9B illustrates the distal end 924B of the camera tube 924 extending at a maximum distance away from the site of interest (such as, fully retracted). In this position, the movement device 930 is moved upward, such as to the top position in the housing 922, to retract the distal end 924B.

The movement device 930 can include one or more actuators (for example, one or more motors) that move the movement device up and/or down (or, in some cases, left and/or right) within the housing 922. For example, the movement device 930 can move along a rail or post 940. In some cases, the rail 940 can include a chain for facilitating or guiding movement of the movement device. The movement device can include additional one or more actuators configured to tilt and/or pan one or more cameras positioned in the camera tube 924.

Figure 10A:
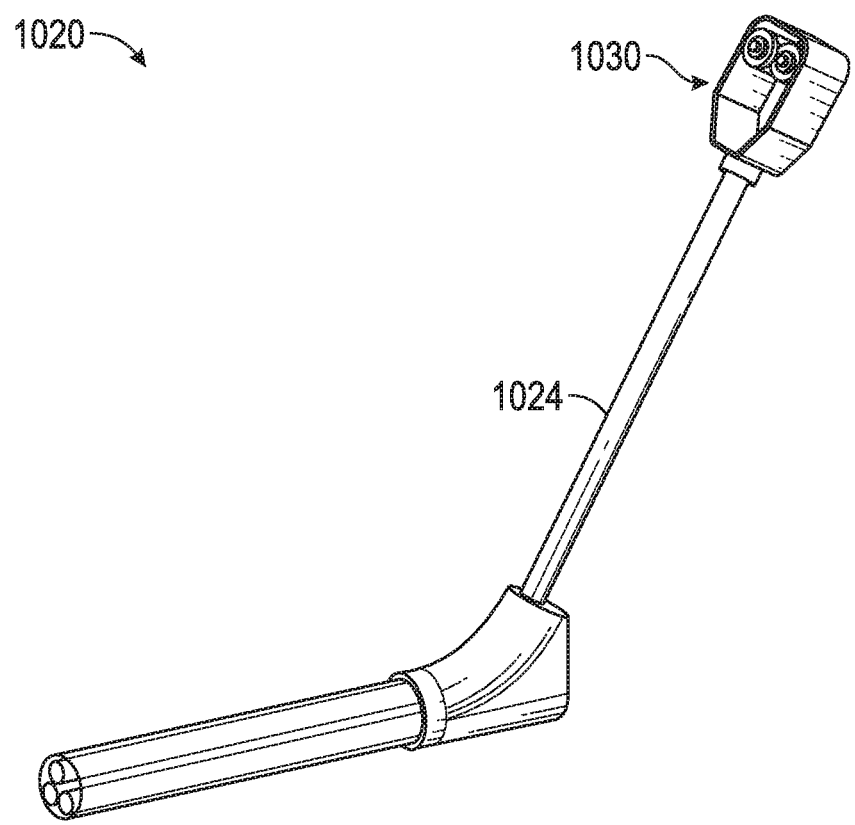
Figure 10B:
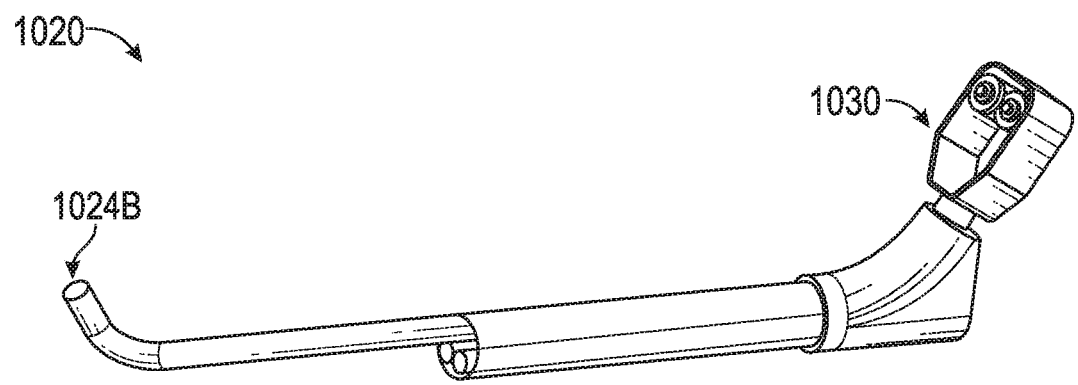

As illustrated in FIGS. 10A-10B, a movement device 1030 may be positioned outside and/or away from a housing of an insertion and/or visualization device 1020. The movement device 1030 can move downward to advance a distal end 1024B of a camera tube toward the site of interest. The movement device 1030 can move upward to retract the distal end 1024B. As illustrated, the movement device 1030 can downward and/or upward at an angle to the vertical axis.

Figure 11:
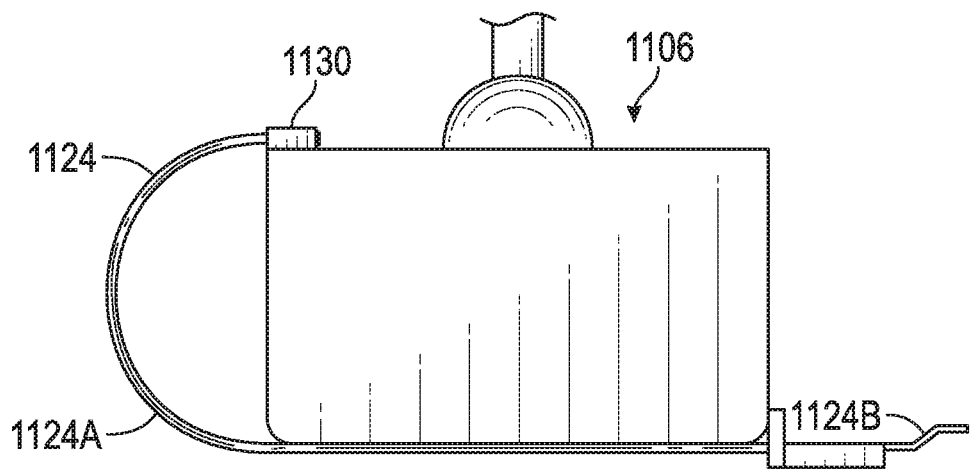
FIGS. 11 and 12A-12D illustrate drive units of a robotic surgery system according to some embodiments.

In some cases, a movement device can be substantially stationary and the camera tube may not form a loop as described herein. For example, FIG. 11 illustrates a drive unit 1106 supporting (for example, on top) a movement device 1130 configured to advance and/or retract a camera tube 1124 that includes a proximal end 1124A and a distal end 1124B. The movement device 1130 can advance and/or retract the distal end 1124B of the camera tube 1124 along substantially horizontal direction (or, in some cases, a vertical direction). The proximal end 1124A of the camera tube 1124 can provide "slack" or sufficient camera tube length to advance the distal end 1124B to a maximum distance toward the site of interest (or away from the drive unit 1106). In some cases, the movement device 1130 can be positioned at another location on the drive unit 1106 or be supported by another component of a robotic surgery system.

Figure 12A:
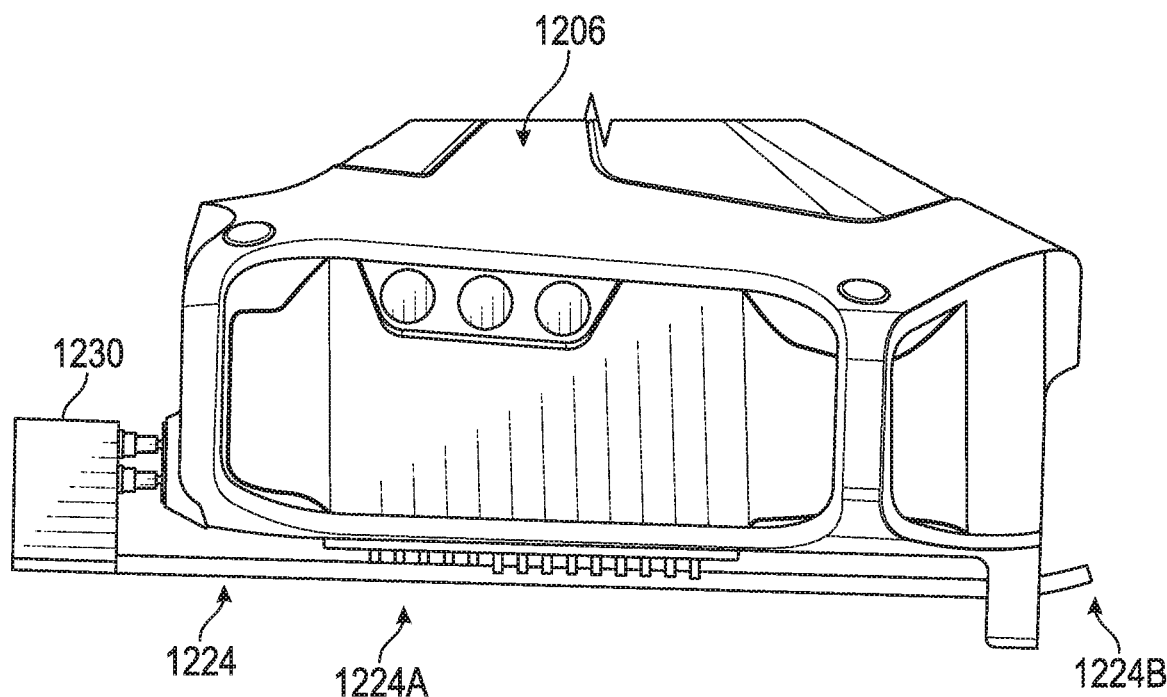
Figure 12B:
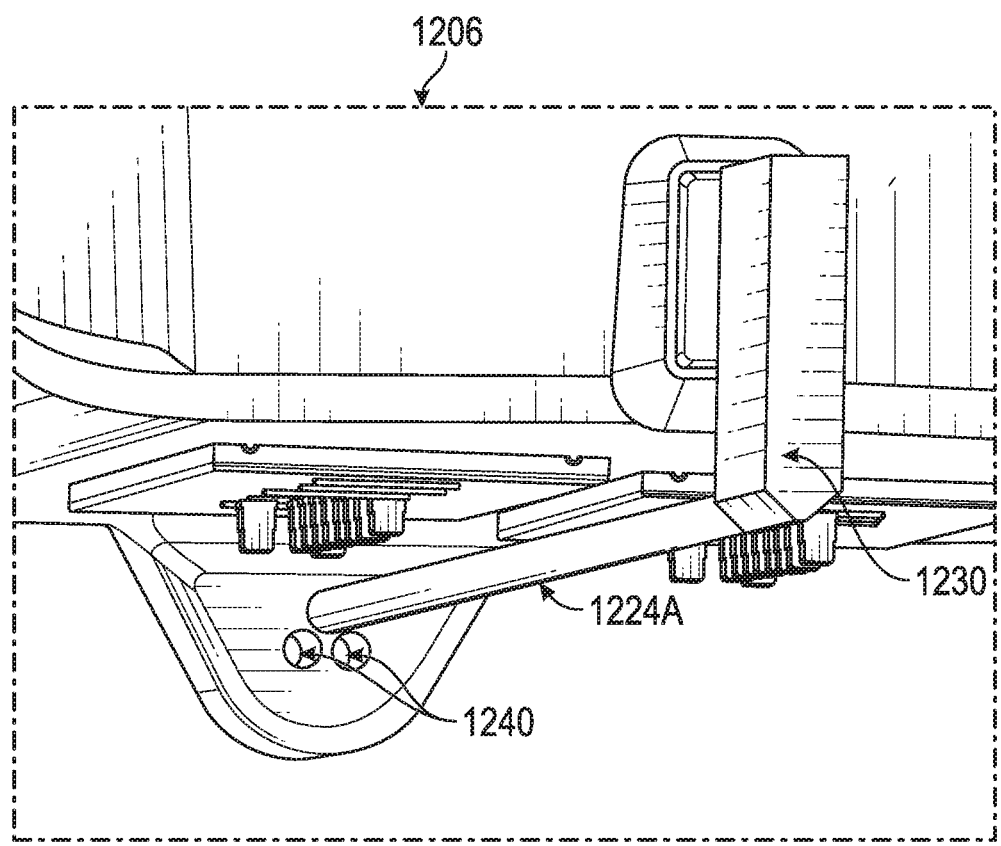

In some cases, at least a portion of the camera tube can be substantially rigid. For example, FIG. 12A illustrates perspective view of a movement device 1230 supported by a drive unit 1206. The movement device 1230 can be positioned at the rear of the drive unit 1206. The movement device 1230 can be configured to advance and/or retract a camera tube 1224 that includes a proximal end 1224A and a distal end 1224B. FIG. 12B illustrates a bottom view showing one or more openings 1240 for one or more instruments (not shown). In operation, the one or more instruments can be positioned adjacent to the camera tube 1224. In some cases, the movement device 1230 can be positioned at another location on the drive unit 1206 or be supported by another component of a robotic surgery system.

Figure 12C:
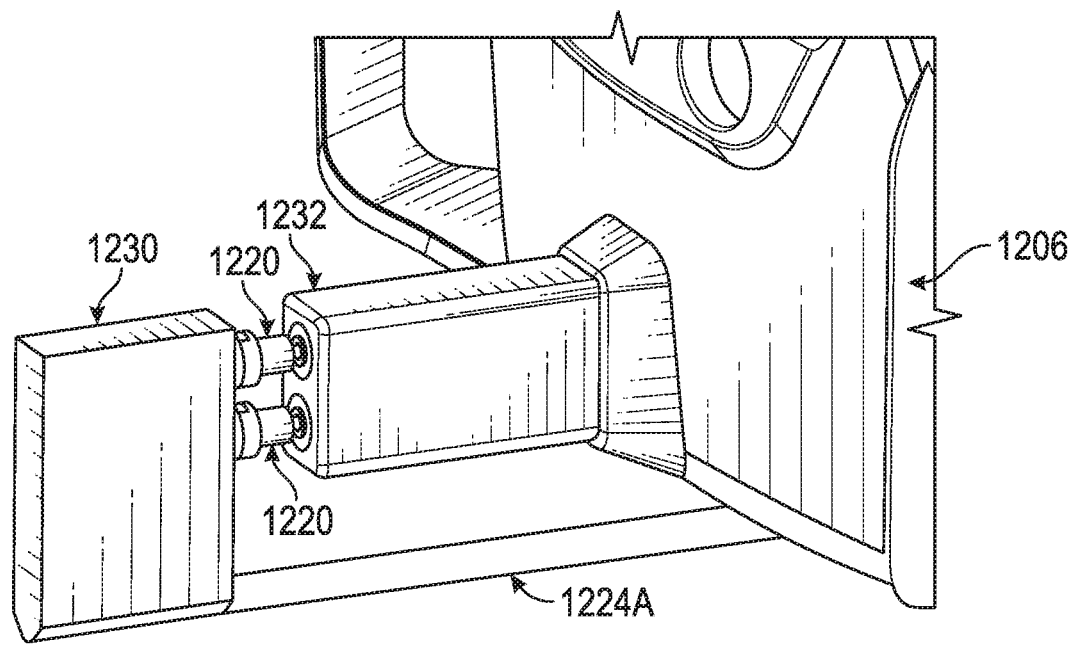

FIG. 12C illustrates the camera tube extending at maximum distance away from the site of interest (such as, fully retracted). In this position, a movement portion or mover 1232 can be fully retracted. For example, the mover 1232 can retracted backward and oriented outside an interior portion of the drive unit 1206. Movement of the mover 1232 can cause the movement device 1230 to move in the same direction. The camera tube 1224 can be attached or connected to the movement device 1230, and movement of the movement device 1230 can cause the camera tube 1224 to move in the same direction. Also illustrated are one or more actuators 1220 configured to control tilt and/or pan of one or more cameras positioned in the camera tube 1224.

Figure 12D:
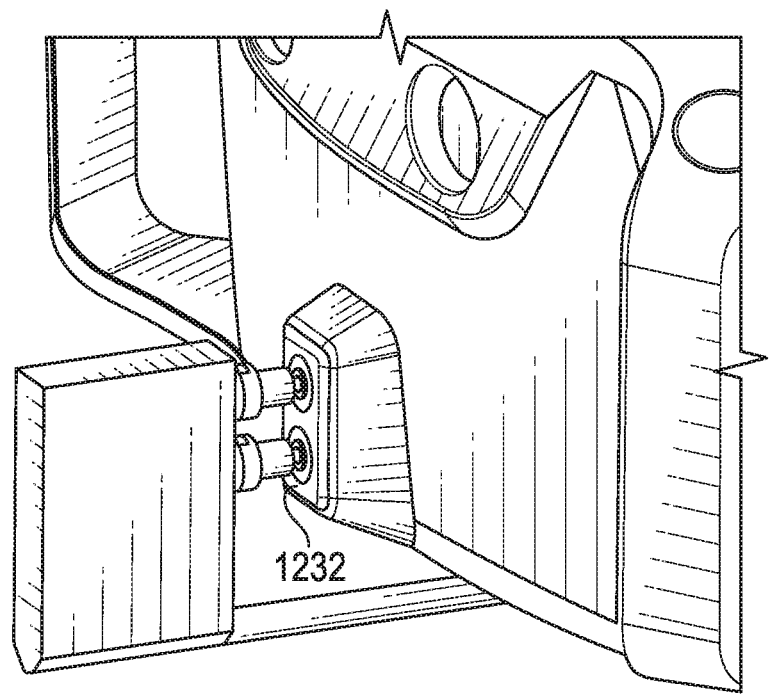

FIG. 12D illustrates the camera tube extending at maximum distance toward the site of interest (such as, fully extended). In this position, the mover 1232 can be fully extended. For example, the mover 1232 can be extended forward and oriented in the interior portion of the drive unit 1206. As described, at least a portion of the camera tube 1224 can be substantially rigid at least because the proximal end 1224A may be maintained as substantially straight. For instance, the proximal end 1224A may not be bent in contrast with, for example, in FIG. 11). The proximal end 1224A can include the substantially rigid portion. Advantageously, having the substantially rigid portion may prevent the camera tube 1224 coming into contact with unsterile surface or object, such as the floor, because of the length of the slack.

Advantageously, using a visualization device configured to cause the camera tube to form a loop as described herein can reduce or eliminate the risk of a camera tube coming into contact with an unsterile surface or object. Advantageously, drivers configured to rotate (such as, rollers) to advance/retract the camera tube as described herein can facilitate reducing the size of a visualization device.

Imaging Site of Interest

Figure 13:
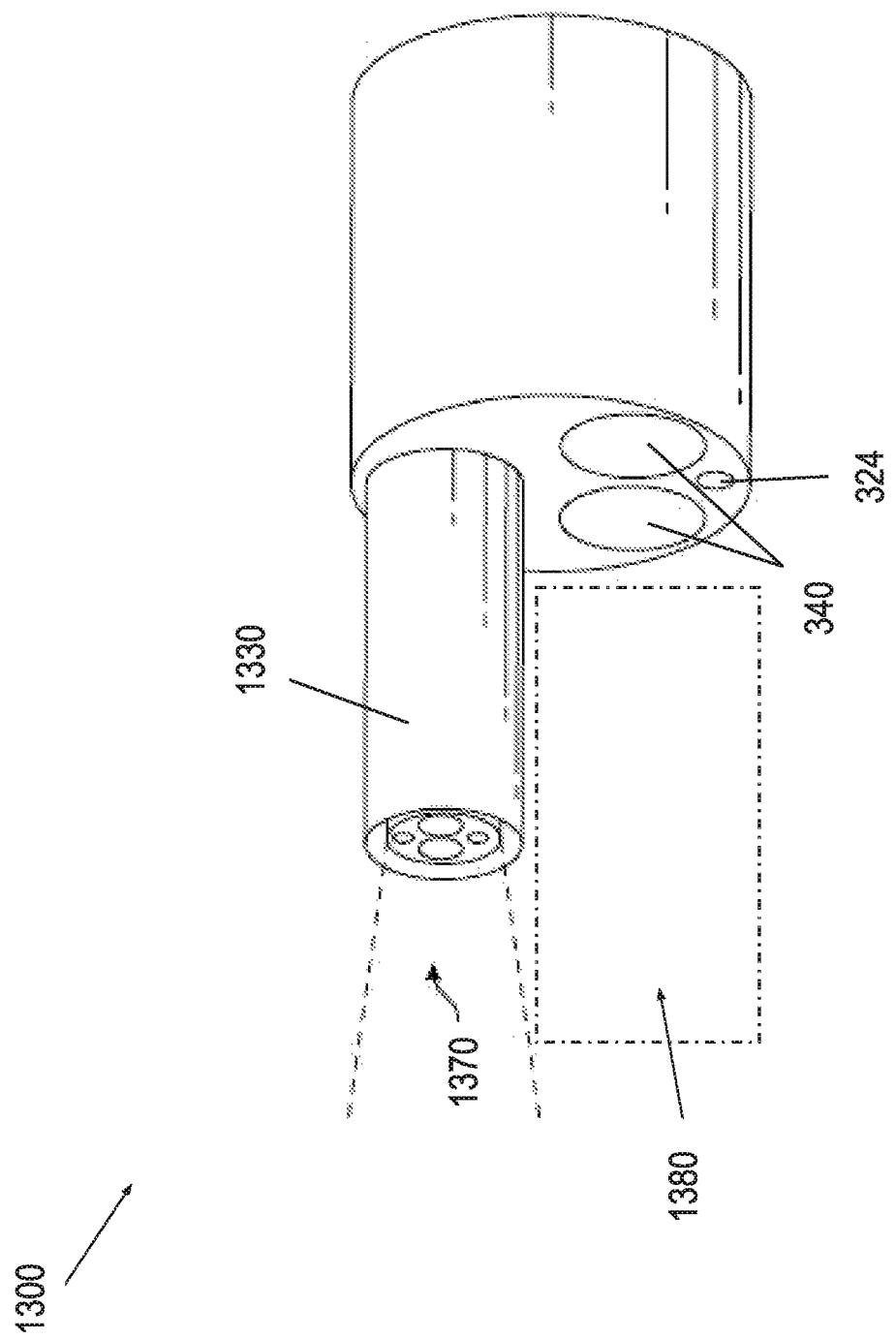

FIG. 13 illustrates an insertion device 1300, which can be the same as or similar to any of the insertion devices described herein. The insertion device 1300 can include the housing 214, primary camera 1330, secondary camera 324, and one or more instrument channels 340, each of which can be the same as or similar to any of the components described herein having the same or like name or reference number. A field of view 1370 of the primary camera 1330 is illustrated. Region 1380 adjacent to one or more instrument channels illustrates a blind spot in the field of view of the primary camera. When one or more surgical instruments are loaded through the one or more instrument channels 340 or positioned at the site of interest (such as, a surgical site), the one or more instruments can pass through the region 1380. It may not be desirable to load or position the one or more instruments in the site of interest without the ability to view the one or more instruments passing through the region 1380. For example, there may be tissue or organs obstructing the one or more openings of the one or more instrument channels 340 or positioned in the region 1380. In some cases, the primary camera 1330 is loaded after the one or more instruments are loaded. In such situations, the region 1380 may be larger than or otherwise different from that illustrated in FIG. 13.

As described herein, the secondary camera 324 can facilitate loading or positioning in the site of interest of one or more instruments or one or more primary cameras. The secondary camera 324 can capture image data of at least a portion of the site of interest, including the region 1380. Use of the secondary camera 324 can provide the ability to avoid blind loading or positioning of the one or more instruments or primary cameras, which increases safety. The secondary camera 324 can provide the operator (such as, a surgeon) with the ability to view the region 1380. This can avoid, for example, any unintended contact with tissue or organs.

As described herein, the secondary camera 324 can be positioned in a channel (such as, the channel 310) and utilized by the robotic surgery system to display image data obtained from the secondary camera on one or more of the primary or secondary displays before an insertion device (such as, the insertion device 210) is coupled to a drive unit (such as, the drive unit 106). This can be advantageous to facilitate safe insertion or positioning of the insertion device in the site of interest (for example, into the abdomen of a patient after an initial incision has been made). This can provide the operator (such as, a surgeon) with the ability to move the insertion device (for example, pivot the insertion device about an incision point) to find a desirable position for the insertion device prior to coupling the insertion device with the drive unit. This can also provide the ability to survey the site of interest for any abnormalities, such as for example, excess scar tissue, to find a better position for the insertion device, avoid contacting tissue or organs, or the like. The secondary camera 324 can provide visibility to the operator that would otherwise not be available when using an insertion device without a secondary camera or when using trocars for laparoscopic and/or robotic surgical procedures.

Image data captured by the secondary camera can be transmitted to the electronic circuitry of the workstation 102 and displayed on one or more of the primary display 120 or the secondary display 123, as described herein. In some cases, image data captured by the secondary camera can be displayed on the primary display (or portion thereof). Image data captured by the secondary camera can be displayed on both primary and secondary displays or on one of the displays. For example, when the primary camera is not connected (as described herein), image data captured by the secondary camera can be displayed on the primary display. When the primary camera is connected, the primary display can be switched to display image data captured by the primary camera, and image data captured by the secondary camera can be displayed on the secondary display or as an overlay on the primary display. Image data from the secondary camera can be displayed on the primary display by covering a portion of the image data from the primary camera (for example, by displaying the image data from the secondary camera as picture-in-picture). In some cases, image data from the secondary camera may always be displayed on the secondary display (or portion thereof) or be displayed on the secondary display at least until the secondary display (or a portion thereof) is needed for another function.

When the primary camera is disconnected, such as during replacement of the primary camera, for the purpose of cleaning the primary camera (for example, cleaning the lens of the primary camera) or due to a failure of the primary camera, image data captured by the secondary camera can be displayed on the primary display. In cases when the primary display is configured to display image data captured by the primary camera when connected, the displayed image on the primary display can be switched to the image data captured by the secondary camera when the primary camera is disconnected. When the primary camera is reconnected, the displayed image on the primary display can be switched to image data captured by the primary camera.

In some cases, the primary camera is not connected (or is disconnected) when one or more of the insertion device or visualization device is not mounted on (or with) the mounting interface (mounting the insertion and/or visualization device can establish transmission of imaging data from the primary camera to the electronic circuitry), when the primary camera is not coupled to one or more of the drive unit 106 or the patient cart 104 (such coupling, for example via a cable, such as, the cable 240, can establish transmission of imaging data from the primary camera), when the distal end of the primary camera (such as, the distal end 224B) has not exited the channel (such as, the channel 320) of the insertion device, and/or the like. Determination that the primary camera has or has not been connected can include determination of failure or malfunction of the primary camera and determination that the primary camera is otherwise not communicating image data (for example, to the electronic circuitry of the workstation).

Determination that the primary camera has or has not been connected can be made, for example, by the electronic circuitry of the workstation. This determination can be made based on data from one or more sensors, such as a sensor positioned on the mounting interface (such as, the mounting interface 500), drive unit (such as, the drive unit 106), patient cart (such as, the patient cart 104), in the channel (such as, the channel 320; for example, at the exit of the channel), and/or the like. The one or more sensors can be electrical sensors, electromechanical sensors, optical sensors, etc.

In some cases, image data from the secondary camera (and/or the primary camera) can be transmitted for being displayed on a remote display. The remote display may be positioned inside or outside of an operating room in which the robotic surgery system (such as, the system 100) is positioned.

FIG. 14 illustrates an insertion device 1400, which can be the same as or similar to any of the insertion devices described herein. The insertion device can include a channel 310c positioned below one or more instrument channels 340 and configured to receive or enclose a secondary camera. As described herein, multiple secondary cameras can be used in some cases. As is illustrated, the insertion device 1400 can include a plurality of channels in which a plurality of secondary cameras is positioned. Each of the plurality of secondary cameras can be the same or similar to any of the secondary cameras described herein, such as the secondary camera 324. In some cases, one or more secondary cameras can be positioned above the one or more instrument channels 340. This can provide the operator with a view of the one or more instruments from an elevated position (above the one or more instruments), which can facilitate a more natural view of the one or more instruments and/or the site of interest. This can additionally or alternatively promote usefulness of image data captured by one or more secondary cameras to the operator.

As is illustrated, channel 310a can be positioned above the one or more instrument channels 340. Channel 310a can receive or enclose a secondary camera, whose field of view is illustrated as 1470. Advantageously, loading and positioning of one or more instruments would be at least partially captured in the field of view 1470. Alternatively or additionally, at least two channels configured to receive or enclose secondary cameras can be positioned in the regions 310b adjacent to the channel 320 configured to receive the primary camera. Regions 310b can be positioned on left and right sides of the channel 320. A pair of secondary cameras 1324a and 1324b can be positioned on the left and right sides, respectively, of the channel 320 as illustrated in FIG. 15A. In some cases, a channel configured to receive or enclose a secondary camera can be positioned above the channel 320. Any of the channels of the insertion device 1400 can be similar to any of the channels described herein having the same or like name or reference number. In some cases, additional one or more channels configured to receive or enclose one or more secondary cameras can be positioned in other areas of the insertion device 1400.

Image data captured by multiple secondary cameras can be processed (for example, by the electronic circuitry) to provide enhanced image data. Enhanced image data can be a stereoscopic image, which can illustrate a three-dimensional representation of the site of interest. Enhanced image data can provide depth of field control, which can relate to a distance that is in focus in the foreground and background of an image.

In some cases, any of secondary cameras described herein can include an ultra wide-angle lens (sometimes referred to as fisheye lens). This can facilitate capture of wide panoramic or hemispherical image data. Image data captured with such lens can include surrounding objects in or adjacent to the site of interest, such as tissue and organs, and can facilitate placement of one or more of the insertion device, one or more instruments, or one or more of the primary cameras as described herein. Such lens can be integrated into or function as a protector for the secondary camera, such as the protector 370.

In some cases, once the primary camera has been loaded and positioned in (or adjacent to) the site of interest (as for example, illustrated in any of the FIGS. 7C, 7E, and 7G), one or more processing techniques disclosed in U.S. Pat. No. 10,058,396, which is incorporated by reference in its entirety, can be used to provide a composite (sometimes referred to as "birds-eye") view of the site of interest. Advantageously, a realistic view of the site of interest can be presented to the operator.

In some cases, the field of view of any of the secondary cameras described herein can be oriented or angled downward, upward, to the left, or to the right. For example, the field of view of any of the secondary cameras positioned above the one or more instrument channels can be angled downward, as illustrated by the field of view 1470. This can facilitate viewing of the one or more instruments in the site of interest. To angle the field of view of any of the secondary cameras disclosed herein downward (or in another direction) a prism can be used. The prism can be positioned at or adjacent to a distal end of the secondary camera, such as in front of a lens of the secondary camera. The prism can be positioned adjacent to the distal end of the secondary camera, such as the distal end 324B illustrated in FIG. 3C. In some cases, a wedge prism can be used to deflect the light by a fixed (or variable) angle. Alternatively or additionally, one or mirrors, lenses, or the like can be used to angle the field of view downward (or in another direction).

FIG. 15B illustrates a cross-sectional view of an insertion device 1500 shown in FIG. 15A. The insertion device 1500 can be the same as or similar to any of the insertion devices described herein. Secondary camera 1324b can have a field of view 1570 that is angled downward. In some cases, the field of view 1570 can be angled downward by 5 degrees, 10 degrees, 20 degrees, 30 degrees, 45 degree or the like. A prism 1510 can be positioned as shown. The prism can be positioned in front (or closer to the distal end of the secondary camera 1324b).

In some cases, a region 1520 in front of the prism 1510 can be include an open cavity or be filled with substantially transparent or optically clear material, such as crystal, glass, plastic, film, or the like. For example, the region 1520 can be a glass window. Material positioned in or filling the region 1520 may not (or may only insignificantly) affect light passing through the region 1520 and not (or only insignificantly) distort image data being captured by the secondary camera 1324b. One or more of the material of the prism 1510, material of the region 1520, and dimensions of the region 1520, such as the diameter 1530, can be selected so that image data is captured without obstructions (or substantially without obstructions).

FIG. 16A illustrates an insertion device 1600, which can be the same as or similar to any of the insertion devices described herein. The insertion device 1600 can include a secondary camera 1624 (which can be the same or similar to any of the secondary cameras disclosed herein) positioned adjacent to (or in) the channel 320 configured to receive or enclose a primary camera. As shown, the secondary camera 1624 can be positioned above the channel 320. Positioning of the secondary camera 1624 in the device 1600 can facilitate loading and positioning of a primary camera in the site of interest. FIG. 16B illustrates a cross-sectional view of the device 1600. The secondary camera 1624 can include a prism 1610 (which can be similar to or same as the prism 1510). The prism can cause a field of view 1670 of the secondary camera to be angled downward, as described herein. The field of view 1670 can capture the site of interest (or at least a portion thereof). Region 1620 can be similar to or same as the region 1520. As described herein, region 1620 can include an open cavity or be filled with substantially transparent or optically clear material, such as crystal, glass, film, or the like. Region 1620 can be positioned adjacent to or flush with the interior surface (such as, a wall) of the channel 320, as illustrated in FIG. 16B. As shown in FIG. 16A, such positioning can allow the secondary camera 1624 to look downward through the channel 320 via the optically transparent region 1620 (such as, a glass window). One or more dimensions of the region 1620, such as the width 1630, can be selected so that image data is captured without obstructions (or substantially without obstructions), as described herein in connection with FIG. 15B. In some cases, one or more of the material of the prism 1610, material included in the region 1620, and one or dimensions of the region can be selected so that the field of view 1670 coincides with or captures substantially the entirety of the cross-section 1640 of the channel 320 and/or image data captured by the secondary camera 1624 can be captured without obstructions (or substantially without obstructions).

As described herein, one or more illumination devices can be included or integrated in any of the insertion devices described herein. The one or more illumination devices can be positioned on the front distal face of an insertion device to illuminate the site of interest. The one or more illumination devices can be used in addition to or instead of illumination device(s) of the primary camera. The one or more illumination devices can be positioned in regions on the front distal face of the insertion device that are not occupied by any of the camera channels or instrument channels.

In some cases, one or more illumination devices can illuminate the region 1380 illustrated in FIG. 13. For example, one or more illumination devices can be positioned below the one or more instrument channels 340 or positioned in line with or above the one or more instrument channels and angled downward, as described herein. Any of the illumination devices can be angled in any direction, as described herein. The illumination devices may include optical fibers that extend along and traverse at least a portion of the insertion device to carry light generated from an area remote from the front distal face, including for example, a proximal portion of the insertion device or from another part of the system or operating room. In other cases, the illumination devices may include distally placed light generating device such as a light emitting diode (LED), including for example, a multi-sided LED that more readily dissipates light in multiple directions to better light the surgical site. An example of such an LED includes the high-power LED, WICOP-19 by Seoul Semiconductor Co., Ltd. of South Korea.

In some cases, as described herein, any of the insertion devices can include an opening or port for one or more of suction or irrigation of the site of interest, removal of smoke from the site of interest, or the like. Any of the primary or secondary cameras disclosed herein can capture thermal image data, fluorescence image data, or the like. In some cases, any of the secondary cameras disclosed herein can be removed during use and replaced with another secondary camera having similar or different function. For example, a secondary camera configured to capture image data can be removed and replaced with an infrared secondary camera configured to capture thermal imaging data. Any of the secondary cameras disclosed herein can be removed during use and replaced with another device configured to perform a function different from imaging the site of interest, such as a suction device, irrigation device, smoke evacuator, or the like, or be replaced with an instrument actuatable by a drive unit (such as, the drive unit 106) or a manually actuatable or otherwise controllable instrument, such as a manually actuatable laparoscopic instrument. This can facilitate positioning in (or adjacent to) the site of interest devices with different function via a single incision (or multiple incisions) formed for positioning of the insertion device.

Other Variations

Those skilled in the art will appreciate that, in some embodiments, additional components and/or steps can be utilized, and disclosed components and/or steps can be combined or omitted. For example, although some embodiments are described in connection with a robotic surgery system, the disclosure is not so limited. Systems, devices, and methods described herein can be applicable to medical procedures in general, among other uses. As another example, certain components can be illustrated and/or described as being circular or cylindrical. In some implementations, the components can be additionally or alternatively include non-circular portions, such as portions having straight lines. As yet another example, any of the actuators described herein can include one or more motors, such as electrical motors. As yet another example, in addition to or instead of controlling tilt and/or pan of a camera, roll (or spin) can be controlled. For example, one or more actuators can be provided for controlling the spin.

The foregoing description details certain embodiments of the systems, devices, and methods disclosed herein. It will be appreciated, however, that no matter how detailed the foregoing appears in text, the systems, devices, and methods can be practiced in many ways. The use of particular terminology when describing certain features or aspects of the disclosure should not be taken to imply that the terminology is being redefined herein to be restricted to including any specific characteristics of the features or aspects of the technology with which that terminology is associated.

It will be appreciated by those skilled in the art that various modifications and changes can be made without departing from the scope of the described technology. Such modifications and changes are intended to fall within the scope of the embodiments. It will also be appreciated by those of skill in the art that parts included in one embodiment are interchangeable with other embodiments; one or more parts from a depicted embodiment can be included with other depicted embodiments in any combination. For example, any of the various components described herein and/or depicted in the figures can be combined, interchanged, or excluded from other embodiments.

With respect to the use of substantially any plural and/or singular terms herein, those having skill in the art can translate from the plural to the singular and/or from the singular to the plural as is appropriate to the context and/or application. The various singular/plural permutations can be expressly set forth herein for sake of clarity.

Directional terms used herein (for example, top, bottom, side, up, down, inward, outward, etc.) are generally used with reference to the orientation or perspective shown in the figures and are not intended to be limiting. For example, positioning "above" described herein can refer to positioning below or on one of sides. Thus, features described as being "above" may be included below, on one of sides, or the like.

It will be understood by those within the art that, in general, terms used herein are generally intended as "open" terms (for example, the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims can contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (for example, "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (for example, the bare recitation of "two recitations," without other modifiers, typically means at least two recitations, or two or more recitations).

The term "comprising" as used herein is synonymous with "including," "containing," or "characterized by," and is inclusive or open-ended and does not exclude additional, unrequited elements or method steps.

Conditional language, such as "can," "could," "might," or "may," unless specifically stated otherwise, or otherwise understood within the context as used, is generally intended to convey that certain embodiments include, while other embodiments do not include, certain features, elements, and/or steps. Thus, such conditional language is not generally intended to imply that features, elements, and/or steps are in any way required for one or more embodiments or that one or more embodiments necessarily include logic for deciding, with or without user input or prompting, whether these features, elements, and/or steps are included or are to be performed in any particular embodiment.

Language of degree used herein, such as the terms "approximately," "about," "generally," and "substantially" as used herein represent a value, amount, or characteristic close to the stated value, amount, or characteristic that still performs a desired function and/or achieves a desired result. For example, the terms "approximately", "about", "generally," and "substantially" may refer to an amount that is within less than 10% of, within less than 5% of, within less than 1% of, within less than 0.1% of, and/or within less than 0.01% of the stated amount.

It will be further understood by those within the art that any disjunctive word and/or phrase presenting two or more alternative terms, whether in the description, claims, or drawings, can be understood to contemplate the possibilities of including one of the terms, either of the terms, or both terms. For example, the phrase "A or B" will be understood to include the possibilities of "A" or "B" or "A and B." Further, the term "each," as used herein, in addition to having its ordinary meaning, can mean any subset of a set of elements to which the term "each" is applied.

Conjunctive language such as the phrase "at least one of X, Y, and Z," unless specifically stated otherwise, is otherwise understood with the context as used in general to convey that an item, term, etc. may be either X, Y, or Z. Thus, such conjunctive language is not generally intended to imply that certain embodiments require the presence of at least one of X, at least one of Y, and at least one of Z.

The above description discloses embodiments of systems, apparatuses, devices, methods, and materials of the present disclosure. This disclosure is susceptible to modifications in the components, parts, elements, steps, and materials, as well as alterations in the fabrication methods and equipment. Such modifications will become apparent to those skilled in the art from a consideration of this disclosure or practice of the disclosure. Consequently, it is not intended that the disclosure be limited to the specific embodiments disclosed herein, but that it cover all modifications and alternatives coming within the scope and spirit of the subject matter embodied in the following claims.

What is claimed is:

1. An insertion device for a single port robotic surgery apparatus, the insertion device comprising:
    an insertion section comprising first and second camera channels and an instrument channel extending along at least a portion of the insertion section, the first camera channel configured to facilitate insertion and removal of a primary camera from the insertion section, the second camera channel configured to enclose a secondary camera, and the instrument channel configured to permit insertion and removal of a surgical instrument from the insertion section wherein the second camera channel is positioned between the first camera channel and the instrument channel; and
    a housing attached to the insertion section, the housing comprising a passage configured to permit at least a portion of the primary camera to pass through the housing into the first camera channel and exit the first camera channel, the housing configured to be removably attached to a robotic surgery apparatus,
    wherein the secondary camera is configured to provide image data of a surgical site to facilitate insertion into the surgical site of at least one of the surgical instrument or the primary camera.

2. The insertion device of claim 1, wherein the secondary camera is configured to provide the image data of the surgical site prior to attachment of the housing to the robotic surgery apparatus.

3. The insertion device of claim 2, wherein attachment of the housing to the robotic surgery apparatus comprises mounting the housing with a mounting interface of the robotic surgery apparatus.

4. The insertion device of claim 1, wherein the secondary camera comprises prism positioned at a distal end of the secondary camera, the prism configured to cause a field of view of the secondary camera to be oriented downward.

5. The insertion device of claim 4, wherein the secondary camera comprises a lens, and wherein the prism is positioned closer to the distal end of the secondary camera than a lens of the secondary camera.

6. The insertion device of claim 1, wherein the second camera channel is configured to enclose a device configured to image the surgical site or perform another function when the secondary camera has been removed.

7. The insertion device of claim 1, wherein the passage is vertically aligned with the first camera channel.

8. The insertion device of claim 1, wherein the secondary camera is integral with the second camera channel.

9. The insertion device of claim 1, wherein the instrument channel comprises a plurality of instrument channels configured to permit insertion and removal of a plurality of surgical instruments.

10. An insertion device for a single port robotic surgery apparatus, the insertion device comprising:
an insertion section comprising first and second camera channels and an instrument channel extending along at least a portion of the insertion section, the first camera channel configured to facilitate insertion and removal of a primary camera from the insertion section, the second camera channel configured to enclose a secondary camera, and the instrument channel configured to permit insertion and removal of a surgical instrument from the insertion section, wherein the second camera channel comprises a plurality of second camera channels enclosing a plurality of secondary cameras; and
a housing attached to the insertion section, the housing comprising a passage configured to permit at least a portion of the primary camera to pass through the housing into the first camera channel and exit the first camera channel, the housing configured to be removably attached to a robotic surgery apparatus,
wherein the secondary camera is configured to provide image data of a surgical site to facilitate insertion into the surgical site of at least one of the surgical instrument or the primary camera.

11. The insertion device of claim 10, wherein the plurality of second camera channels comprises two second camera channels positioned on opposite sides of the first camera channel and adjacent to the first camera channel.

12. An insertion device for a single port robotic surgery apparatus, the insertion device comprising:
an insertion section comprising first and second camera channels and an instrument channel extending along at least a portion of the insertion section, the first camera channel configured to facilitate insertion and removal of a primary camera from the insertion section, the second camera channel configured to enclose a secondary camera, and the instrument channel configured to permit insertion and removal of a surgical instrument from the insertion section, wherein the secondary camera comprises a fisheye lens; and
a housing attached to the insertion section, the housing comprising a passage configured to permit at least a portion of the primary camera to pass through the housing into the first camera channel and exit the first camera channel, the housing configured to be removably attached to a robotic surgery apparatus,
wherein the secondary camera is configured to provide image data of a surgical site to facilitate insertion into the surgical site of at least one of the surgical instrument or the primary camera.

13. A robotic surgery system comprising:
an insertion device for a single port robotic surgery apparatus, the insertion device including:
an insertion section comprising first and second camera channels and an instrument channel extending along at least a portion of the insertion section, the first camera channel configured to facilitate insertion and removal of a primary camera from the insertion section, the second camera channel configured to enclose a secondary camera, and the instrument channel configured to permit insertion and removal of a surgical instrument from the insertion section, wherein the secondary camera is configured to provide image data of a surgical site to facilitate insertion into the surgical site of at least one of the surgical instrument or the primary camera, wherein the image data comprises first image data captured by the secondary camera and second image data captured by the primary camera; and
a housing attached to the insertion section, the housing comprising a passage configured to permit at least a portion of the primary camera to pass through the housing into the first camera channel and exit the first camera channel, the housing configured to be removably attached to a robotic surgery apparatus; and
a robotic surgery workstation including:
a first display configured to display image data received from at least one of the primary or secondary camera; and
electronic circuitry configured to receive the image data and to control the first display to display the image data, the electronic circuitry is configured to:
control the first display to display the first image data; and
control the first display to display the second image data in response to a determination that the primary camera is connected.

14. The system of claim 13, wherein the determination that the primary camera is connected comprises at least one of a determination that the primary camera is mounted to a mounting interface of the system, a determination that primary camera is electrically connected to the electronic circuitry, or a determination that a distal portion of the primary camera has exited out the first camera channel.

15. The system of claim 13, wherein the electronic circuitry is configured to control the first display to display the first image data overlaid on the second image data in response to the determination that the primary camera is connected.

16. The system of claim 13, further comprising a second display, wherein the electronic circuitry is configured to control the second display to display the first image data when the first display displays the second image data and not the first image data.

17. The system of claim 13, wherein the electronic circuitry is configured to control the first display to display the first image in response to a determination that the primary camera is disconnected.

18. The system of claim 17, wherein the determination that the primary camera is disconnected comprises at least one of: a determination that the primary camera is not mounted to a mounting interface of the system, a determination that the primary camera is not electrically connected to the electronic circuitry, a determination that a distal portion of the primary camera has not exited the first camera channel, a determination that the primary camera has failed, or a determination that the primary camera is not communicating with the electronic circuitry.

* * * * *